United States Patent [19]

Johnson et al.

[11] 4,371,720
[45] Feb. 1, 1983

[54] 2-HYDROXY-4-(SUBSTITUTED) PHENYL CYCLOALKANES AND DERIVATIVES

[75] Inventors: Michael R. Johnson, Gales Ferry; Lawrence S. Melvin, Jr., Ledyard, both of Conn.

[73] Assignee: Pfizer Inc., New York, N.Y.

[21] Appl. No.: 286,661

[22] Filed: Jul. 28, 1981

Related U.S. Application Data

[63] Continuation-in-part of Ser. No. 188,795, Sep. 19, 1980, abandoned.

[51] Int. Cl.³ .................................. C07C 39/11
[52] U.S. Cl. ................................ 568/731; 560/60; 560/141; 560/255; 568/644; 568/660; 568/743
[58] Field of Search ............. 568/731, 743, 644, 660; 560/60, 141, 255

[56] References Cited

U.S. PATENT DOCUMENTS

| | | | |
|---|---|---|---|
| 3,576,887 | 4/1971 | Hughes et al. | 260/619 |
| 3,974,157 | 8/1976 | Shetty et al. | 260/247.2 |
| 4,306,097 | 12/1981 | Harbert et al. | 568/644 |

OTHER PUBLICATIONS

Official Gazette, (1-6-81), p. 300.
Official Gazette, (4-21-81), p. 1219.
Official Gazette, (5-19-81), p. 1246.
Official Gazette, (8-11-81), p. 717.
Official Gazette, (6-29-82), p. 1778.
Official Gazette, (6-24-80), p. 1423.
Chemical Abstracts 85, 176952f (1976).

*Primary Examiner*—Robert W. Ramsuer
*Attorney, Agent, or Firm*—Charles J. Knuth; Albert E. Frost; Peter C. Richardson

[57] ABSTRACT

Compounds having the formula

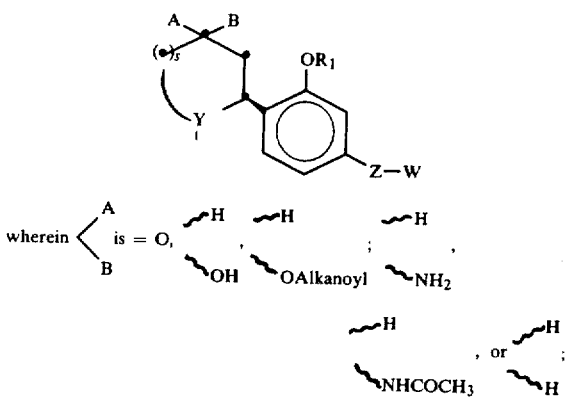

$R_1$ is hydrogen, benzyl or an ester moiety;
$Y$ is $-CH(R_2'')CH(R_2)-$ or $-CH(R_3)CH_2-$;
$R_2''$ is hydrogen or methyl;
$R_2$ is OH or X-substituted $(C_{1-6})$alkyl;
$R_3$ is OH, cyano or X-substituted $(C_{1-3})$ alkyl;
$X$ is $-OR_6$, $-SR_6$, $-S(O)R_6$, $-S(O)_2R_6$, $-NR_6R_7$, $-COOR_7$, $-CONR_7R_8$ or oxo;
with the proviso that when X is $-NR_6R_7$, $-COOR_7$ or $-CONR_7R_8$, said group is located on the terminal carbon atom of $R_2$ or $R_3$;
$R_6$ is hydrogen, $(C_{1-6})$alkyl or acetyl;
each of $R_7$ and $R_8$ is hydrogen or $(C_{1-6})$alkyl;
s is an integer of 1 or 2;
with the proviso that when $R_6$ is acetyl, $R_7$ is hydrogen and X is other than $S(O)R_6$ or $S(O)_2R_6$;
$Z-W$ is alkyl, phenylalkyl or pyridylalkyl which can have an oxygen atom as part of the alkyl chain, and their use as CNS agents, antidiarrheals and antiemetics. Processes for their preparation and intermediates therefor are described.

10 Claims, No Drawings

2-HYDROXY-4-(SUBSTITUTED) PHENYL CYCLOALKANES AND DERIVATIVES

CROSS REFERENCE TO RELATED APPLICATION

This application is a continuation-in-part of U.S. application Ser. No. 188,795, filed Sept. 19, 1980, now abandoned.

BACKGROUND OF THE INVENTION

This invention relates to novel 3-[2-hydroxy-4-(substituted)phenyl]-4(or 5-)-substituted)cycloalkanones and cycloalkanols useful as analgesic agents and as antiemetic agents; to derivatives thereof, intermediates therefore and processes for their preparation.

Despite the current availability of a number of analgesic agents, the search for new and improved agents useful for the control of broad levels of pain and accompanied by a minimum of side-effects continues. The most commonly used agent, aspirin, is of no practical value for the control of severe pain and is known to exhibit various undesirable side-effects. Other analgesic agents, such as merperidine, codeine, and morphine, possess addictive liability. The need for improved and potent analgesic agents is, therefore, evident.

Compounds having utility as analgesics, tranquilizers, sedatives, antianxiety agents and/or as anticonvulsants, diuretics and antidiarrheal agents are described in Belgian Pat. Nos. 870,404 and 870,402, both granted Mar. 12, 1979. Belgian Pat. No. 870,404 describes 3-[2-hydroxy-4-(substituted)phenyl]cycloalkanones and cycloalkanols which may have at the 4-position of the cycloalkanone or cycloalkanol residue, an alkyl, alkenyl, phenyl or phenylalkyl substituent; or, at the 5-position, an alkyl substituent, and Belgian Pat. No. 870,402 discloses certain 2-(acyclic substituted)phenols; namely, 2-(hydroxyalkyl)-4-(substituted)phenols and 2-(oxoalkyl)-4-(substituted)phenols.

U.S. Pat. No. 3,576,887, issued Apr. 27, 1971, discloses a series of 1-(1'-hydroxy)alkyl-2-(o-hydroxyphenyl)cyclohexanes which exhibit central nervous system depressant properties.

Our concurrently filed application, Ser. No. 189,402, filed Sept. 19, 1980, entitled "Pharmacologically Active 4-[2-Hydroxy-4-(Substituted)phenyl]Naphthalen-2(1H)-ones and 2-ols, Derivatives Thereof and Intermediates Therefore," describes a series of 4-[2-hydroxy-4-(substituted)-phenyl]naphthalen-2(1H)-ones and 2-ols useful as CNS agents and as antiemetic agents.

U.S. Pat. No. 3,974,157 describes 2-phenylcyclohexanones which can be substituted in the phenyl ring with up to two alkyl, hydroxy or alkoxy groups as intermediates for preparation of 1-(aminoalkyl)-2-phenylcyclohexanols useful as analgesics, local anesthetics and antiarrhythmics.

Chemical Abstracts 85, 176952f (1976) discloses a number of 3-phenyl- and 3-phenylalkylcylochexanones as intermediates for 2-aminomethyl-3-phenyl (or phenylalkyl)cyclohexanones which exhibit analgesic, sedative, antidepressant and anticonvulsant activities.

SUMMARY OF THE INVENTION

The compounds of this invention have the formulae

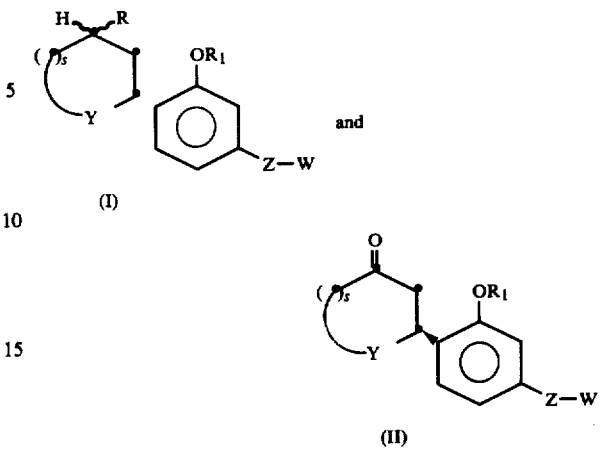

wherein
R is hydrogen, hydroxy, alkanoyloxy having from one to five carbon atoms, amino or acetamido;
$R_1$ is hydrogen, benzyl, alkanoyl having from one to five carbon atoms, $P(O)(OH)_2$ and mono- and disodium and potassium salts thereof, $—CO(CH_2)_2COOH$ and the sodium and potassium salts thereof, or $—CO(CH_2)_pNR_4R_5$ wherein p is 0 or an integer from 1 to 4, each of $R_4$ and $R_5$ when taken individually is hydrogen or alkyl having from one to four carbon atoms; $R_4$ and $R_5$ when taken together with the nitrogen to which they are attached form a 5- or 6-membered heterocyclic ring (piperidino, pyrrolo, pyrrolidino, morpholino and N-alkylpiperazino having from one to four carbon atoms in the alkyl group);
s is an integer of 1 or 2;
y is $—CH(R_2")CH(R_2)—$ or $CH(R_3)CH_2$;
$R_2"$ is hydrogen or methyl;
$R_2$ is hydroxy or X-substituted alkyl having from one to six carbon atoms;
$R_3$ is hydroxy, cyano or X-substituted alkyl having from one to three carbon atoms;
X is $—OR_6$, $—NR_6R_7$, $—COOR_7$, $—CONR_7R_8$ or oxo;
$R_6$ is hydrogen, alkyl having from one to six carbon atoms or acetyl;
each of $R_7$ and $R_8$ is hydrogen or alkyl having from one to six carbon atoms;
provided that when X is $—NR_6R_7$, $—COOR_7$ or $—CONR_7R_8$, it is located on the terminal carbon atom of $R_2$ or $R_3$; and when $R_6$ is acetyl, $R_7$ is hydrogen;
W is hydrogen, pyridyl or

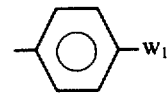

wherein $W_1$ is hydrogen, chloro or fluoro, provided that
when W is hydrogen, Z is
(a) alkylene having from five to thirteen carbon atoms; or
(b) $-(alk_1)_m-O-(alk_2)_n-$ wherein each of $(alk_1)$ and $(alk_2)$ is alkylene having from one to thirteen carbon atoms; each of m and n is 0 or 1; with the provisos that the summation of carbon atoms in (alk$_1$) plus (alk$_2$) is not less than five or greater than thirteen; and at least one of m and n is 1;

when W is other than hydrogen, Z is (a) alkylene having from three to eight carbon atoms; or (b) -(alk$_1$)$_m$-O-(alk$_2$)$_n$- wherein each of (alk$_1$) and (alk$_2$) is alkylene having from one to eight carbon atoms; each of m and n is 0 or 1; with the provisos that the summation of carbon atoms in (alk$_1$) plus (alk$_2$) is not less than three or greater than eight; and at least one of m and n is 1;

In each of formulae I and II, the Y variable is positioned in the cycloalkyl moiety in such manner that R$_2$ is always a 4-position substituent and each of R$_2''$ and R$_3$ is always a 5-position substituent.

Also included in this invention as noted above are the pharmaceutically acceptable acid addition salts of those compounds of formulae I and II which contain one or more basic groups. Typical of such compounds are those wherein the W variable is pyridyl and/or OR$_1$ represents a basic ester moiety; R$_2$ is aminoalkyl; R is amino. In compounds having more than one basic group present, polyacid addition salts are, of course, possible.

Representative of such pharmaceutically acceptable acid addition salts are the mineral acid salts such as the hydrochloride, hydrobromide, sulfate, phosphate, nitrate; organic acid salts such as the citrate, acetate, sulfosalicylate, tartrate, glycolate, malate, malonate, maleate, pamoate, salicylate, stearate, phthalate, succinate, gluconate, 2-hydroxy-3-naphthoate, lactate, mandelate and methanesulfonate.

Compounds of formula II wherein R$_1$ is hydrogen exist, in solution, in equilibrium with their hemiketal forms. The keto and hemiketal forms of said compounds of formula II are included in this invention.

Compounds of formulae I and II contain asymmetric centers at the 3-, the 4- and the 5-positions in the cycloalkyl moiety and may, of course, contain additional asymmetric centers in (—Z—W) of the phenyl ring. Formula I compounds, of course, contain an asymmetric center at the 1-position when R is other than hydrogen. Cis-relationship between the substituent at the 1-position of the cycloalkyl moiety and the phenolic, or substituted phenolic, moiety at the 3-position of formula I is favored, and trans-relationship between the 3- and 4-substituents and the 3- and 5-substituents on the cycloalkyl moiety are favored because of the greater (quantitatively) biological activity. For the same reason, the trans-3,4 and 3,5-relationship is also favored in compounds of formula II.

For convenience, the above formulae depict the racemic compounds. However, the above formulae are considered to be generic to and embracive of the racemic modifications of the compounds of this invention, the diastereomeric mixtures, the pure enantiomers and diastereomers thereof. The utility of the racemic mixture, the diastereomeric mixture as well as of the pure enantiomers and diastereomers is determined by the biological evaluation procedures described below.

Favored because of their greater biological activity relative to that of other compounds described herein are compounds of formulae I and II wherein each of R is hydroxy or acetamido; R$_1$ is hydrogen; R$_2''$ is hydrogen or methyl; each of R$_2$ and R$_3$ is hydroxyalkyl, alkoxyalkyl, carboalkoxyalkyl or dialkylaminoalkyl; and Z and W have the values shown below:

| Z | m | n | W |
|---|---|---|---|
| C$_{7-11}$ alkylene | — | — | H |
| C$_{4-7}$ alkylene | — | — | 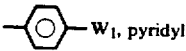 |
| —(alk$_1$)$_m$—O—(alk$_2$)$_n$— | 0,1 | 1 | 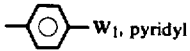 | each of (alk$_1$) and (alk$_2$) is C$_{1-7}$ alkylene with the proviso that the summation of carbon atoms in (alk$_1$) plus (alk$_2$) is not less than four or greater than seven;

| —(alk$_1$)$_m$—O—(alk$_2$)$_n$— | 0,1 | 1 | H | each of (alk$_1$) and (alk$_2$) is C$_{1-11}$alkylene with the proviso that the summation of carbon atoms in (alk$_1$) plus (alk$_2$) is not less than seven or greater than eleven.

Preferred compounds of formulae I and II are those favored compounds wherein:

each of R$_2''$ and R$_1$ is hydrogen;
Z is C(CH$_3$)$_2$(CH$_2$)$_6$ and W is hydrogen;
Z is C$_{4-7}$ alkylene and W is phenyl;
Z is -O-alkylene having 7 to 9 carbon atoms and W is hydrogen;
Z is -O-alkylene having from 4 to 5 carbon atoms and W is phenyl;
R of formula I is hydroxy (cis- and trans-forms);
R$_2$ = ω-hydroxy(C$_{2-4}$)alkyl or ω-methoxy(C$_{2-4}$)alkyl;
R$_3$ = hydroxyalkyl or methoxyalkyl.

Especially preferred are compounds of formulae I and II wherein R, R$_1$, Z and W are as defined for the preferred compounds; R$_2$ is 3-hydroxypropyl or 3-methoxypropyl; and R$_3$ is hydroxymethyl. The 1-form of a given compound is preferred over the d-form thereof.

DETAILED DESCRIPTION OF THE INVENTION

The compounds of this invention having formulae I or II wherein Y is -CH(R$_2''$)CH(R$_2$)- are prepared from the appropriate 2-bromo-5-(Z-W substituted)phenol by a series of reactions which comprises as the first step protection of the phenolic group. Suitable protecting groups are those which do not interfere with the subsequent reactions and which can be removed under conditions which do not cause undesired reactions at other sites of said compounds or of products produced therefrom. Representative of such protective groups are those phenolic protecting groups described by Haslam in Chapter 4 of "Protective Groups in Organic Chemistry," Edited by J. F. W. McOmie, Plenum Press, London and New York (1973). Favored groups are methyl, ethyl, tetrahydropyranyl, benzyl or substituted benzyl wherein the substituent is, for example, alkyl having from one to four carbon atoms, halo (Cl, Br, F, I) and alkoxy having from one to four carbon atoms. The ether protecting, or blocking, groups can be removed through the use of hydrobromic acid in acetic acid or hydrobromic acid, 48% aqueous. The reaction is conducted at elevated temperatures and desirably at the reflux temperature. However, when Z is -(alk$_1$)$_m$-O-(alk$_2$)$_n$-, acids such as polyphosphoric acid or trifluoroacetic acid must be used to avoid cleavage of the ether linkage. Other reagents such as hydriodic acid, pyridine hydrochloride or hydrobromide can be used to remove protecting ether groups such as methyl or ethyl groups. When the protecting groups are benzyl or substituted benzyl groups, they can be removed by catalytic hydrogenolysis. Suitable catalysts are palladium or platinum, especially when supported on carbon. Alternatively, they can be removed by solvolysis using trifluoroacetic acid. A further procedure comprises treatment with n-butyllithium in a reaction-inert solvent at room temperature.

The exact chemical structure of the protecting group is not critical to this invention since its importance resides in its ability to perform in the manner described above. The selection and identification of appropriate protecting groups can easily and readily be made by one skilled in the art. The suitability and effectiveness of a group as a hydroxy protecting group are determined by employing such a group in the herein-illustrated reaction sequences. It should, therefore, be a group which is easily removed to regenerate the hydroxy groups. Methyl, tetrahydropyranyl and benzyl are preferred protecting groups since they are readily removed.

The protected 2-bromo-5-(Z-W substituted)phenol is then reacted with magnesium in a reaction-inert solvent and generally in the presence of a promoter, e.g., cuprous salts such as the chloride, bromide and iodide (to promote 1,4-addition) with the appropriate 4-$R_2'$-2-cycloalken-1-one (e.g., 4-$R_2'$-2-cyclohexen-1-one) wherein $R_2'$ is alkenyl or X'-substituted alkyl wherein X' is X or a precursor therefor, e.g., -Obenzyl as precursor for —OH; —CH(OCH$_3$)$_2$ or —HCOCH$_2$CH$_2$O as precursor for —CHO. Suitable reaction-inert solvents are cyclic and acyclic ethers such as, for example, tetrahydrofuran, dioxane and dimethyl ether of ethylene glycol (diglyme). The Grignard reagent is formed in known manner, as, for example, by refluxing a mixture of one molar proportion of the bromo reactant and two molar proportions of magnesium in a reaction-inert solvent, e.g., tetrahydrofuran. The resulting mixture is then cooled to about 0° C. to −20° C. The amount of cuprous iodide used is not critical, but can vary widely. Molar proportions ranging from about 0.2 to about 0.02 moles per mole of bromo reactant afford satisfactory yields of the cycloalkanone wherein the phenolic hydroxy group is protected (formula II, $R_1$=a protecting group).

Alternatively, compounds of formulae I and II are prepared by reaction of the copper derivative of an appropriate 3-(Z-W-substituted)phenol, the hydroxy group of which is suitably protected, with an appropriate 4- or 5-substituted cycloalk-2-en-1-one in a reaction-inert solvent at a low temperature, e.g., below −20° C. Suitable protecting groups are those enumerated above except, of course, benzyl or substituted benzyl which would be removed during preparation of the precursor lithio derivative of the copper 3-(Z-W)phenol. An especially useful protecting group for this alternative methodology is the tetrahydropyranyl group. Said protecting group is easily introduced into the phenol reactant, is stable to the conditions of subsequent reactions in which said protected compound serves as intermediate, and is conveniently removed by hydrolysis.

The copper derivative of the 3-(Z-W-substituted)phenol is prepared from the lithio derivative of said phenol by treatment of said lithio derivative with 1-hexyne copper. It undergoes 1,4-addition to the conjugated C≡C—C═O system of the cycloalk-2-en-1-one reactant, in contrast to the characteristic 1,2-addition of the corresponding lithio derivative.

This alternative 1,4-addition step, of course, gives rise to the same compounds as does the above-described Grignard reaction. It generally affords better yields of the formulae II and I compounds.

It will be noted that in a preparation of a compound of formula I herein wherein each of R and $R_1$ is hydroxy, Y is —CH$_2$CHR$_2$—, $R_2$ is (CH$_2$)$_3$OH and Z-W is 1,1-dimethylheptyl, the particular sequence exemplified (Examples 91–96) utilizes intermediates wherein the Z-W group is 1,1-dimethyl-2-heptenyl and which is hydrogenated in the last step of the sequence to 1,1-dimethylheptyl. Reduction of said 1,1-dimethyl-2-heptenyl group can, of course, be accomplished at any stage of the sequence if desired, i.e., it need not be delayed until the final step.

The protected cycloalkanone is then treated with an appropriate reagent to remove the protecting group, if desired. The benzyl group is conveniently removed by the method described above. If the protecting group is an alkyl group (methyl or ethyl), it is removed by the above-mentioned methods or by treatment with, for example, pyridine hydrochloride. The tetrahydropyranyl group is removed by means of an acidic reagent.

When the appropriate 4-$R_2'$-2-cycloalken-1-one is not available or is not readily obtainable by known methods, compounds of formula II wherein $R_2$ is oxo-substituted (C$_{1-6}$)alkyl, and especially those wherein $R_2$ is formyl, serve as intermediates for all other formulae I and II compounds.

When $R_2'$ is an alkenyl group, the cycloalkanones (formula II) thus produced serve as intermediates for preparation of the corresponding cycloalkanones wherein $R_2$ is substituted alkyl as defined above.

The cycloalkanol compounds having formula I are prepared from the protected cycloalkanones by reduction. Sodium borohydride is favored as reducing agent in this step since it not only affords satisfactory yields of the desired product, but retains the protecting group on the phenolic hydroxy group, and reacts slowly enough with hydroxylic solvents (methanol, ethanol, water) to permit their use as solvents. Temperatures of from about −40° C. to about 30° C. are generally used. Lower temperatures, even down to about −70° C., can be used to increase selectivity of the reduction. Higher temperatures cause reaction of the sodium borohydride with the hydroxylic solvent. If higher temperatures are desired, or required for a given reduction, isopropyl alcohol or the dimethyl ether of diethylene glycol are used as solvents. Sometimes favored as reducing agent is potassium tri-sec-butyl borohydride since it favors stereoselective formation of the trans-1,3-phenylcycloalkanol. The reduction is conducted in dry tetrahydrofuran at a temperature below about −50° C. using equimolar quantities of the ketone compound and reducing agent.

Reducing agents such as lithium borohydride, diisobutylaluminum hydride or lithium aluminum hydride which can also be used, require anhydrous conditions and non-hydroxylic solvents, such as 1,2-dimethoxyethane, tetrahydrofuran, diethyl ether, dimethyl ether of ethylene glycol.

The cycloalkanols of formula I wherein OR$_1$ is hydroxy can, of course, be obtained directly by catalytic reduction of the protected cycloalkanone over palladium-on-carbon or by catalytic reduction or chemical reduction of the unprotected cycloalkanone (formula II, $OR_1=OH$) using the reducing agents described above.

In actual practice it is preferred to produce the unprotected cycloalkanols of formula I ($OR_1=OH$) via reduction of the benzyl protected cycloalkanones ($OR_1=$ benzyloxy) as described above, since it permits stereochemical control of the reduction and formation of the cis-hydroxy epimer as the major product and thus facilitates separation and purification of the epimeric alcohols.

Compounds wherein $R_2'$ is alkenyl are transformed to corresponding hydroxyalkyl derivatives via hydroboration-oxidation using borane in tetrahydrofuran or diethyleneglycol dimethyl ether (diglyme) at 0° to 50° C. The intermediate borane product is not isolated but is directly oxidized with alkaline hydrogen peroxide to the alcohol. The alcohols thus produced correspond to anti-Markovnikov addition of the elements of water to the double bond.

Further, hydroxyalkyl derivatives can also be produced by oxymercuration-demercuration using mercuric acetate in water followed by reduction (sodium borohydride) of the intermediate hydroxy mecurial derivative. The reaction is carried out at ambient temperature using an aqueous mercuric acetate/tetrahydrofuran medium. The intermediate is not separated, but is reduced in situ to the alcohol. Addition occurs opposite to that of the hydroboration-oxidation reaction; namely, Markovnikov addition, the elements of water being added to the double bond in a manner opposite to that of the hydroboration-oxidation reaction to produce secondary alcohols.

The alcohols serve as intermediates for production of corresponding aldehydes and ketones (oxoalkyl compounds) by oxidation with a suitable oxidizing agent such as pyridinium chlorochromate. The resulting oxo compounds in turn serve as intermediates for increasing the chain length of $R_2$ or $R_3$ alkyl groups having said oxo functionality and, of course, for introducing branching into said alkyl group. The Wittig reaction, using the appropriate ylide, serves admirably for this purpose. For example, reaction of an oxoalkyl group with triphenylphosphonium methylide converts the oxo group to a methylene ($=CH_2$) group. Hydroboration-oxidation, affords a primary or secondary alcohol, itself a useful intermediate.

Formulae I and II compounds wherein $R_2$ or $R_3$ is oxo substituted alkyl are conveniently prepared by oxidation of corresponding compounds wherein $R_2'$ or $R_3$ is an alkenyl group having one more carbon atom than $R_2$ or $R_3$. Sodium metaperiodate and a catalytic amount of osmium tetroxide in aqueous tetrahydrofuran or dioxane at ambient temperature is favored as oxidizing agent since it tends to minimize oxidation beyond the aldehyde stage. However, despite its relative mildness as an oxidant compared to, for example, sodium metaperiodate/potassium permanganate, some oxidation to the corresponding acid and the corresponding hydroxy ketone does occur.

They can also be prepared by Grignard reaction of the appropriate 4-(acetal or ketal substituted alkyl)-2-cycloalken-1-one with the appropriate 2-bromo-5-(Z-W substituted)phenol according to the procedure described above. The acetal or ketal group is then transformed by treatment with acid, e.g., a mineral acid such as HCl, to the oxo group.

A favored procedure for preparation of compounds of formulae I and II wherein Z-W is -O-(alk$_2$)-W comprises selective alkylation of the appropriate 3-(2,4-dihydroxyphenyl)-4-($R_2'$-substituted)-2-cycloalkan-1-one in a reaction-inert solvent according to the procedure described below. The 3-(2,4-dibenzyloxyphenyl)-4-($R_2'$-substituted)-cycloalkanone is then, if no transformations are to be carried out on the $R_2'$-group, debenzylated via hydrogen over palladium-on-charcoal to the corresponding 3-(2,4-dihydroxyphenyl-4-($R_2'$-substituted)cycloalkanone and then converted to a ketal.

Ketal formation is accomplished according to well-known procedures for ketalization, such as reaction of said 3-(2,4-dihydroxyphenyl)cycloalkanone with an alcohol, especially an alcohol having from one to four carbon atoms, in the presence of an acid, such as sulfuric acid, p-toluenesulfonic acid, hydrogen chloride, under conditions which remove the by-product water. A favored procedure comprises reaction of said 3-(2,4-dihydroxyphenyl)cycloalkanone with an orthoformic ester in solution in an alcohol corresponding to the alcohol moiety of the orthoformic ester. Trimethyl orthoformate and methanol are favored reactants along with concentrated sulfuric acid, anhydrous hydrogen chloride, or ammonium chloride as catalyst.

The ketal thus produced is then alkylated by reaction with an appropriate alkylating agent such as W—Z—X″ wherein W and Z are as defined above, and X″ is selected from the group consisting of chloro, bromo, mesyloxy ($CH_3$—$SO_2$—O) and tosyloxy (p—$CH_3$—$C_6H_4$—$SO_2$—O) in the presence of an acid acceptor, e.g., sodium or potassium carbonate. The alkylated ketal is then deketalized by treatment with aqueous acid according to known procedures.

The 3-[2-hydroxy-4-(-O-(alk$_2$)-W-substituted)-phenyl]-4-($R_2'$-substituted)cycloalkanones thus produced are converted to corresponding cycloalkanols by procedures described above.

When transformations are to be conducted on group $R_2'$ as precursor to group $R_2$, e.g., alkenyl to hydroxyalkyl; —CH(OCH$_3$)$_2$ to —CHO; the desired transformations are carried out prior to removal of the protective, i.e., benzyl groups. For example, when $R_2'$ is alkenyl, said group is hydrated via the hydroboration-oxidation procedure described above, either by direct conversion from the 3-(2,4-dibenzyloxyphenyl)-4-(2-propenyl)cycloalkanone, or by first converting the ketone to a ketal, followed by hydration of the propenyl group and then deketalization.

Formula I and II compounds wherein $R_2$ is oxo substituted alkyl serve as intermediates for preparation of oxo substituted alkyl derivatives having increased chain length via the Wittig reaction. A representative procedure comprises, for example, reacting an appropriate 2-(1,3-dioxolan-2-yl)alkyl triphenylphosphonium bromide at about 10° C. to about 80° C. with sodium dimsylate in dimethyl sulfoxide to generate the corresponding ylide in situ. To the thus produced ylide is then added an appropriate reactant such as 3-(2-benzyloxy-4-(Z-W substituted)phenyl-4-(2-oxoethyl)cycloalkanone ethylene ketal in a suitable solvent such as dimethyl sulfoxide at a temperature of from about 10° C. to about 80° C. The product, a 3-(2-benzyloxy-4-(Z-W substituted)-phenyl)-4-(ω-oxoalk-2-enyl)cycloalkanone bis ethylene ketal, is recovered by known methods such as extraction and column chromatography on silica gel. In this Wittig reaction, the oxo group of the cycloalkanone moiety is protected by conversion to a ketal. If desired, the product is subjected to acid hydrolysis to regenerate the oxo groups. However, when the product is to be subjected to further reactions, it is advantageous to retain the bis ethylene ketal protecting groups on the product.

Reduction of the protected ($\omega$-oxoalkenyl) group ($R_2$) of the thus produced compounds using catalytic hydrogenation over a noble metal catalyst, e.g., Pd/C, affords the corresponding protected ($\omega$-oxoalkyl) compound. Treatment of the reduced product with aqueous acid (HCl) as described herein provides the $\omega$-oxoalkyl derivative of formula II wherein $R_2$ is $\omega$-oxoalkyl. Sodium borohydride reduction affords a formula I compound wherein $R_2$ is $\omega$-hydroxyalkyl and R is hydroxy. The $\omega$-hydroxyalkyl group can be converted to an ether group by the Williamson Synthesis which comprises converting the alcohol to an alkali metal alkoxide followed by alkylation of said alkoxide with an alkyl halide or alkyl sulfate.

Formation of a secondary alcohol group in $R_2$ is readily achieved by Grignard reaction on an appropriate compound of formula II, the 1-oxo group of which is protected as an alkylene ketal, and in which $R_2$ is oxoalkyl.

Compounds wherein $R_2$ is carboalkoxy substituted alkyl are prepared via the Wittig reaction using the appropriate protected compound of formula II wherein $R_2$ is oxo substituted alkyl; i.e., an aldehyde or ketone group, and a trialkyl phosphonoacetate such as trimethyl or triethyl phosphonoacetate. The reaction is carried out in a reaction-inert solvent such as diethyl ether or tetrahydrofuran at ambient temperature using about one mole of aldehyde reactant to two moles of trialkyl phosphonoacetate. A proton acceptor such as sodium hydride, about ten mole percent in excess of the trialkyl phosphonoacetate is used. The alpha, beta-unsaturated carboxylic ester thus produced is then reduced, for example, by catalytic hydrogenation over Pd/C to provide the desired carboalkoxyalkyl derivative.

Alternatively, said compounds are produced by using a carboalkoxymethylene triphenylphosphorane in place of a trialkylphosphonoacetate. In such instances, the reaction is conducted in a reaction-inert solvent such as diethyl ether, tetrahydrofuran or methylene chloride at from about 20° C. to 80° C. A proton acceptor, e.g., n-butyllithium or phenyllithium is generally used. The alpha, beta-unsaturated carboxylic ester thus produced is reduced as before to give the formula I compound wherein $R_2$ is carbalkoxyalkyl. Hydrolysis, more desirably, saponification, using dilute (e.g., 6 N) sodium hydroxide at reflux, followed by acidification, affords the corresponding carboxyalkyl compound.

Compounds wherein $R_2$ is carbamoylalkyl or substituted carbamoylalkyl are prepared in like manner using the appropriate carbamoylmethylenetriphenylphosphorane in a reaction-inert solvent such as methylene chloride at reflux to provide the alpha, beta-unsaturated carboxylic acid amide which is then reduced ($H_2$, Pd/C) to the corresponding carbamoylalkyl derivative. By choice of the appropriate oxoalkyl derivative of formula I, carbalkoxyalkyl and carbamoylalkyl derivatives of varying chain length are produced.

Alternatively, said carbamoylalkyl derivatives are prepared by ammonolysis of the corresponding carbalkoxyalkyl derivative with the appropriate amine, $HNR_7R_8$, in a reaction-inert solvent. The temperature of the reaction depends upon the ester and amine reactants but ranges from room temperature to the reflux temperature of the solvent. In certain instances, the use of sealed tubes and elevated (e.g., reflux) temperatures are beneficial. However, satisfactory conditions for a given reaction are readily determined by simple experimentation. Representative solvents for this reaction are water, $C_{1-4}$ alcohols and excess of the chosen amine.

Still further, the carbamoylalkyl derivatives are prepared from corresponding carboxyalkyl derivatives via conversion of said derivatives to acid chlorides by reaction with thionyl chloride, phosphorous pentachloride or trichloride. Reaction with thionly chloride is favored since the by-products are gaseous and easily removed. In general, excess thionyl chloride is used to serve as solvent as well as reactant and the reaction carried out at a temperature of 20°-100° C. Acylation of the appropriate amine ($HNR_7R_8$) in a suitable solvent, e.g., water, by the Schotten-Baumann method; or in non-aqueous systems, e.g., tetrahydrofuran, dioxan, methylene chloride, in the presence of a tertiary amine (triethylamine, N-methylaniline). In either case, a temperature of from about 0° to about 50° C. is used.

Compounds of formulae I and II wherein Y is $-CH(R_3)CH_2-$ are prepared via the previously described Grignard reaction from the appropriate 5-[2-benzyloxy-4-(Z-W substituted)phenyl]-2-cycloalken-1-ones, the preparation of which are described in Belgian Pat. No. 870,404, published Mar. 12, 1979. Nucleophilic addition of the elements of HCN to said 2-cycloalken-1-one compounds by reaction thereof with aqueous sodium or potassium cyanide affords the corresponding trans-3-[2-benzyloxy-4-(Z-W substituted)-phenyl]-5-cyano cycloalkanones which are valuable intermediates. Reduction of the oxo group of the cycloalkanone moiety by means of sodium borohydride yields the corresponding trans-cis hydroxy compound. It is converted to the corresponding trans-trans compound by refluxing in t-butanol solution in the presence of potassium t-butoxide.

The stereoisomers cis-3[2-benzyloxy-4-(Z-W substituted)phenyl]-cis-5-cyanocycloalkanols are prepared by oxidation of the trans-trans stereoisomers using, for example, Jones' reagent followed by sodium borohydride reduction of the thus-produced cis-3-[2-benzyloxy-4-(Z-W substituted)phenyl]-5-cyanocycloalkanone.

Each of the above-mentioned 5-cyanocycloalkanol derivatives is also a valuable intermediate. The cyano group is readily converted by reduction with diisobutyl aluminum hydride (DIBAL-H) to the corresponding formyl derivative. The procedure comprises reacting the cyano derivative with DIBAL-H, two equivalents, in toluene at a low temperture, e.g., 0° C. to −65° C., followed by treating the reaction with dilute acid, e.g., a mineral acid such as sulfuric acid. The formyl derivative is recovered by standard procedures such as extraction with ether and evaporation of the solvent. Reduction of the formyl derivative, e.g., by sodium borohydride, affords the corresponding hydroxymethyl derivative. In the above reactions the benzyl ether derivative of the 3-(2-hydroxy-4-(Z-W substituted)phenyl)-5-cyanocycloalkanol is used as reactant in order to avoid reactions at the phenolic hydroxy group. The protecting benzyl group is removed by methods described above.

The 5-hydroxymethyl and 5-formyl derivatives serve as intermediates to other values of $R_3$ by means of the reactions described above as regards conversion of hydroxyalkyl and oxoalkyl values of $R_2$.

Formula I compounds wherein R is hydrogen are prepared from the corresponding compounds of formula II by first converting the oxo group to a hydrazone (or semicarbazone) and then decomposing said hydrazone (or semicarbazone) by alkali such as sodium or potassium hydroxide, to produce the corresponding hydrocarbon derivative. The process is readily carried out by heating a mixture of the appropriate cycloalkanone compound and hydrazine hydrate in a reaction-inert solvent such as ethylene glycol or triethylene glycol at 100° C. Solid potassium (or sodium) hydroxide is then added and the mixture heated at an elevated temperature, e.g., 150°–200° C. It is then cooled, acidified and the product recovered by known methods, e.g., by extraction with ether.

Compounds of this invention wherein $R_2$ or $R_3$ is amino substituted alkyl are prepared from the corresponding compounds wherein $R_2$ or $R_3$ are oxo substituted alkyl. One procedure comprises converting the appropriate oxo compound of formula I or II to the corresponding oxime or oxime derivative; e.g., an alkyl ether or an acetyl derivative, followed by reduction of the oxime or derivative thereof to the desired amine. Of course, when a compound of formula II is used as reactant, the 1-oxo group must be protected to avoid reaction at that site unless introduction of an amino group at said site is also described. The ketal group is a preferred protecting group because of the ease of preparation of said compounds and the relative ease of removal of said group to regenerate the oxo group.

The oximes of formulae I and II compounds wherein $R_2$ or $R_3$ is oxo substituted alkyl are prepared by reacting said compounds with hydroxylamine hydrochloride in a solution of methanol-water at room temperature. In practice, it is preferred to use an excess of hydroxylamine, up to as much as a three fold excess. Under such conditions the preparation of the desired oxime derivative is complete in 1 to 2 hours. The product is isolated by addition of the reaction mixture to water followed by basification to pH 9.5 and extraction with a water-immiscible solvent such as ethyl acetate.

The oxime or oxime derivative is then reduced catalytically using, for example, Raney nickel, palladium-on-charcoal or platinum oxide at an initial hydrogen pressure of about 2–3 atmospheres at ambient temperature in a reaction-inert solvent such as $C_{1-4}$ alkanol, or lithium aluminum hydride in a reaction-invert solvent such as tetrahydrofuran at reflux temperature.

A still further procedure comprises the Gabriel synthesis in which potassium phthalimide is reacted with a compound of formula I or II wherein $R_2$ or $R_3$ is halo(Br, I)alkyl and the resulting phthalimide derivative hydrolyzed with a base such as sodium or potassium hydroxide or hydrazine. The halo alkyl compounds of formulae I and II are prepared by reaction of the corresponding hydroxy compound with the appropriate phosphorous halide or hydrogen halide.

A favored procedure for preparing said amino compounds comprises condensation of the appropriate formula I or II compound wherein $R_2$ or $R_3$ is oxo-substituted alkyl with the ammonium salt of a lower alkanoic acid and subsequent reduction of the in situ generated imine. In addition to lower alkanoic acid ammonium salts, ammonium salts of inorganic acids can also be used in this procedure.

In practice, a solution of the appropriate oxoalkyl compound in a lower alkanol such as methanol is treated with an ammonium salt of an alkanoic acid such as acetic acid and the cooled reaction mixture treated with the reducing agent sodium cyanoborohydride. The reaction is allowed to proceed at room temperature for several hours, and is subsequently hydrolyzed and the product isolated.

Although stoichiometric proportions of ketone and ammonium alkanoate are required, it is advantageous to use up to a ten fold excess of ammonium alkanoate in order to ensure rapid formation of the imine. It is also advantageous to conduct the reduction at ambient temperature and to use two moles of sodium cyanoborohydride per mole of ketone reactant in order to maximize the yield of the final product. Reaction is complete in 2–3 hours.

Reduction of the imine can, of course, be carried out with other reducing agents such as palladium-on-charcoal. In practice, a solution of the appropriate ketone in a lower alkanol, such as methanol or isopropanol, is treated with an ammonium alkanoate, such as ammonium acetate, and 10% palladium-on-charcoal, and the resulting suspension shaken in a hydrogen atmosphere at temperatures of about 25°–50° C. until the theoretical amount of hydrogen has been absorbed. It is preferred that a 10 fold excess of the ammonium alkanoate be employed to ensure complete reaction in a reasonable time period. The amount of the catalyst can vary from 10% to 50% on a weight basis, of the starting ketone. The initial pressure of the hydrogen is not critical, and a pressure from one to fifty atmospheres is preferred to shorten the reaction time. Employing the aforementioned parameters, the reaction time will vary between 2 to 6 hours. Upon completion of the reductive amination reaction, the spent catalyst is filtered and the filtrate concentrated to dryness.

The amino compounds produced by the above procedures are isolated by taking advantage of their basic nature which permits convenient separation from non-basic by-products and reactants. In general, an aqueous solution of the product is extracted over a range of gradually increasing pH so that non-basic materials are removed at the lower pH's and the product at a pH of about 9. The extracting solvents, e.g., ethyl acetate, diethyl ether, are back-washed with brine and water, dried and evaporated to give the product.

A further favored procedure comprises reaction of the appropriate compound of formula I or II wherein $R_2$ or $R_3$ is ω-hydroxy substituted alkyl with equimolar quantities of phthalimide, triphenylphosphine and diethylazodicarboxylate.

Compounds of this invention of Formula I wherein R is amino are prepared in like manner from formula I or II compounds. If either of $R_2$ or $R_3$ is oxo-substituted alkyl and introduction of an amino group at the 1-position of the cycloalkyl moiety is desired, said oxo group must be protected as by ketal formation. When amino groups are to be introduced simultaneously into the 1-position of the cycloalkyl moiety and $R_2$ (or $R_3$), the above-described processes are used but, of course, doubling the molar proportions of reactants per mole of oxo-containing reactant.

Mono- and dialkylamino substituted alkyl derivatives ($R_2$, $R_3$) of formulae I and II compounds are prepared by reductive alkylation of the corresponding aminoalkyl derivatives with the appropriate aldehyde or ketone in the presence of a reducing agent such as molecular hydrogen and a catalyst (Pd or Raney nickel) or nascent hydrogen from a metal-acid combination. When mono- or dimethylamino derivatives are desired, the Leuckart reaction, in which formic acid or one of its derivatives, such as ammonium formate, serve as reducing agent, is used.

It has been found that the compound of formula I wherein R is OH; $R_2$ is . . . $(CH_2)_3OH$, —ZW is —$C(CH_3)_2(CH_2)_5CH_3$ and $R_1$ is benzyl $(C_7H_7)$ can be resolved into diastereomers A and B by reaction with d-mandelic acid and p-toluenesulfonic acid in benzene with azeotropic removal of water. Hydrolysis of the bis-d-mandelate esters of diastereomers A and B (e.g., $K_2CO_3$ in methanol-water) affords enantiomers A and B.

In like manner, reaction of enantiomer B with l-mandelic acid and p-toluenesulfonic acid in benzene with azeotropic removal of water affords diastereomer A of the bis-l-mandelate derivative. Hydrolysis as described above affords enantiomer B. Removal of the protecting benzyl groups affords the corresponding enantiomeric alcohols.

Similarly, the benzyl ether of the above-mentioned compound ($R_2$= . . . $(CH_2)_3$—O—$C_7H_7$) is resolved into its diastereomers and enantiomers. Other compounds of formula I herein are also resolved in like manner.

Compounds of formulae I and II wherein $R_2$ and $R_3$ are alkyl substituted with —$SR_6$, —$S(O)R_6$ or —$S(O)_2R_6$ are also active as CNS agents and antiemetics and are used in the same manner as are the formulae I and II compounds described herein. Said compounds wherein the alkyl substituent is —$SR_6$ are prepared from corresponding alcohols via halogenation ($SOCl_2$) and reaction of the thus produced chloride with $HSR_6$ in the presence of a base. Oxidation of the —$SR_6$-substituted alkyl group with one or two equivalents of hydrogen peroxide or a peracid, e.g., m-chlor-perbenzoic acid, affords the corresponding sulfoxide or sulfone.

Acyl derivatives of formulae I and II compounds wherein $R_1$ is hydroxy and any of R, $R_2$ or $R_3$ is hydroxy, amino, or hydroxyalkyl or aminoalkyl are prepared by acylation with the appropriate alkanoic acid in the presence of a condensing agent such as dicyclohexylcarbodiimide, or by reaction with the appropriate alkanoic acid chloride or anhydride in the presence of a base such as pyridine. The order of reactivity of the acylatable R, $R_1$, $R_2$ and $R_3$ groups which are or which contain a hydroxy group is primary alcoholic OH, phenolic OH, secondary OH.

Esters of compounds of formulae I and II wherein R is hydroxy, $OR_1$ is hydroxy and $R_2$ or $R_3$ contain no acylatable group, are prepared by acylation according to the above-described procedures. Compounds in which only the R group is acylated are obtained by mild hydrolysis of the corresponding diacyl derivative, advantage being taken of the greater ease of hydrolysis of the phenolic acyl group.

The analgesic properties of the compounds of this invention are determined by tests using nociceptive stimuli. It is noted that compounds of formulae I and II wherein $R_1$ is benzyl are not pharmacologically active for the purposes described herein but are useful as intermediates for said compounds wherein $R_1$ is hydrogen.

Tests Using Thermal Nociceptive Stimuli (a) Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a ⅛-inch thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½-inch diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an $MPE_{50}$=4–5.6 mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941) using controlled high intensity heat applied to the tail. Each mouse is placed in a snug-fitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPR_{50}$ of 3.2–5.6 mg./kg. (s.c.).

(c) Tail Immersion Procedure

The method is a modification of the receptacle procedure developed by Benbasset, et al., *Arch. int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. MPE$_{50}$'s of the drug pretreatments in blocking writhing are ascertained.

Tests Using Pressure Nociceptive Stimuli

Effect on the Haffner Tail Pinch Procedure

A modification of the procedure of Haffner, *Experimentelle Prufung Schmerzstillender. Deutch Med. Wschr.*, 55, 731–732 (1929) is used to ascertain the effects of the test compound on aggressive attacking responses elicited by a stimulus pinching the tail. Male albino rats (50–60 g.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The endpoint at each trail is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg. (i.p.).

Tests Using Electrical Nociceptive Stimuli

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (%MPE). The %MPE of each group is statistically compared to the %MPE of the standard and the predrug control values. The %MPE is calculated as follows:

$$\% MPE = \frac{\text{test time} - \text{control time}}{\text{cutoff time} - \text{control time}} \times 100$$

The compounds of this invention, when used as analgesics via oral or parenteral administration, are conveniently administered in composition form. Such compositions include a pharmaceutical carrier selected on the basis of the chosen route of administration and standard pharmaceutical practices. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 0.01 to about 100 mg. are suitable for most applications.

By means of the above procedures, the analgesic activity of several compounds of this invention is determined. The compounds have the formula shown below:

TABLE I

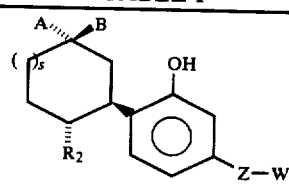

| $R_2$ | A | B | s | Z—W | MPE$_{50}$ (mg./kg.) | | | | |
|---|---|---|---|---|---|---|---|---|---|
| | | | | | PBQ | RTC | HP | TF | FJ |
| CH$_2$OH | H | OH | 1 | C(CH$_3$)$_2$C$_6$H$_{13}$ | 1.71 | 1.26 | | | |
| (CH$_2$)$_2$OH | H | OH | 1 | C(CH$_3$)$_2$C$_6$H$_{13}$ | 2.58 | 7.85 | | | |
| (CH$_2$)$_3$OH | H | OH | 1 | C(CH$_3$)$_2$C$_6$H$_{13}$ | 0.29 | 0.46 | 1.11 | 0.55 | 0.63 |
| (CH$_2$)$_3$OH$^{(a)}$ | H | OH | 1 | C(CH$_3$)$_2$C$_6$H$_{13}$ | 0.06 | 0.13 | 0.66 | 0.41 | |
| (CH$_2$)$_3$OH$^{(b)}$ | H | OH | 1 | C(CH$_3$)$_2$C$_6$H$_{13}$ | 14.6 | | | | |
| (CH$_2$)$_4$OH | H | OH | 1 | C(CH$_3$)$_2$C$_6$H$_{13}$ | 0.23 | 1.15 | | | |
| (CH$_2$)$_5$OH | H | OH | 1 | C(CH$_3$)$_2$C$_6$H$_{13}$ | 0.55 | 2.64 | | | |
| (CH$_2$)$_3$OCH$_3$ | H | OH | 1 | C(CH$_3$)$_2$C$_6$H$_{13}$ | 0.37 | ~1.00 | | | |
| CHO | H | OH | 1 | C(CH$_3$)$_2$C$_6$H$_{13}$ | 2.59 | | | | |
| CH$_2$CHO | H | OH | 1 | C(CH$_3$)$_2$C$_6$H$_{13}$ | 1.21 | | | | |
| CH$_2$COOH | H | OH | 1 | C(CH$_3$)$_2$C$_6$H$_{13}$ | >56 | | | | |
| (CH$_2$)$_2$COOH | H | OH | 1 | C(CH$_3$)$_2$C$_6$H$_{13}$ | ≦56 | | | | |
| (CH$_2$)$_2$COOCH$_3$ | H | OH | 1 | C(CH$_3$)$_2$C$_6$H$_{13}$ | 7.53 | 30.6 | | | |
| (CH$_2$)$_2$CONH$_2$ | H | OH | 1 | C(CH$_3$)$_2$C$_6$H$_{13}$ | ~56 | | | | |
| CH$_2$NH$_2$ | H | OH | 1 | C(CH$_3$)$_2$C$_6$H$_{13}$ | ≦56 | | | | |
| (CH$_2$)$_2$NH$_2$HCl | H | OH | 1 | C(CH$_3$)$_2$C$_6$H$_{13}$ | >56 | | | | |
| CH$_2$N(CH$_3$)$_2$HCl | H | OH | 1 | C(CH$_3$)$_2$C$_6$H$_{13}$ | ~56 | | | | |
| (CH$_2$)$_3$N(CH$_3$)$_2$HCl | H | OH | 1 | C(CH$_3$)$_2$C$_6$H$_{13}$ | 6.38 | | | | |

TABLE I-continued

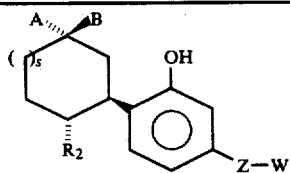

| $R_2$ | A | B | s | Z—W | MPE$_{50}$ (mg./kg.) PBQ | RTC | HP | TF | FJ |
|---|---|---|---|---|---|---|---|---|---|
| $CH_2CHOHCH_3$[c] | H | OH | 1 | $C(CH_3)_2C_6H_{13}$ | 1.00 | | | | |
| $CH_2CHOHCH_3$[d] | H | OH | 1 | $C(CH_3)_2C_6H_{13}$ | 0.77 | | | | |
| $CH_2NH_2$ | OH | H | 1 | $C(CH_3)_2C_6H_{13}$ | ~56 | | | | |
| $CH_2N(CH_3)_2HCl$ | OH | H | 1 | $C(CH_3)_2C_6H_{13}$ | >56 | | | | |
| $(CH_2)_3OH$ | H | H | 1 | $C(CH_3)_2C_6H_{13}$ | 0.93 | | | | |
| $(CH_2)_3OH$ | H | OH | 2 | $C(CH_3)_2C_6H_{13}$ | 0.1 | 0.4 | 7.8 | 1.0 | 1.0 |
| $(CH_2)_3OH$ | OH | H | 2 | $C(CH_3)_2C_6H_{13}$ | 1.11 | | ~32 | 3.56 | |
| $(CH_2)_3OH$[e] | H | OH | 2 | $C(CH_3)_2C_6H_{13}$ | 0.06 | 0.1 | 0.2 | 0.2 | 0.3 |
| $(CH_2)_3OH$[f] | H | OH | 2 | $C(CH_3)_2C_6H_{13}$ | ~10 | | | | |
| $(CH_2)_3OH$ | H | NHAc | 2 | $C(CH_3)_2C_6H_{13}$ | 0.2 | 1.0 | | | |
| $(CH_2)_3OH$ | O | | 2 | $C(CH_3)_2C_6H_{13}$ | 1.20 | ~56 | | | |
| $(CH_2)_3OH$ | O | | 1 | $C(CH_3)_2C_6H_{13}$ | 0.38 | ~1.00 | | | |
| $(CH_2)_3OH$ | H | OH | 1 | $CH_3\diagdown\,^{\backslash\backslash}H$ $-O-C-C_6H_{13}$ | 0.27 | | | | |
| $(CH_2)_3OH$ | OH | H | 1 | | 0.54 | | | | |
| $(CH_2)_3OH$ | H | OH | 1 | $CH_3^{\,\prime\prime}\diagup H$ $-O-C-C_6H_{13}$ | 0.50 | | | | |
| $(CH_2)_3OH$ | OH | H | 1 | | 2.87 | | | | |
| $(CH_2)_3OH$ | H | OH | 2 | $CH_3\diagdown\,^{\backslash\backslash}H$ $-O-C-(CH_2)_3C_6H_5$ | 0.99 | | | | |

[a](−) enantiomer
[b](+) enantiomer
[c]diastereomer A
[d]diastereomer B
[e](−) enantiomer
[f](+) enantiomer

TABLE II

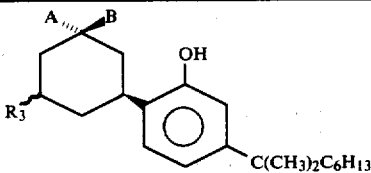

| $R_3$ | A | B | MPE$_{50}$ (mg./kg.) PBQ | RTC |
|---|---|---|---|---|
| HO ▶ | H | OH | 5.6 | |
| HO ⦀ | H | OH | 13.9 | 39.2 |
| HO ⦀ | OH | H | 5.8 | >56 |
| NC ▶ | H | OH | 7.20 | |
| HOCH$_2$ ▶ | H | OH | 1.21 | 3.34 |
| NC ▶ | O | | 2.87 | |

The antiemetic properties of the compounds of formulae I and II are determined in unanesthetized unrestrained cats according to the procedure described in Proc. Soc. Exptl. Biol. and Med., 160, 437–440 (1979).

The compounds of the present invention are active antiemetics via oral and parenteral administration and are conveniently administered in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, dispersions, solutions, emulsions, syrups and elixirs which may contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in adults may range from about 0.1 to about 750 mg. per day in single or divided doses. In many instances, it is not necessary to exceed 100 mg. daily. The favored oral dosage range is from about 1.0 to about 300 mg./day; the preferred dose is from about 1.0 to about 50 mg./day. The favored parenteral dose is from about 0.1 to about 100 mg./day; the preferred range from about 0.1 to about 20 mg./day.

This invention also provides pharmaceutical compositions, including unit dosage forms, valuable for the use of the herein described compounds as analgesics and other utilities disclosed herein. The dosage form can be given in single or multiple doses, as previously noted, to achieve the daily dosage effective for a particular utility.

The compounds (drugs) described herein can be formulated for administration in solid or liquid form for oral or parenteral administration. Capsules containing drugs of this invention are prepared by mixing one part by weight of drug with nine parts of excipient such as starch or milk sugar and then loading the mixture into telescoping gelatin capsules such that each capsule contains 100 parts of the mixture. Tablets containing said compounds are prepared by compounding suitable mixtures of drug and standard ingredients used in preparing tablets, such as starch, binders and lubricants, such that each tablet contains from 0.10 to 100 mg. of drug per tablet.

EXAMPLE 1

Trans-3-[2-Benzyloxy-4-(1,1-dimethylheptyl)phenyl]-4-(2-propenyl)cyclohexanone

A solution of 73.0 g. (0.188 mole) of 1-bromo-2-benzyloxy-4-(1,1-dimethylheptyl)benzene (BrZ') in 350 ml. of tetrahydrofuran was slowly added to 9.0 g. (0.375 mole) of 70–80 mesh magnesium metal. After a 5 minute initiation period the rate of addition was adjusted so as to just maintain reflux. The reaction was stirred 1.5 hours longer following completion of addition while cooling to 25° C. The reaction was cooled to −20° C. and 1.78 g. (9.38 mmoles) of cuprous iodide added. The resultant mixture was stirred 5 minutes and then a solution of 25.5 g. (0.188 mole) of 4-(2-propenyl)-2-cyclohexen-1-one (enone) in 30 ml. of tetrahydrofuran added dropwise while the reaction temperature was maintained at about −18° C. Additional 1.78 g. (9.38 mmoles) portions of cuprous iodide were added following addition of ⅓ and ⅔ of the enone reactant. The reaction was stirred 5 minutes longer at −20° C. and then added to 1000 ml. of ice cold saturated ammonium chloride. The quenched mixture was extracted with 1000 ml. of ether and the organic extract washed twice with 500 ml. of saturated ammonium chloride, once with 500 ml. of saturated sodium chloride, dried over magnesium sulfate and evaporated (aspirator) to an oil. The crude oil was purified via column chromatography on 1 kg. of silica gel eluted with 20% etherhexane to yield 58.3 g. (70%) of the title compound as an oil.

IR (CHCl$_3$) 1712, 1645, 1613 and 1575 cm$^{-1}$.
MS (m/e) 446 (M+), 360, 354 and 91.
PMR $\delta_{CDCl_3}^{TMS}$ 0.82 (m, terminal methyl), 1.23 (s, gem dimethyl), 4.7–5.1 (m, vinyl H), 5.02 (s, benzylic methine), 5.3–6.1 (m, vinyl H), 6.79 (d, J=2 Hz, ArH), 6.82 (dd, J=8 and 2 Hz, ArH) and 7.0 (d, J=8 Hz, ArH).

In like manner the following compounds were prepared from the appropriate 4-(R$_2$-substituted-2-cycloalken-1-one (enone) in place of the enone used above and proportionate amounts of magnesium metal, cuprous iodide and 1-bromo-2-benzyloxy-4-(1,1-dimethylheptyl)benzene (BrR°):

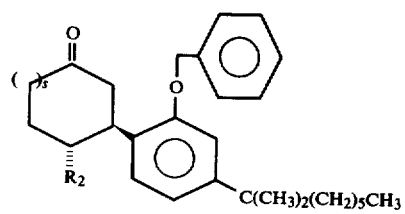

| R$_2$ | s | Gm. Reactants Enone | BrR° | Yield | IR(CHCl$_3$) Cm$^{-1}$ | MS(m/e) | PMR $\delta_{CDCl_3}^{TMS}$ |
|---|---|---|---|---|---|---|---|
| (CH$_2$)$_2$CH=CH | 1 | 5.98 (39.9 mM) | 15.4 (39.6 mM) | 11.0 g. (60%) an oil | 1715, 1650, 1618, 1577 | 460 (M+) 375, 369 | 0.81 (m, terminal methyl, 1.21 (s, gem dimethyl), 4.5–5.0 and 5.1–5.6 (m, vinyl H), 5.01 (s, benzylic methylene), 6.79 (d, J = 2Hz, ArH), 6.79 (dd, J = 8 and 2Hz, ArH), 7.00 (d, J = 8Hz, ArH) and 7.30 (s, PhH) |
| CH$_2$CH=CH$_2$ | 2 | 12.7 (84.4 mM) | 50.4 (126 mM) | 25.3 g. (66%) an oil | 1702, 1650, 1618, 1580 | 454 (M+) 91 | 0.80 (m, terminal methyl), 1.21 (s, gem dimethyl), 4.6–5.0 and 5.1–5.9 (m, vinyl H), 5.00 (s, benzylic methylene), 6.85 (m, ArH), 7.00 (d, J = 8Hz, ArH) and 7.36 (bs, PhH) |
| CH(OCH$_3$)$_2$ | 1 | 10.0 (58.8 mM) | 22.9 (58.8 mM) | 14.1 g. (50%) an oil | 1721, 1626, 1584 | 480 (M+) 413, 353, 329, 323, 319, 91 | 0.85 (m, terminal methyl), 1.30 (s, gem dimethyl), 3.25 and 3.26 (s, methoxys), 3.38 (m, methine), 3.96 (d, J = 2Hz, ketal methine), 5.10 (s, benzylic methylene), 6.9 (m, ArH), 7.10 (d, J = 8Hz, ArH) and 7.42 (bs, PhH) |
| (CH$_2$)$_3$—O—CH$_2$C$_6$H$_5$ | 1 | 11.0 (45.5 mM) | 35.0 (90.0 mM) | 12.3 g. (50%) an oil | 1709, 1600, 1568 | 554.3730 (M+) 463, 445, 373, 355, 337, 319, 91 (a) | 0.83 (m, terminal methyl), 1.26 (s, gem dimethyl), 1.8–2.8 and 2.8–3.5 (m), 4.40 and 5.08 (s, benzylic methylenes), 6.9 (m, ArH), 7.07 (d, J = 8Hz, ArH), 7.30 and 7.38 (s, PhH) |

(a) HRMS (m/e): M+ calc'd for C$_{38}$H$_{50}$O$_3$: 554.3747

EXAMPLE 2

Cis-3-[2-Benzyloxy-4-(1,1-dimethylheptyl)phenyl]-trans-4-(2-propenyl)cyclohexanol and the trans, cis isomer To a 0° C. solution of 14.3 g. (32.1 mmoles) of trans-3-[2-benzyloxy-4-(1,1-dimethylheptyl)phenyl]-4-(2-propenyl)cyclohexanone in 50 ml. of methanol was added 1.22 g. (32.1 mmoles) of sodium borohydride. The reaction was stirred 30 minutes at 0° C. and then added to 500 ml. saturated sodium chloride and 300 ml. ether. The organic extract was washed twice with 500 ml. saturated sodium chloride, dried over magnesium sulfate and evaporated (aspirator) to an oil. The crude oil was purified via column chromatography on 200 g. of silica gel eluted with 2:1 pentane:ether to yield in order of elution 1.9 g. (13%) of the trans, cis-isomer of the title compound as an oil, 2.7 g. (19%) of a mixture of isomers and 7.3 g. (51%) of the title compound as an oil.

Cis-3, trans-4 isomer:
IR (CHCl$_3$) 3571, 3401, 1639, 1610 and 1572 cm$^{-1}$.
MS (m/e) 448 (M+), 406, 363 and 91.
PMR $\delta_{CDCl_3}^{TMS}$ 0.82 (m, terminal methyl), 1.22 (s, gem dimethyl), 2.90 (m, benzylic methine), 3.73 (m, carbinol methine), 4.6–5.1 (m, vinyl H), 5.02 (s, benzylic methylene), 5.3–6.3 (m, vinyl H), 6.75 (d, J=2 Hz, ArH), 6.75 (dd, J=8 and 2 Hz, ArH), 6.99 (d, J=8 Hz, ArH) and 7.25 (bs, Ph).

Trans-3, cis-4 isomer:
IR (CHCl$_3$) 3559, 3401, 1639, 1608 and 1567 cm$^{-1}$.
MS (m/e) 448 (M+), 433, 430, 363, 406 and 91.
PMR $\delta_{CDCl_3}^{TMS}$ 0.82 (m, terminal methyl), 1.25 (s, gem dimethyl), 3.30 (m, benzylic methine), 4.12 (m, carbinol methine), 4.6–5.0 (m, vinyl H), 5.06 (s, benzylic methylene), 5.2–6.1 (m, vinyl H), 6.82 (d, J=2 Hz, ArH), 6.82 (dd, J=8 and 2 Hz, ArH), 7.07 (d, J=8 Hz, ArH) and 7.38 (bs, Ph).

Following the above procedure, the compounds tabulated below were prepared from appropriate 3-[2-benzyloxy-4-(1,1-dimethylheptyl)phenyl]-4-(2-R$_2$-substituted)cycloalkanones and stoichiometric amounts of sodium borohydride, i.e., one gram atom/oxo group present:

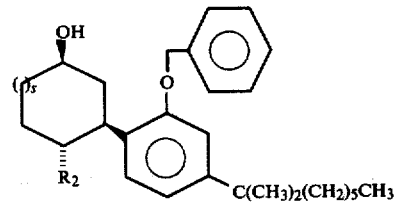

In the table, R° represents the 3-[2-benzyloxy-4-(1,1-dimethylheptyl)phenyl] moiety.

| s | R$_2$ | R° | Gms. | R° | R$_2$ | Yield | IR (CHCl$_3$) cm$^{-1}$ | MS(m/e) | PMR $\delta_{CDCl_3}^{TMS}$ |
|---|---|---|---|---|---|---|---|---|---|
| 1 | (CH$_2$)$_2$CH=CH$_2$ | trans | 5.5 (12mM) | trans | cis | 0.9 g. (16%) an oil | 3413, 1658, 1626, 1585 | 462(M+), 377, 353, 91 | 0.8 (m, terminal methyl), 1.20 (s, gem dimethyl), 3.2 (m, benzylic methine), 4.09 (m, carbinol methine), 4.6–5.0 and 5.1–6.0 (m, terminal olefin), 5.05 (s, benzylic methylene), 6.82 (d, J = 2, ArH), 6.82 (dd, J = 8 and 2Hz, ArH), 7.07 (d, J = 8Hz, ArH) and 7.38 (m, PhH). |
|   |   |   |   | cis | trans | 2.9 g. (52%) an oil | 3367, 1656, 1623, 1582 | 462(M+), 377, 91 | 0.81 (m, terminal methyl), 1.21 (s, gem dimethyl), 2.85 (m, benzylic methine), 3.60 (m, carbinol methine), 4.5–5.0 and 5.1–6.0 (m, terminal olefin), 5.00 (s, benzylic methylene), 6.80 (m, ArH), 6.99 (d, J = 8Hz, ArH) and 7.30 (bs, PhH). |
| 1 | (CH$_2$)$_4$CHO | trans | 0.400 (0.816 mM) | cis | trans (CH$_2$)$_5$OH | 0.335 g. (84%) an oil |   |   | 0.82 (m, terminal methyl), 1.22 (s, gem dimethyl), 2.85 (m, benzylic methine), 3.50 (t, J = 7Hz, alcohol methylene), 3.55 (m, carbinol methine), 5.05 (s, benzylic methine), 6.85 (m, ArH), 7.02 (d, J = 8Hz, ArH) and 7.32 (bs, PhH). |
| 1 | CH$_2$CH$_2$OH | trans | 0.900 (2.01 | trans | cis | 0.130 g. (14%) | 3571, 3425, | 452(M+), 432, 367, |   |

-continued

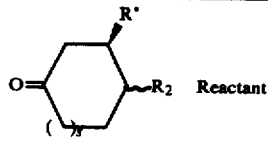 Reactant

| s | $R_2$ | R* Gms. (mM) | R* | $R_2$ | Yield | Product IR (CHCl₃) cm⁻¹ | MS(m/e) | PMR $\delta_{CDCl_3}^{TMS}$ |
|---|---|---|---|---|---|---|---|---|
| | | | cis | trans | 0.770 g. (85%) an oil | 1613, 1575 3636, 3472, 1623, 1580 | 359, 344, 343, 300, 259, 91 452(M+), 432, 367, 359, 349, 343, 259, 91 | |
| 1 | CH₂—CH—CH₃ <br> OH | trans 0.621 (1.33 mM) Diastereomer A | trans | cis | 0.096 g. (15%) an oil | | 466(M+), 451, 448, 381, 358, 91 | |
| | | | cis | trans | 0.425 g. (69%) an oil | 3623, 1618, 1580 | 466(M+), 451, 448, 381, 358, 274, 214, 91 | |
| | | trans 0.895 (1.92 mM) Diastereomer B | trans | cis | 0.079 g. (9%) an oil | | 466(M+), 451, 448, 381, 358, 273, 213, 91 | |
| | | | cis | trans | 0.555 g. (62%) an oil | 3636, 3484, 1626, 1582 | 466(M+), 451, 448, 381, 91 | |
| 1 | CH(OCH₃)₂ | trans 35.6 (73.7 mM) | cis | trans | 14.4 g. (40%) an oil | 3521, 3389, 1600, 1562 | 482(M+), 396, 359, 341, 327, 311, 91 | 0.86 (m, terminal methyl), 1.28 (s, gem dimethyl), 2.86 and 2.90 (s, methoxys), 3.75 (m, carbinol methine), 3.65 (d, J = 2Hz, ketal methine), 5.10 (s, benzylic methylene), 6.85 (m, ArH), 7.09 (d, J = 8Hz, ArH) and 7.40 (bs, PhH). |
| | | | | | plus mixture of cis-trans and trans-cis isomers | | | |
| 1 | (CH₂)₃—O—CH₂C₆H₅ | trans 12.3 (50.4 mM) | trans | cis | 1.1 g. (9%) an oil | | 556.3955 (M+), 448, 363, 358, 273, 91 (a) | 6.3 g. (18%) 0.82 (m, terminal methyl), 1.26 (s, gem dimethyl), 3.50 (bt, J = 7Hz, methylene), 4.10 (m, carbinol methine), 4.40 and 5.05 (s, benzylic methylenes), 6.84 (m, ArH), 7.05 (d, J = 8Hz, ArH), 7.28 (s, PhH) and 7.38 (m, PhH). |
| | | | cis | trans | 10.4 g. (85%) an oil | | 556.3910 (M+), 505, 448, 357, 273, 91 (a) | 0.82 (m, terminal methyl), 1.25 (s, gem dimethyl), 2.8 (m, benzylic methine), 3.25 (bt, J = 6Hz, methylene), 3.65 (m, carbinol methine), 4.38 and 5.07 (s, benzylic methylenes), 6.82 (d, J = 2Hz, ArH), 6.82 (dd, J = 8 and 2Hz, ArH), 7.02 (d, J = 8Hz, ArH), 7.23 (s, PhH) and |

| | | | | | | | Product | | |
|---|---|---|---|---|---|---|---|---|---|
| s | $R_2$ | R° | Gms. | R° | $R_2$ | Yield | IR (CHCl₃) cm⁻¹ | MS(m/e) | PMR $\delta_{CDCl_3}^{TMS}$ |
| | | | | | | | | | 7.35 (bs, PhH). |

(a) HRMS (m/e): M⁺ calc'd. for $C_{38}H_{52}O_3$: 556.3903

EXAMPLE 3

Cis-3-[2-Benzyloxy-4-(1,1-dimethylheptyl)phenyl]-trans-4-hydroxymethylcyclohexanol Using the procedure of Example 2, 1.0 g. (2.29 mmole) of cis-3-[2-benzyloxy-4-(1,1-dimethylheptyl)-phenyl)trans-4-oxomethylcyclohexanol is reduced to give a quantitative yield of the title compound as an oil.

IR (CHCl₃) 3400, 1605 and 1562 cm⁻¹.

MS (m/e) 438 (M+), 420, 353, 330, 312, 299 and 91.

PMR $\delta_{CDCl_3}^{TMS}$ 0.82 (m, terminal methyl), 1.23 (s, gem dimethyl), 3.25 (m, hydroxymethylene), 3.65 (m, carbinol methine), 5.08 (s, benzylic methylene), 6.90 (m, ArH), 7.12 (d, J=8 Hz, ArH) and 7.39 (s, Ph).

EXAMPLE 4

Trans-3-[2-Benzyloxy-4-(1,1-dimethylheptyl)phenyl]-4-(2-hydroxyethyl)cyclohexanone ethylene ketal Using the procedure of Example 2, 1.00 g. (2.03 mmole) of trans-3-[2-benzyloxy-4-(1,1-dimethylheptyl)-phenyl]-4-(2-oxoethyl)cyclohexanone ethylene ketal is reduced to give a quantitative yield of the title compound as an oil.

PMR $\delta_{CDCl_3}^{TMS}$ 0.82 (m, terminal methyl), 1.11 (s, gem dimethyl), 3.50 (bt, J=6 Hz, alcohol methylene), 3.91 (s, ethylene), 5.02 (s, benzylic methylene), 6.8–7.1 (m, ArH) and 7.33 (m, PhH).

EXAMPLE 5

Cis-3-[2-Benzyloxy-4-(1,1-dimethylheptyl)phenyl]-trans-4-(3-hydroxypropyl)cyclohexanol To a mechanically stirred, 0° C. solution of 2.0 g. (4.46 mmoles) of cis-3-[2-benzyloxy-4-(1,1-dimethylheptyl)phenyl]-trans-4-(2-propenyl)cyclohexanol in 20 ml. of tetrahydrofuran was added 9 ml. (8.92 mmoles) of boran tetrahydrofuran complex (1 M in tetrahydrofuran). The reaction was allowed to warm to 25° C. and was then stirred for 30 minutes at 25° C. The reaction was cooled to 0° C. and oxidized by the addition of 1 ml. water, 2.66 ml. (5.34 mmoles) of 2 N sodium hydroxide and 0.92 ml. (10.7 mmoles) of 30% hydrogen peroxide. The reaction was allowed to warm to 25° C., stirred for 35 minutes, and added to 200 ml. saturated sodium chloride and 200 ml. ether. The ether extract was washed twice with 100 ml. of saturated sodium chloride, dried over magnesium sulfate and evaporated (aspirator) to an oil. The crude oil was purified via column chromatography on 40 g. of silica gel, eluted with ether to yield 2.0 g. (96%) of the title compound as an oil.

IR (CHCl₃) 3623, 3425, 1623 and 1580 cm⁻¹.

MS (m/e) 466 (M+), 448, 381, 363, 358, 357 and 91.

PMR $\delta_{CDCl_3}^{TMS}$ 0.82 (m, terminal methyl), 1.24 (s, gem dimethyl), 2.90 (m, benzylic methine), 3.2–3.9 (m, carbinol methine and methylene), 5.08 (s, benzylic methylene), 6.86 (d, J=2 Hz, ArH), 6.86 (dd, J=8 and 2 Hz, ArH) and 7.05 (d, J=8 Hz, ArH).

In like manner the following compounds are prepared from appropriate reactants.

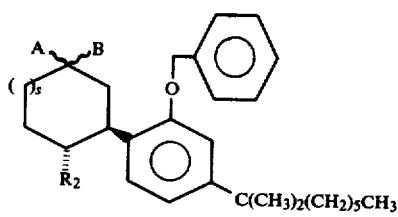

| s | A⋎B R₂ | | Gms. | R₂ | Yield | IR (CHCl₃) cm⁻¹ | MS(m/e) | PMR $\delta_{CDCl_3}^{TMS}$ |
|---|---|---|---|---|---|---|---|---|
| 1 | O⌒O | CH₂—CH=CH₂ | 16.2 (33.1 mM) | CH₂CH₂CH₂OH | Quantitative an oil | | | 0.86 (m, terminal methyl), 1.26 (s, gem dimethyl), 3.08 (m, benzylic methine), 3.47 (t, J = 7Hz, alcohol methylene), 3.93 (s, ethylene), 5.10 (s, benzylic methylene), 6.90 (m, ArH), 7.08 (d, J = 8Hz, ArH) and 7.42 (m, PhH). |
| 2 | O⌒O | CH₂—CH=CH₂ | 4.70 (9.32 mM) | CH₂CH₂CH₂OH | Quantitative an oil | 3509, 1613, 1577, 1502, 1466 | 522(M⁺) | 0.83 (m, terminal methyl), 1.23 (s, gem dimethyl), 2.9-3.7 (m, alcohol methylene and benzylic methine), 3.82 (bs, ethylene), 5.06 (benzylic methylene), 6.85 (m, ArH), 7.02 (d, J = 8Hz, ArH) and 7.38 (m, PhH). |
| 1 | H⋎OH | (CH₂)₂CH=CH₂ | 3.3 (7.14 mM) | (CH₂)₃CH₂OH | 2.3 g. (67%) an oil | 3448, 1623, 1580 | 480(M⁺), 462, 395, 91 | |
| 2 | H⋎OH | CH₂CH=CH₂ | 1.0 (2.16 mM) | CH₂CH₂CH₂OH | 1.0 g. (97%) an oil | | | 0.9 (m, terminal methyl), 1.28 (s, gem dimethyl), 3.48 (m, alcohol methylene), 3.70 (m, carbinol methine), 5.02 (s, benzylic methylene) 6.90 (m, ArH) and 7.38 (bs, PhH). |
| 2 | H⋎OH | CH₂—CH=CH₂ | 5.0 (10.8 mM) | CH₂CH₂CH₂OH | 4.2 g. (82%) an oil | | | 0.80 (m, terminal methyl), 1.20 (s, gem dimethyl), 3.36 (m, alcohol methylene), 4.02 (m, carbinol methine), 5.07 (s, benzylic methylene) 6.85 (m, ArH), 7.06 (d, J = 8Hz, ArH) and 7.38 (s, PhH). |

-continued

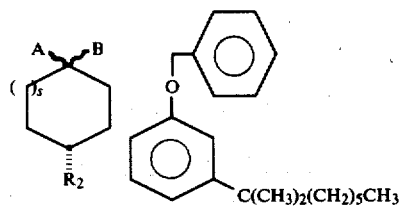

| s | A⤸B (Reactant) | R₂ | Gms. | R₂ (Product) | Yield | IR (CHCl₃) cm⁻¹ | MS(m/e) | PMR δ$_{CDCl_3}^{TMS}$ |
|---|---|---|---|---|---|---|---|---|
| 2 | H⤸OH (Enantiomer A) | CH₂CH=CH₂ | 0.874 (1.89 mM) | CH₂CH₂CH₂OH | 0.778 g. (86%) an oil | | 480.3561 (M⁺), 395, 377, 372, 371, 287, 233, 91 (a) (b) | |
| 2 | H⤸OH (Enantiomer B) | CH₂CH=CH₂ | 0.829 (1.79 mM) | CH₂CH₂CH₂OH | 0.686 g. (80%) an oil | | 480.3565 (M⁺), 395, 377, 372, 371, 287, 233, 91 (a) | |
| 1 | H⤸OC₇H₇ | CH₂—CH=CH₂ | | CH₂CH₂CH₂OH | 2.09 g. (97%) an oil | 3571, 3389, 1600, 1562 | 556.3865 (M⁺), 540, 471, 455, 358, 357, 273, 272, 257, 91 (c) | 1.22 (s, gem dimethyl), 2.78 (m, benzylic methine), 3.2-4.0 (m), 4.61 and 5.12 (s, benzylic methylene), 6.9 (m, ArH) and 7.35 (m, PhH). |

(a) High resolution mass spectral (HRMS); M⁺ calcd. for C₃₂H₄₈O₃ = 480.3597
(b) [α]$_D^{CH_3OH, 25° C}$ = −20.57°
(c) HRMS: M⁺ calcd. for C₃₈H₅₂O₃ = 556.3903

EXAMPLE 6

Cis-3-[4-(1,1-Dimethylheptyl)-2-hydroxyphenyl]trans-4-(3-hydroxypropyl)cyclohexanol A mixture of 2.0 g. (4.29 mmole) of cis-3-[2-benzyloxy-4-(1,1-dimethylheptyl)phenyl]-trans-4-(3-hydroxypropyl)cyclohexanol and 300 mg. of 5% Pd/C/50% water in 10 ml. of ethanol was stirred under 1 atmosphere of hydrogen gas for 45 minutes at room temperature. The reaction was filtered through diatomaceous earth and the filtrate evaporated under reduced pressure to a solid. Recrystallization of the crude solid product from diisopropyl ether gave 1.41 g. (94%) of the title compound.

m.p.: 132°-3° C. (diisopropyl ether).
IR (KBr) 3448, 3226, 1626 and 1592 cm⁻¹.
MS (m/e) 376 (M⁺), 358, 304, 291 and 273.
PMR (CDCl₃, D₂O, D₆-DMSO) δ0.83 (m, terminal methyl), 1.23 (s, gem dimethyl), 3.39 (t, J=6 Hz, carbinol methylene), 3.64 (m, carbinol methine), 6.85 (m, ArH) and 6.91 (d, J=8 Hz, ArH).
Analysis: Calc'd. for C₂₄H₄₀O₃: C, 76.55; H, 10.71. Found: C, 76.55; H, 10.44.

Similarly, the following compounds are prepared from appropriate benzyl ether reactants:

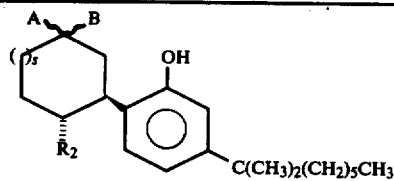

(The value of R₂ is the same in reactant and product).

| | Reactant | | | Product | | | |
|---|---|---|---|---|---|---|---|
| s | A⌒B | R₂ | Gms. | Yield | IR (CHCl₃) cm⁻¹ | MS (m/e) | PMR $\delta_{CDCl_3}^{TMS}$ |
| 1 | O⌒O (dioxolane) | CH₂CH₂CH₂OH | 16.8 (33.1 mM) | 11.0 g. (80%) an oil | 3509, 3279, 1613, 1567 | 418(M⁺), 356, 333, 332, 317, 291, 271 | 0.82 (m, terminal methyl), 1.27 (s, gem dimethyl), 2.87 (m, benzylic methine), 3.50 (t, J = 6Hz, alcohol methylene), 4.00 (s, ethylene), 6.8 (m, ArH) and 7.02 (d, J = 8Hz, ArH). |
| 1 | H⌒OH | CH₂OH | 0.890 (2.03 mM) | 0.370 g. (52%) mp: 137–138° C. (ether/pentane) | 3333, 3195, 1612, 1577 (KBr pellet) | 348(M⁺), 330, 312, 263, 245 | 0.80 (m, terminal methyl), 1.21 (s, gem dimethyl), 3.35 (m, hydroxy methylene), 3.82 (m, carbinol methine), 6.83 (m, ArH) and 7.08 (d, J = 8Hz, ArH). (CDCl₃ + D₆—DMSO) |
| 1 | H⌒OH | CH₂CH₂OH | 0.750 (1.66 mM) | 0.487 g. (81%) mp: 50–55° C. (semisolid from pentane) | 3636, 3356, 1631, 1587, 1577 | 362(M⁺), 344, 300, 290, 277, 259 | 0.85 (m, terminal methyl), 1.28 (s, gem dimethyl), 2.80 (m, benzylic methine), 3.60 (t, J = 6Hz, alcohol methylene), 3.8 (m, carbinol methine), 6.80 (m, ArH) and 7.08 (d, J = 8Hz, ArH). |
| 1 | H⌒OH | (CH₂)₃CH₂OH | 2.3 (4.79 mM) | 1.4 g. (75%) mp: 125–128° C. (petroleum ether) | 3390, 3247, 1634, 1597 (KBr pellet) | | 0.8 (m, terminal methyl), 1.23 (s, gem dimethyl), 2.80 (m, benzylic methine), 3.2–4.0 (m, alcohol methylene and methine), 6.70 (m, ArH) and 6.92 (d, J = 8Hz, ArH). |
| 1 | H⌒OH | (CH₂)₄CH₂OH | 0.335 (0.679 mM) | 0.164 g. (60%) mp: 133–135° C. (pentane) | | 404(M⁺) | 0.83 (m, terminal methyl), 3.50 (t, J = 6Hz, alcohol methylene), 3.65 (m, carbinol methine), 6.85 (m, ArH) and 7.08 (d, J = 8Hz, ArH). (CDCl₃ + D₆—DMSO) |
| 1 | H⌒OH | CH₂CHCH₃<br>\|<br>OH<br>Diastereomer A | 0.400 (0.858 mM) | 0.290 g. (88%) an oil | 3571, 3333, 1613, 1577 | 376.2946 (M⁺) (a) | |
| 1 | H⌒OH | CH₂CHCH₃<br>\|<br>OH<br>Diasteriomer B | 0.552 (1.12 mM) | 0.291 g. (69%) mp: 139–140° C. (methylene chloride-petroleum ether) | 3534, 3268, 1613, 1563 | 376.2987 (M⁺) (a) | |
| 1 | H⌒OH | CH₂CHO | 0.432 (0.960 mM) | Quantitative an oil | 3571, 3333, 1724, 1623, 1582 | 360(M⁺), 342, 332, 316, 314, 298, 275, 273, 257, 247, 239, 231, 213 | 0.82 (m, terminal methyl), 1.22 (s, gem dimethyl), 2.72 (m, benzylic methine), 3.70 (m, carbinol methine), 5.60 (bs, OH), 6.65 (d, J = 2Hz, ArH), 6.80 (dd, J = 8 and 2Hz, ArH), 7.02 (d, J = 8Hz, ArH) and 9.50 (t, J = 2Hz, CHO). |
| 1 | H⌒OH | CH₂—C—CH₂OH<br>‖<br>O | 0.400 (0.833 mM) | 0.313 g. (97%) a foam | 3623, 3378, 1724, 1626, 1578 | 390(M⁺), 372, 359, 316, 305, 298, 287, 273, 231, 213 | 0.87 (m, terminal methyl), 1.25 (s, gem dimethyl), 2.75 (m, benzylic methine), 3.70 (m, carbinol methine), 4.00 (s, hydroxy methylene), 6,80 (m, ArH) and 7.08 (d, J = 8Hz, ArH). |

-continued

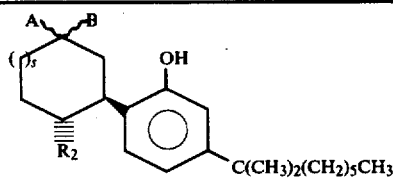

(The value of $R_2$ is the same in reactant and product).

| | Reactant | | | | Product | | |
|---|---|---|---|---|---|---|---|
| s | A⌒B | $R_2$ | Gms. | Yield | IR (CHCl$_3$) cm$^{-1}$ | MS (m/e) | PMR $\delta^{TMS}_{CDCl_3}$ |
| 1 | H ∨ OH | CH$_2$COOH | 0.120 (0.257 mM) | 0.093 g. (97%) mp: 85–87° C. (ether) | | 376.2608 (M$^+$), 358, 291, 273, 213 (b) | 0.83 (m, terminal methyl), 1.24 (s, gem dimethyl), 2.88 (m, benzylic methine), 3.70 (m, carbinol methine), 6.76 (m, ArH) and 7.04 (d, J = 8Hz, ArH). (CDCl$_3$ + D$_6$—DMSO) |
| 2 | =O | CH$_2$CH$_2$CH$_2$OH | 0.960 (2.01 mM) | 0.550 g. (71%) an oil | 3571, 3333, 1701, 1626, 1577 | 388.3011 (M$^+$), 370, 329, 303, 285, 273, 233, 203, 161, 148, 147, 137, 135 (c) | 0.82 (m, terminal methyl), 1.20 (s, gem dimethyl), 3.70 (m, alcohol methylene), 6.78 (m, ArH) and 6.98 (d, J = 8Hz, ArH). |
| 2 | H ∨ OH | CH$_2$CH$_2$CH$_2$OH | 4.7 (9.79 mM) | 0.50 g. (13%) mp: 114–116° C. (pentane) | 3534, 3311, 1610, 1575 | 390.3136 (M$^+$), 372, 329, 305, 287, 257, 246, 233, 161, 147 (d) | 0.82 (m, terminal methyl), 2.65 (m, benzylic methine), 3.40 (m, alcohol methylene), 3.85 (m, carbinol methine), 6.15 (bs, OH), 6.75 (m, ArH) and 6.98 (d, J = 8Hz, ArH). |
| 2 | H ∨ OH | CH$_2$CH$_2$CH$_2$OH | 4.2 (8.75 mM) | 1.49 g. (44%) mp: 57–60° C. (pentane) | 3333, 1626, 1603, 1572 | 390.3132 (M$^+$), 372, 305, 287, 257, 233, 161, 147, 135 (d) | 0.80 (m, terminal methyl), 1.22 (s, gem dimethyl), 3.20 (m, benzylic methine), 3.50 (m, alcohol methylene), 4.22 (m, carbinol methine), 6.7–7.2 (m, ArH). |
| 2 | H ∨ OH | CH$_2$CH$_2$CH$_2$OH Enantiomer A | 0.778 (1.62 mM) | 0.466 g. (74%) mp: 90–92° C. (pentane) | | 390.3130 (M$^+$), 372, 305, 287, 257, 233, 161, 147 (d), (e) | |
| 2 | H ∨ OH | CH$_2$CH$_2$CH$_2$OH Enantiomer B | 0.686 (1.43 mM) | 0.447 g. (80%) an oil | | 390.3095 (M$^+$), 372, 305, 287, 257, 233, 161, 147 (d), (f) | |
| 1 | H ∨ OH | CHO | 1.00 (2.29 mM) | 0.385 g. (49%) mp: 100–102° C. (ether, pentane) | 3508, 3322, 1612, 1562 (g) | 346.2540 (M$^+$), 328, 261, 243 (i) | 0.82 (m, terminal methyl), 1.24 (s, gem dimethyl), 3.8 (m, carbinol methine), 5.0–5.5 (two m, hemiketal methine) and 6.8–7.2 (m, ArH). |
| 1 | H ∨ OH | CH=NOH | 0.500 (1.11 mM) | 0.362 g. (91%) a solid glass | 3533, 3279, 1612, 1562 (g) | 361(M$^+$), 343, 328, 311, 361.2612 (M$^+$) (h) | 0.83 (m, terminal methyl), 1.25 (s, gem dimethyl), 6.85 (m, ArH) and 7.06 (d, J = 8Hz, ArH). |
| 1 | H ∨ OH | CH=NOH | 1.80 (3.99 mM) | 1.28 g. (89%) a solid glass | 3508, 3257, 1613, 1562 (g) | 361(M$^+$), 345, 343, 328, 311, 258 | 0.82 (m, terminal methyl), 1.22 (s, gem dimethyl), 4.23 (m, carbinol methine), 6.85 (m, ArH) and 7.08 (d, J = 8Hz, ArH). |
| 1 | H ∨ OH | CH$_2$CH$_2$CH$_2$OH | 0.500 (0.847 mM) | 0.197 g. (58%) mp: 72–74° C. (pentane) | | 390.3100 (M$^+$), 372, 286, 272, 147 (j) | 0.85 (m), 1.22 (s, gem dimethyl), 3.20 (OCH$_3$), 2.4–4.2 (several m), 5.05 (bs, OH), 6.8 (m, ArH), 7.02 (d, J = 8Hz, ArH). |

-continued

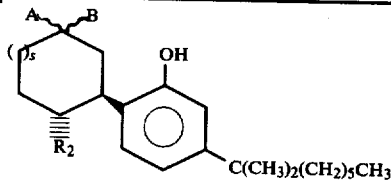

(The value of R₂ is the same in reactant and product).

| Reactant | | | | Product | | |
|---|---|---|---|---|---|---|
| s | A͜B | R₂ | Gms. | Yield | IR (CHCl₃) cm⁻¹ | MS (m/e) | PMR $\delta_{CDCl_3}^{TMS}$ |
| 1 | H͜OH | $(CH_2)_3-O-CH_2C_6H_5$ (k) | 3.00 (5.40 mM) | Quantitative | 3448, 3226, 1626, 1592 | 376(M⁺), 358, 304, 291, 273 | |

(a) HRMS (M⁺) Calc'd. for $C_{24}H_{40}O_3$: 376.2967
(b) HRMS, (M⁺) Calc'd. for $C_{23}H_{36}O_4$: 376.2613
(c) HRMS, (M⁺) Calc'd. for $C_{25}H_{40}O_3$: 388.2973
(d) HRMS, (M⁺) Calc'd. for $C_{25}H_{42}O_3$: 390.3129
(e) $[\alpha]_D^{CH3OH, 25°C} = -24.13°$
(f) $[\alpha]_D^{CH3OH, 25°C} = +23.83°$
(g) Spectral data shows product exists largely in the tautomeric form but acts chemically as the product reported in the table.
(h) HRMS, (M⁺) Calc'd. for $C_{22}H_{35}NO_3$: 361.2608
(i) HRMS, (M⁺) Calc'd. for $C_{22}H_{34}O_3$: 346.2499
(j) HRMS, (M⁺) Calc'd. for $C_{25}H_{42}O_3$: 390.3123
(k) Reactant = cis-(3-[2-benzyloxy-4-[(1,1-dimethylheptyl)phenyl]-trans-4-(3-benzyloxypropyl)cyclohexanol, enantiomer A of Example 38. R₂ is, of course, debenzylated to $(CH_2)_3OH$.

EXAMPLE 7

Trans-3-[2-Benzyloxy-4-(1,1-dimethylheptyl)phenyl]-4-(2-propenyl)cyclohexanone ethylene ketal A mixture of 17.0 g. (38.1 mmoles) of trans-3-[2-benzyloxy-4-(1,1-dimethylheptyl)phenyl]-4-(2-propenyl)-cyclohexanone, 47.2 g. (0.762 mole) ethylene glycol and 250 mg. of p-toluenesulfonic acid monohydride in 200 ml. of benzene was heated at reflux for 3 hours with a Dean-Stark trap. The reaction was cooled and added to 200 ml. 1 N sodium hydroxide, 100 ml. ether and 100 ml. pentane. The organic extract was washed twice with 200 ml. portions of water, twice with 200 ml. portions of saturated sodium chloride, dried over magnesium sulfate and evaporated (aspirator) giving a quantitative yield of the title compound.

IR (CHCl₃) 1656, 1626 and 1587 cm⁻¹.
MS (m/e) 490 (M⁺), 475, 450, 449, 448, 446, 407, 405, 399, 383 and 91.
PMR $\delta_{CDCl_3}^{TMS}$ 0.82 (m, terminal methyl), 1.22 (s, gem dimethyl), 3.1 (m, benzylic methine), 3.90 (s, ethylene ketal), 4.6–5.0 and 5.2–6.0 (m, vinyl H), 5.07 (s, benzylic methylene), 6.81 (d, J=2 Hz, ArH), 6.81 (dd, J=8 and 2 Hz, ArH) and 7.02 (d, J=8 Hz, ArH).

In like manner, 4.5 g. (9.8 mmole) of trans-3-[2-benzyloxy-4-(1,1-dimethylheptyl)phenyl]-4-(2-propenyl)-cyclopentanone is converted in quantitative yield to trans-3-[2-benzyloxy-4-(1,1-dimethylheptyl)phenyl]-4-(2-propenyl)cycloheptanone ethylene ketal, an oil.

IR (CHCl₃) 1650, 1613, 1550, 1504 and 1460 cm⁻¹.
MS (m/e) 504 (M⁺)
PMR $\delta_{CDCl_3}^{TMS}$ 0.80 (m, terminal methyl), 1.22 (s, gem dimethyl), 3.20 (m, benzylic methine), 3.80 (bs, ethylene), 4.6–6.0 (m, olefinic), 5.07 (s, benzylic methylene), 6.85 (m, ArH), 7.02 (d, J=8 Hz, ArH) and 7.38 (m, PhH).

The following compounds are prepared from appropriate cycloalkanone reactants in like manner:

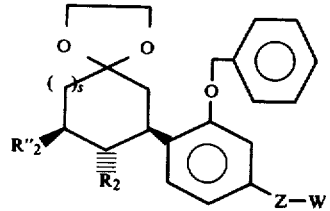

| s | R₂ | R″₂ | Z—W |
|---|---|---|---|
| 1 | —CH₂—CH=CH₂ | CH₃ | C(CH₃)₂(CH₂)₅CH₃ |
| 2 | —CH₂—CH=CH₂ | H | OCH(CH₃)(CH₂)₃C₆H₅ |
| 2 | —CH₂—CH=CH₂ | H | C(CH₃)₂(CH₂)₅CH₃ |

EXAMPLE 8

Trans-3-[4-(1,1-Dimethylheptyl)-2-hydroxyphenyl]4-(3-hydroxypropyl)cyclohexanone A mixture of 4.0 g. (9.56 mmoles) of trans-3-[4-(1,1-dimethylheptyl)-2-hydroxyphenyl]-4-(3-hydroxypropyl)cyclohexanone ethylene ketal, 50 ml. of 2 N hydrochloric acid and 100 ml. of tetrahydrofuran was heated at reflux for 2 hours. The reaction was cooled and added to 500 ml. saturated sodium chloride and 250 ml. ether. The ether extract was separated and washed once with 500 ml. saturated sodium chloride, once with 500 ml. saturated sodium bicarbonate, dried over magnesium sulfate and evaporated (aspirator) to an oil. The crude oil was purified via column chromatography on 200 g. of silica gel eluted with 80% ether-hexane to yield 2.93 g. (82%) of the title compound as an oil.

IR (CHCl₃) 3521, 3333, 1709, 1616 and 1567 cm⁻¹.
MS (m/e) 374 (M⁺), 356, 289, 273, 247, 203 and 161.
PMR $\delta_{CDCl_3}^{TMS}$ 0.82 (m terminal methyl), 1.28 (s, gem dimethyl), 3.76 (m, alcohol methylene), 6.8 (m, ArH) and 6.99 (d, J=8 Hz, ArH).

In like manner the following compounds are prepared from appropriate ketals:

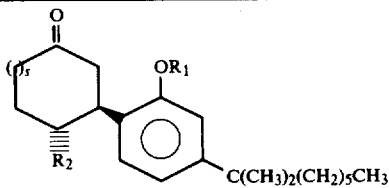

|   |       |            | Reactant |       | IR (CHCl3) |         |     |
|---|-------|------------|----------|-------|------------|---------|-----|
| s | R1    | R2         | Gms.     | Yield | cm$^{-1}$  | MS(m/e) | PMR $\delta_{CDCl_3}^{TMS}$ |
| 1 | C7H7 | CH2CH2OH | 1.00 (2.03 mM) | Quantitative an oil | 3509, 1733, 1626, 1587 | 450(M+) 365, 363, 359, 273, 91 | |
| 1 | C7H7 | CH2—CH—CH3 OH Diastereomer A | 0.680 (1.33 mM) | Quantitative an oil | | | Rf = 0.20 (0.25 mm silica gel, 66% ether-pentane) |
| 1 | C7H7 | CH2—CH—CH3 OH Diastereomer B | 0.980 (1.92 mM) | Quantitative an oil | | | Rf = 0.20 (0.25 mm silica gel, 66% ether-pentane) |
| 1 | C7H7 | (CH2)4—CHO (a) | 0.400 (0.692 mM) | Quantitative an oil | | | 0.82 (m, terminal methyl), 1.23 (s, gem dimethyl), 5.06 (s, benzylic methylene), 6.88 (m, ArH), 7.03 (d, J = 8Hz, ArH), 7.36 (bs, PhH) and 9.58 (t, J = 2Hz, CHO). |
| 2 | C7H7 | CH2CH2CH2OH | 3.5 (8.1 mM) | 0.967 g. (31%) an oil | 3571, 3425, 1695, 1613, 1577 | 478(M+) | 0.80 (m, terminal methyl), 1.27 (s, gem dimethyl), 2.7–3.6 (m, alcohol methylene and benzylic methine), 5.02 (s, benzylic methylene), 6.9 (m, ArH) and 7.4 (m, PhH). |

(a) Reactant used as bis ethylene ketal.

EXAMPLE 9

Trans-3-[2-Benzyloxy-4-(1,1-dimethylheptyl)phenyl]-4-(2-oxoethyl)cyclohexanone ethylene ketal A mixture of 17.0 g. (34.7 mmoles) of trans-3-[2-benzyloxy-4-(1,1-dimethylheptyl)phenyl]-4-(2-propenyl)-cyclohexanone ethylene ketal, 44.5 g. (0.208 mmole) of sodium metaperiodate and 176 mg. (0.69 mmole) of osmium tetroxide in 340 ml. tetrahydrofuran and 100 ml. of water was stirred at room temperature for 3.5 hours. The reaction mixture was then added to 1000 ml. 15% sodium sulfite-1000 ml. ether. The organic phase was separated, washed twice with 500 ml. of saturated sodium bicarbonate, dried over magnesium sulfate and evaporated (aspirator). The residue was purified by column chromatography on 400 g. of silica gel eluted with 33–75% ether-petroleum ether to yield 10.0 g. (59%) of the title compound as an oil.

IR (CHCl3) 1730, 1621 and 1577 cm$^{-1}$.

MS (m/e) 492 (M+), 464, 448, 407, 401, 357, 339, 332, 319, 317, 271 and 91.

PMR $\delta_{CDCl_3}^{TMS}$ 0.83 (m, terminal methyl), 1.23 (s, gem dimethyl), 3.2 (m, benzylic methine), 3.94 (s, ethylene ketal), 5.10 (s, benzylic methylene), 6.85 (dd, J-8 and 2 Hz, ArH), 6.85 (d, J=2 Hz, ArH), 7.07 (d, J=8 Hz, ArH) and 9.57 (t, J=1.5 Hz, CHO).

Further elution gave 5.53 g. of a mixture of two compounds. This mixture was dissolved in 500 ml. of ether and washed with four 250 ml. portions of 1 N sodium hydroxide. The ether phase was dried over magnesium sulfate and evaporated (aspirator) to yield 2.7 g. of oil. This oil was further purified via column chromatography on 100 g. of silica gel eluted with 50% etherpentane to yield 2.16 g. (12%) of trans-3-[2-benzyloxy-4-(1,1-dimethylheptyl)phenyl]-4-(3-hydroxy-2-oxopropyl)cyclohexanone ethylene ketal as an oil. The basic extract from above was acidified with ice cold 6 N hydrochloric acid and then extracted with 500 ml. of ether. The ether extract was washed twice with 200 ml. water, once with 100 ml. saturated sodium chloride, dried over magnesium sulfate and evaporated to give 2.4 g. of oil which was purified by column chromatography on 100 g. of silica gel eluted with 33% ethyl acetate-pentane to yield 1.51 g. (9%) of trans-3-[2-benzyloxy-4-(1,1-dimethylheptyl)phenyl]-4-(2-carboxymethyl)cyclohexanone ethylene ketal.

Trans-3-[2-benzyloxy-4-(1,1-dimethylheptyl)phenyl]-4-(3-hydroxy-2-oxopropyl)cyclohexanone ethylene ketal:

IR (CHCl3) 3484, 1724, 1613 and 1575 cm$^{-1}$.

MS (m/e) 522 (M+), 491, 448, 432, 407, 358, 99, 91 and 86.

PMR $\delta_{CDCl_3}^{TMS}$ 0.82 (terminal methyl), 1.22 (s, gem dimethyl), 2.17 (m, methylene α to ketone), 2.88 (t, J=5 Hz, OH), 3.82 (d, overlaps 3.90), 3.90 (s, ethylene), 5.08 (s, benzylic methylene), 6.83 (m, ArH), 7.02 (d, J=8 Hz, ArH) and 7.40 (m, PhH).

Trans-3-[2-benzyloxy-4-(1,1-dimethylheptyl)phenyl]-4-(2-carboxymethyl)cyclohexanone ethylene ketal:

IR (CHCl3) 3636–2273 (broad), 1724, 1621 and 1582 cm$^{-1}$.

MS (m/e) 508 (M+), 449, 424, 418, 408, 402, 99, 91 and 86.

PMR $\delta_{CDCl_3}^{TMS}$ 0.82 (m, terminal methyl), 1.22 (s, gem dimethyl), 3.2 (m, benzylic methine), 3.93 (s, ethylene), 5.10 (s, benzylic methylene), 6.85 (m, ArH), 7.10 (d, J=8 Hz, ArH) and 7.41 (m, PhH).

Similarly, oxidation of 2.60 g. (5.80 mmole) of cis-3-[2-benzyloxy-4-(1,1-dimethylheptyl)phenyl]-trans-4-(2-propenyl)cyclohexanol gave 1.4 g. (54%) of cis-3-[2-benzyloxy-4-(1,1-dimethylheptyl)phenyl]-trans-4-(2-oxoethyl)cyclohexanol; 409 mg. (15%) of cis-3-[2-benzyloxy-4-(1,1-dimethylheptyl)phenyl]-trans-4-(3-hydroxy-2-oxopropyl)cyclohexanol and 120 mg. (4.9%) of cis-3-[2-benzyloxy-4-(1,1-dimethylheptyl)phenyl]-trans-4-(carboxymethyl)cyclohexanol.

2-Oxoethyl compound:

IR (CHCl$_3$) 3610, 3425, 1623 and 1582 cm$^{-1}$.

MS (m/e) 450 (M+), 422, 405, 365, 359, 342 and 91.

PMR $\delta_{CDCl_3}^{TMS}$ 0.82 (m, terminal methyl), 1.23 (s, gem dimethyl), 3.00 (m, benzylic methine), 3.70 (m, carbinol methine), 5.09 (s, benzylic methylene), 6.88 (d, J=2 Hz, ArH), 6.88 (dd, J=8 and 2 Hz, ArH), 7.10 (d, J=8 Hz, ArH), 7.40 (s, PhH) and 9.53 (t, J=1.5 Hz, CHO). α-Hydroxy ketone:

IR (CHCl$_3$) 3448, 1721, 1618 and 1580 cm$^{-1}$.

MS (m/e) 480 (M+), 466, 450, 449, 406 and 91.

PMR $\delta_{CDCl_3}^{TMS}$ 0.82 (m, terminal methyl), 1.22 (s, gem dimethyl), 3.75 (m, carbinol methine), 3.86 (bs, hydroxymethylene), 5.08 (s, benzylic methylene), 6.95 (m, ArH), 7.05 (d, J=8 Hz, ArH) and 7.38 (s, PhH).

Acid:

Rf=0.32 (0.25 mm, silica gel ether).

In like manner, 3,4-trans, 4,5-trans-3-[2-benzyloxy-4-(1,1-dimethylkeptyl)phenyl]-5-methyl-4-(2-propenyl)cyclohexanone ethylene ketal is oxidized to the corresponding 4-(2-oxoethyl)cyclohexanone derivative. Also produced are the corresponding 4-(3-hydroxy-2-oxopropyl)- and the 4-(2-carboxymethyl)cyclohexanone derivatives.

EXAMPLE 10

Trans-3-[2-Benzyloxy-4-(1,1-dimethylheptyl)phenyl]-4-(5-oxopent-2-enyl)cyclohexanone bis ethylene ketal To a 15° C. solution of 4.05 mmole of sodium dimsylate in 6 ml. of dimethyl sulfoxide is added 1.61 g. (4.05 mmole) of 2-(1,3-dioxolan-2-yl)ethyltriphenylphosphonium bromide. The reaction mixture was stirred for 15 minutes and then a solution of 1.0 g. (2.03 mmole) of trans-3-[2-benzyloxy-4-(1,1-dimethylheptyl)-phenyl]-4-(2-oxoethyl)cyclohexanone ethylene ketal in one ml. of dimethyl sulfoxide was added. The reaction was stirred for 10 minutes and then added to a mixture of 200 ml. saturated sodium chloride and 200 ml. ether with stirring. The ether phase was separated and washed twice with 200 ml. of saturated sodium chloride, dried over magnesium sulfate and evaporated to an oil. The crude product was purified via column chromatography on 60 g. of silica gel eluted with 30% ether-pentane to yield 359 mg. (31%) of the title compound as an oil.

IR (CHCl$_3$) 1600 and 1563 cm$^{-1}$.

MS (m/e) 576 (M+).

PMR $\delta_{CDCl_3}^{TMS}$ 0.82 (m, terminal methyl), 1.24 (s, gem dimethyl), 2.25 (m, methylene), 3.2 (m, benzylic methine), 3.85 (m, ethylenes), 4.80 (t, J=5 Hz, dioxolane methine), 5.08 (s, benzylic methylene), 5.42 (m, olefinic H), 6.85 (m, ArH), 7.09 (d, J=8 Hz, ArH) and 7.4 (m, PhH).

In like manner, 3,4-trans, 4,5-trans-3-[2-benzyloxy-4-(1,1-dimethylheptyl)phenyl]-5-methyl-4-(2-oxoethyl)-cyclohexanone ethylene ketal and cis-3-[2-benzyloxy-4-(R)-(1-methyl-4-phenylbutoxy)phenyl]-4-trans-(2-oxoethyl)cycloheptanone ethylene ketal are converted to the corresponding 4-(5-oxopent-2-enyl)bis ethylene ketals.

EXAMPLE 11

Trans-3-[2-Benzyloxy-4-(1,1-dimethylheptyl)phenyl]-4-(5-oxopentyl)cyclohexanone bis ethylene ketal A mixture of 520 mg. (0.902 mmole) of trans-3-[2-benzyloxy-4-(1,1-dimethylheptyl)phenyl]-4-(5-oxopent-2-enyl)cyclohexanone bis ethylene ketal and 100 mg. of 5% Pd/C/50% water in 15 ml. of ethanol was stirred under one atmosphere of hydrogen gas until one equivalent of hydrogen was absorbed. The reaction was filtered through diatomaceous earth and evaporated to give a quantitative yield of the title compound as an oil.

PMR $\delta_{CDCl_3}^{TMS}$ 0.80 (m, terminal methyl), 1.32 (s, gem dimethyl), 3.9 (m, ethylenes), 4.78 (m, dioxolane methine), 5.08 (s, benzylic methylene), 6.85 (m, ArH), 7.08 (d, J=8 Hz, ArH) and 7.42 (m, PhH).

Deketalization according to the procedure of Example 8 affords the corresponding (5-oxopentyl)cycloalkanone as an oil.

PMR $\delta_{CDCl_3}^{TMS}$ 0.82 (m, terminal methyl), 1.23 (s, gem dimethyl), 5.06 (s, benzylic methylene), 6.88 (m, ArH), 7.03 (d, J=8 Hz, ArH), 7.36 (bs, PhH) and 9.58 (t, J=2 Hz, CHO).

The remaining products of Example 10 are reduced and deketalized in like manner to the corresponding 5-oxopentyl ketones.

EXAMPLE 12

Trans-3-[2-Benzyloxy-4-(1,1-dimethylheptyl)phenyl]-4-(2-hydroxypropyl)cyclohexanone ethylene ketal Diastereomers A and B To a 0° C. solution of 1.72 ml. (5.00 mmole) of methyl magnesium iodide (2.9 M in 5 ml. of ether) was added a solution of 2.0 g. (4.06 mmole) of trans-3-[2-benzyloxy-4-(1,1-dimethylheptyl)phenyl]-4-(2-oxoethyl)cyclohexanone ethylene ketal in 5 ml. of ether. The reaction was stirred 30 minutes and then added to 250 ml. saturated ammonium chloride and 250 ml. ether. The organic extract was washed with 250 ml. of saturated sodium chloride, dried over magnesium sulfate and evaporated to an oil. The crude oil was purified via high pressure liquid chromatography on four 60 cm×9.5 mm Porasil B (a form of silica gel available from Waters Associates, Milford, Mass., U.S.A.) columns eluted with 60% ether-hexane to yield in order of elution 746 mg. (36%) of diastereomer A of the title compound and 935 mg. (45%) of diastereomer B of the title compound.

Diastereomer A:

IR (CHCl$_3$) 3571, 3472, 1613 and 1575 cm$^{-1}$.

MS (m/e) 508 (M+).

PMR $\delta_{CDCl_3}^{TMS}$ 0.85 (m, sidechain methyl), 1.06 (d, J=6 Hz, methyl), 1.26 (s, gem dimethyl), 3.0 (m, benzylic methine), 3.7 (m, carbinol methine), 3.98 (s, ethylene), 5.02 (s, benzylic methylene), 6.81 (d, J=2 Hz, ArH), 6.81 (dd, J=8 and 2 Hz, ArH), 7.08 (d, J=8 Hz, ArH) and 7.37 (m, PhH).

Diastereomer B:

IR (CHCl$_3$) 3610, 3460, 1618 and 1575 cm$^{-1}$.

MS (m/e) 508 (M+).

PMR $\delta_{CDCl_3}^{TMS}$ 0.85 (m, sidechain methyl), 0.99 (d, J=6 Hz, methyl), 1.27 (s, gem dimethyl), 3.1 (m, benzylic methine), 3.55 (m, carbinol methine), 6.82 (m, ArH), 7.04 (d, J=8 Hz, ArH) and 7.35 (m, PhH).

EXAMPLE 13

Trans-3-[2-Benzyloxy-4-(1,1-dimethylheptyl)phenyl]-cis-4-(2-propenyl)cycloheptanol To a refluxing solution of 3.0 g. (0.0789 mole) of sodium borohydride in 50 ml. of isopropanol was added a solution of 5.0 g. (0.011 mole) of trans-3-[2-benzyloxy-4-(1,1-dimethylheptyl)phenyl]-4-(2-propenyl)cycloheptanone in 50 ml. of isopropanol over a 1.5 hour period. The reaction was heated one hour longer, cooled and then added to 500 ml. saturated sodium chloride. The quench was extracted twice with 800 ml. saturated ether, the extracts combined, dried over magnesium sulfate and evaporated (aspirator) to an oil. The crude oil was purified via column chromatography on 500 g. of silica gel eluted with 15% ether-hexane to yield in order of elution 1.78 g. (36%) of the title compound, 0.55 g. (11%) of mixture and 1.84 g. (36%) of the cis 3-trans-4 isomer of the title compound as oils.

Cis, trans isomer:

IR (CHCl$_3$) 3333, 1626, 1600 and 1563 cm$^{-1}$.

MS (m/e) 462 (M+) and 91.

PMR $\delta_{CDCl_3}{}^{TMS}$ 0.82 (m, terminal methyl), 1.22 (s, gem dimethyl), 2.70 (m, benzylic methine), 3.70 (m, carbinol methine), 4.5–5.0 and 5.1–6.0 (m, olefinic), 5.03 (s, benzylic methylene), 6.75 (m, ArH), 7.02 (d, J=8 Hz) and 7.34 (s, PhH).

Title compound:

IR (CHCl$_3$) 3571, 1642, 1613 and 1575 cm$^{-1}$.

MS (m/e) 462 (M+) and 91.

PMR $\delta_{CDCl_3}{}^{TMS}$ 0.80 (m, terminal methyl), 1.22 (s, gem dimethyl), 4.6–5.0 and 5.2–6.0 (m, olefinic H), 5.02 (s, benzylic methylene), 6.88 (m, ArH), 7.03 (d, J=8 Hz, ArH) and 7.30 (bs, PhH).

EXAMPLE 14

Cis-3-[2-benzyloxy-4-(1,1-dimethylheptyl)phenyl]-trans-4-(2-propenyl)cycloheptyl d-mandelate

Diastereomer A & B

A mixture of 2.2 g. (4.76 mmole) of cis-3-[2-benzyloxy-4-(1,1-dimethylheptyl)phenyl]-trans-4-(2-propenyl)cycloheptanol, 869 mg. (5.72 mmole) of d-mandelic acid and 110 mg. (0.579 mmole) of p-toluenesulfonic acid monohydrate in 40 ml. of benzene was heated at reflux for 7 hours. Water was removed via a soxhlet extractor filled with a synthetic crystalline aluminosilicate (molecular sieve) such as those distributed by the Linde Company or the Davison Chemical Company. The reaction was stirred at 25° C. for 9 hours and then added to 300 ml. of saturated sodium bicarbonate and 300 ml. ether. The ether phase was separated and washed once with 300 ml. of saturated sodium bicarbonate, dried over magnesium sulfate and evaporated (aspirator) to an oil. The crude oil was purified via column chromatography on silica gel eluted with 15% ether-hexane to yield in order of elution 1.08 g. (38%) of diastereomer A of the title compound, 0.233 g. (8%) of mixture and 1.12 g. of diastereomer B of the title compound as an oil.

Diastereomer A:

m.p.: 86°–90° C. (Methanol)

HRMS (m/e) 596.3883 (M+, calc'd. for C$_{40}$H$_{52}$O$_4$: 596.3852), 444, 359, 354, 313, 269 and 91.

PMR $\delta_{CDCl_3}{}^{TMS}$ 0.82 (m, terminal methyl), 1.22 (s, gem dimethyl), 2.90 (m, benzylic methine), 3.45 (m, ester methine), 4.5–6.0 (m, olefinic and mandelate H), 5.06 (s, benzyl ether methylene), 6.90 (m, ArH) and 7.38 (m, PhH).

$[\alpha]_D{}^{CH_3OH, 25° C.} = +4.42°$

Diastereomer B:

HRMS (m/e) 596.3855 (M+, calc'd. for C$_{40}$H$_{52}$O$_4$: 596.3852), 354, 269, 107 and 91.

PMR $\delta_{CDCl_3}{}^{TMS}$ 0.82 (m, terminal methyl), 1.21 (s, gem dimethyl), 2.80 (m, benzylic methine), 3.40 (m, ester methine), 4.5–6.0 (m, olefinic and mandelate H), 6.80 (m, ArH) and 7.25 (m, PhH).

$[\alpha]_D{}^{CH_3OH, 25° C.} = +53.34°$

EXAMPLE 15

Cis-3-[2-Benzyloxy-4-(1,1-dimethylheptyl)phenyl]-trans-4-(2-propenyl)cycloheptanol Enantiomer A A mixture of 1.25 g. (2.09 mmole) of cis-3-[2-benzyloxy-4-(1,1-dimethylheptyl)phenyl]-trans-4-(2-propenyl)cycloheptyl d-mandelate, diastereomer A, and 577 mg. (4.18 mmole) of potassium carbonate in 20 ml. methanol, 5 ml. tetrahydrofuran and 2 ml. of water was stirred at 25° C. for 20 hours. The reaction was added to 300 ml. water-250 ml. ether. The ether extract was washed once with 300 ml. saturated sodium chloride, dried over magnesium sulfate and evaporated. The crude product was purified via column chromatography on 75 g. of silica gel eluted with 33% ether-hexane to yield 650 mg. (67%) of the title compound as an oil.

HRMS (m/e) 462.3482 (M+, calc'd. for C$_{32}$H$_{46}$O$_2$: 462.3490), 377, 313, 269, 233, 227 and 91.

$[\alpha]_D{}^{CH_3OH, 25° C.} = -20.18°$

In like manner 1.25 g. (2.09 mmole) of cis-3-[2-benzyloxy-4-(1,1-dimethylheptyl)phenyl]-trans-4-(2-propenyl)cycloheptyl d-mandelate, diastereomer B, was converted to 383 mg. (40%) of cis-3-[2-benzyloxy-4-(1,1-dimethylheptyl)phenyl]-trans-4-(2-propenyl)cycloheptanol enantiomer B as an oil.

HRMS (m/e) 462.3543 (M+, calc'd. for C$_{32}$H$_{46}$O$_2$: 462.3490), 377, 313, 269, 233, 227 and 91.

$[\alpha]_D{}^{CH_3OH, 25° C.} = +16.06°$

EXAMPLE 16

Cis-3-[2-Hydroxy-4-(1,1-dimethylheptyl)phenyl]trans-4-(2-aminoethyl)cyclohexanol hydrochloride A mixture of 1.00 g. (2.77 mmole) of cis-3-[2-hydroxy-4-(1,1-dimethylheptyl)phenyl]-trans-4-(2-oxoethyl)cyclohexanol, 2.31 g. (30.0 mmole) of ammonium acetate and 177 mg. (2.77 mmole) of sodium cyanoborohydride in 10 ml. of methanol was stirred for 16 hours at 25° C. The pH of the reaction was made <2 with concentrated hydrochloric acid and the methanol evaporated on a rotovapor. The residue was dissolved in 200 ml. of water and 20 ml. of methanol and the solution washed twice with 200 ml. of ether. The aqueous phase was separated and made basic (pH>10) with concentrated sodium hydroxide, saturated with sodium chloride and extracted with 200 ml. of ether. This ether phase was removed, dried over magnesium sulfate and evaporated (aspirator) to an oil. The oil was dissolved in dichloromethane and excess ethereal hydrogen chloride added forming an oily precipitate which crystallized from ether-ethyl acetate-ethanol (1-1-1) solution upon cooling to yield 136 mg. (12%) of the title compound.

m.p.: 218°–220° C. (ether, ethyl acetate, ethanol)

HRMS (m/e) 361.2993 (M+, calc'd. for C$_{23}$H$_{39}$NO$_2$: 361.2971), 276, 259 and 241.

EXAMPLE 17

Cis-3-[2-Benzyloxy-4-(1,1-dimethylheptyl)phenyl]-trans-4-oxomethylcyclohexanol

A mixture of 14.4 g. (29.9 mmole) of cis-3-[2-benzyloxy-4-(1,1-dimethylheptyl)phenyl]-trans-4-dimethoxymethylcyclohexanol, 150 ml. of 1,4-dioxane and 150 ml. of 2 N hydrochloric acid was refluxed for one hour. The reaction was cooled and added to 2 liters of saturated sodium chloride. The aqueous quench was extracted twice with 300 ml. of ether and the combined ether extract washed once with saturated sodium bicarbonate, dried over magnesium sulfate and evaporated on a rotovac to give a quantitative yield of the title compound as an oil.

IR (CHCl$_3$) 3546, 3401, 1715, 1607 and 1572 cm$^{-1}$.
MS (m/e) 436 (M+), 352, 345, 328, 310, 299, 259 and 91.
PMR $\delta_{CDCl_3}^{TMS}$ 0.82 (m, terminal methyl), 1.22 (s, gem dimethyl), 2.75 (m, benzylic methine), 3.65 (m, carbinol methine), 5.01 (s, benzylic methylene), 6.83 (m, ArH), 7.06 (d, J=8 Hz, ArH) and 7.36 (s, PhH).

Similarly, 6.3 g. (13.07 mmole) of trans-3-[2-benzyloxy-4-(1,1-dimethylheptyl)phenyl]-cis-4-dimethoxymethylcyclohexanol (contains some of the cis-3, trans-4-isomer) was converted to 2.05 g. (36%) of trans-3-[2-benzyloxy-4-(1,1-dimethylheptyl)phenyl]-cis-4-oxomethylcyclohexanol and 2.2 g. (39%) of the cis-3, trans-4 isomer. Separation was achieved via column chromatography on 120 g. of silica gel eluted with 66% ether-hexane. Trans, cis isomer:

IR (CHCl$_3$) 1715, 1607 and 1557 cm$^{-1}$.
MS (m/e) 436 (M+), 418, 351 328 and 91.
PMR $\delta_{CDCl_3}^{TMS}$ 0.86 (m, terminal methyl), 1.28 (s, gem dimethyl), 2.7 (m, benzylic methine), 4.22 (m, carbinol methine), 5.13 (s, benzylic methylene), 6.9 (m, ArH), 7.15 (d, J=8 Hz, ArH), 7.42 (bs, PhH) and 9.42 (d, J=3 Hz, CHO).

EXAMPLE 18

Cis-3-[2-Benzyloxy-4-(1,1-dimethylheptyl)phenyl]-trans-4-oxomethylcyclohexanol oxime A mixture of 1.5 g. (3.44 mmole) of cis-3-[2-benzyloxy-4-(1,1-dimethylheptyl)phenyl]-trans-4-oxomethylcyclohexanol and 358 mg. (5.15 mmole) of hydroxylamine hydrochloride in 10 ml. of pyridine was stirred at 25° C. for 24 hours. The reaction was added to one liter of 10% hydrochloric acid and extracted with 250 ml. ether. The ether extract was washed with 200 ml. saturated sodium bicarbonate, 200 ml. saturated sodium chloride, dried over magnesium sulfate and evaporated to yield 1.40 g. (90%) of the title compound as an oil.

IR (CHCl$_3$) 3533, 3300, 1612 and 1572 cm$^{-1}$.
MS (m/e) 451 (M+), 433 and 91.
PMR $\delta_{CDCl_3}^{TMS}$ 0.86 (m, terminal methyl), 1.28 (s, gem dimethyl), 2.5–4.0 (m, 3H), 5.08 (s, benzylic methylene), 6.39 (m, 1H), 6.7–7.2 (m, ArH) and 7.40 (s, PhH).

In like manner trans-3-[2-benzyloxy-4-(1,1-dimethylheptyl)phenyl]-cis-4-oxomethylcyclohexanol oxime was prepared in 89% (1.84 g.) yield as an oil from 2.00 g. (4.59 mmole) of trans-3-[2-benzyloxy-4-(1,1-dimethylheptyl)phenyl]-cis-4-oxomethylcyclohexanol.

IR (CHCl$_3$) 3497, 3225, 1600 and 1562 cm$^{-1}$.
MS (m/e) 451 (M+), 433, 416, 362, 348 and 91.
PMR $\delta_{CDCl_3}^{TMS}$ 0.82 (m, terminal methyl), 1.22 (s, gem dimethyl), 4.13 (m, carbinol methine), 5.08 (s, benzylic methylene), 6.85 (m, ArH), 7.08 (d, J=8 Hz, ArH) and 7.40 (bs, PhH).

EXAMPLE 19

Cis-3-[2-Benzyloxy-4-(1,1-dimethylheptyl)phenyl]-trans-4-(2-carbomethoxyethenyl)cyclohexanol To a 25° C. slurry of 242 mg. (10.1 mmole) of sodium hydride in 20 ml. tetrahydrofuran and 10 ml. dimethylformamide was added dropwise a solution of 1.83 g. (10 mmole) of methyl dimethylphosphonoacetate in 5 ml. of tetrahydrofuran. The reaction was stirred 5 minutes and then a solution of 2.0 g. (4.58 mmole) of cis-3-[2-benzyloxy-4-(1,1-dimethylheptyl)phenyl]-trans-4-oxomethylcyclohexanol in 5 ml. of tetrahydrofuran was added dropwise. The reaction was stirred 15 minutes longer and then added to 700 ml. of saturated sodium chloride. The quenched reaction was extracted with 250 ml. of ether, the extract dried over magnesium sulfate and evaporated to an oil. The crude oil was purified via column chromatography on 50 g. of silica gel eluted with 50% ether-pentane to yield 1.28 g. (58%) of the title compound as an oil.

IR (CHCl$_3$) 3389, 1709, 1650, 1610 and 1557 cm$^{-1}$.
MS (m/e) 492 (M+), 407, 383, 323 and 91.
PMR $\delta_{CDCl_3}^{TMS}$ 0.83 (m, terminal methyl), 1.25 (s, gem dimethyl), 3.10 (m, benzylic methine) 3.62 (s, methyl ester), 3.62 (m, carbinol methine), 5.05 (s, benzylic methylene), 5.57 (d, J=16 Hz, olefinic H), 6.85 (m, ArH), 7.05 (d, J=8 Hz, ArH) and 7.40 (s, PhH).

EXAMPLE 20

Cis-3-[2-Benzyloxy-4-(1,1-dimethylheptyl)phenyl]-trans-4-(2-carbamoylethenyl)cyclohexanol A mixture of 3.0 g. (6.88 mmole) of cis-3-[2-benzyloxy-4-(1,1-dimethylheptyl)phenyl]-trans-4-oxomethylcyclohexanol and 2.43 g. (7.58 mmole) of carbamoylmethylenetriphenylphosphorane in 40 ml. of dichloromethane was heated at reflux for 24 hours. The reaction was concentrated and ether added to cause crystallization of triphenylphosphine oxide. The residue was purified first via column chromatography on 120 g. of silica gel eluted with ether and then on 111 g. of neutral alumina eluted with 0–100% ethyl acetate-ether to yield 2.0 g. (61%) of the title compound as an oil.

IR (CHCl$_3$) 3533, 1678, 1612 and 1587 cm$^{-1}$.
MS (m/e) 477 (M+), 460, 386, 368 and 307.
PMR $\delta_{CDCl_3}^{TMS}$ 0.84 (m, terminal methyl), 1.22 (s, gem dimethyl), 3.05 (m, benzylic methine), 3.70 (m, carbinol methine), 5.08 (s, benzylic methylene), 5.50 (d, J=16 Hz, olefinic), 6.95 (m, ArH), 7.07 (d, J=8 Hz, ArH) and 7.42 (bs, PhH).

EXAMPLE 21

Cis-3-[2-Hydroxy-4-(1,1-dimethylheptyl)phenyl]trans-4-(2-carbomethoxyethyl)cyclohexanol A mixture of 1.28 g. (2.60 mmole) of cis-3-[2-benzyloxy-4-(1,1-dimethylheptyl)phenyl]-trans-4-(2-carbomethoxyethenyl)cyclohexanol and 640 mg. of 5% Pd/C/50% H$_2$O in 20 ml. of methanol was stirred under one atmosphere of hydrogen for 75 minutes. The reaction was filtered through diatomaceous earth and the filtrate evaporated. The residue was again mixed with 640 mg. of fresh 5% Pd/C/50% H$_2$O in 20 ml. of methanol and stirred under one atmosphere of hydrogen for 30 minutes, then filtered and evaporated as before. The residual oil was crystallized in ether-pentane to yield 540 mg. (51%) of the title compound.

m.p.: 81°-83° C. (ether-pentane)
IR (CDCl$_3$) 3521, 3289, 1724, 1612 and 1574 cm$^{-1}$.
MS (m/e) 404 (M+), 386, 355, 332 and 319.
PMR $\delta_{CDCl_3}{}^{TMS}$ 0.82 (m, terminal methyl), 1.22 (s, gem dimethyl), 2.65 (m, benzylic methine), 3.46 (s, methyl ester), 3.6 (m, carbinol methine), 5.7 (broad, OH), 6.75 (m, ArH) and 7.03 (d, J=8 Hz, ArH).
Analysis: Calc'd. for C$_{25}$H$_{40}$O$_4$: C, 74.22; H, 9.97. Found: C, 73.85; H, 9.64.

Similarly, cis-3-[2-hydroxy-4-(1,1-dimethylheptyl)phenyl]-trans-4-(2-carbamoylethyl)cyclohexanol was prepared in 39% (630 mg.) yield from 2.00 g. (4.19 mmole) of cis-3-[2-benzyloxy-4-(1,1-dimethylheptyl)phenyl]trans-4-(2-carbamoylethenyl)cyclohexanol.

m.p.: 152°-153° C. (ethyl acetate)
IR (KBr) 3267, 3095, 1661, 1618 and 1575 cm$^{-1}$.
MS (m/e) 389 (M+), 372, 371, 354, 353, 286, 287 and 269.
PMR (CDCl$_3$+D$_6$-DMSO)$\delta^{TMS}$ 0.83 (m, terminal methyl), 1.25 (s, gem dimethyl), 3.0 (m, benzylic methine), 3.70 (m, carbinol methine), 6.75 (m, ArH) and 7.03 (d, J=8 Hz, ArH).
Analysis: Calc'd. for C$_{24}$H$_{39}$NO$_3$: C, 73.99; H, 10.09; N, 3.60. Found: C, 74.10; H, 10.11; N, 3.52.

EXAMPLE 22

Cis-3-[2-Hydroxy-4-(1,1-dimethylheptyl)phenyl]-trans-4-(2-carboxyethyl)cyclohexanol A mixture of 1.01 g. (2.50 mmole) of cis-3-[2-hydroxy-4-(1,1-dimethylheptyl)phenyl]-trans-4-(2-carbomethoxyethyl)cyclohexanol, 25 ml. 6 N sodium hydroxide and 25 ml. dioxane was heated at reflux for 40 minutes and then cooled to 0° C. and acidified with 6 N hydrochloric acid. The quenched reaction as diluted with saturated sodium chloride and extracted several times with ether and then dichloromethane. The combined organic extract was evaporated and the residue recrystallized from ethyl acetate to yield 314 mg. (32%) of the title compound.

m.p.: 194°-195° C. (ethyl acetate)
IR (KBr) 3367, 3125, 1694, 1612 and 1575 cm$^{-1}$.
HRMS (m/e) 390.2758 (M+, calc'd. for C$_{24}$H$_{38}$O$_4$: 390.2760), 305, 287, 269.
PMR (CDCl$_3$, D$_6$-DMSO) $\delta^{TMS}$ 0.82 (m, terminal methyl), 1.23 (s, gem dimethyl), 3.50 (m, carbinol methine), 6.78 (m, ArH) and 7.04 (d, J=8 Hz, ArH).

EXAMPLE 23

Cis-3-[2-Hydroxy-4-(1,1-dimethylheptyl)phenyl]-trans-4-(3-aminopropyl)cyclohexanol To a 0° C. slurry of 500 mg. (13.1 mmole) of lithium aluminum hydride in 15 ml. of tetrahydrofuran was added a solution of 460 mg. (1.18 mmole) of cis-3-[2-hydroxy-4-(1,1-dimethylheptyl)phenyl]-trans-4-(2-carbamoylethyl)cyclohexanol in 14 ml. of tetrahydrofuran. The reaction was stirred at 25° C. for one hour and a reflux for 20 hours. The reaction was cooled to 0° C. and quenched by the addition of a 30% solution of sodium potassium tartrate. The quenched reaction was extracted with ethyl acetate, the extract dried over magnesium sulfate and evaporated to an oil. Crystallization of the residue in ether-ethyl acetate gave 390 mg. (88%) of the title compound.

m.p.: 137°-138° C.
MS (m/e) 375 (M+), 358 and 340.

PMR (CDCl$_3$+D$_6$DMSO)$\delta^{TMS}$ 0.80 (m, terminal methyl), 1.22 (s, gem dimethyl), 3.34 (bs, exchangeable OH), 3.75 (m, carbinol methine), 6.75 (m, ArH) and 7.00 (d, J=8 Hz, ArH).

The following compounds were similarly prepared:
cis-3-[2-hydroxy-4-(1,1-dimethylheptyl)phenyl]-trans-4-aminomethylcyclohexanol in 43% (819 mg.) yield from 1.99 g. (5.51 mmole) of cis-3-[2-hydroxy-4-(1,1-dimethylheptyl)phenyl]-trans-4-oxomethylcyclohexanol oxime.

m.p.: 104°-106° C. (ethyl acetate-pentane)
IR (KBr) 3205, 1602 and 1572 cm$^{-1}$.
HRMS (m/e) 347.2853 (M+, calc'd. for C$_{22}$H$_{37}$NO$_2$: 347.2815), 245, 227.

trans-3-[2-hydroxy-4-(1,1-dimethylheptyl)phenyl]-cis-4-aminomethylcyclohexanol in 44% (427 mg.) yield from 1.01 g. (2.80 mmole) of trans-3-[2-hydroxy-4-(1,1-dimethylheptyl)phenyl]-cis-4-oxomethylcyclohexanol oxime.

m.p.: 121°-124° C. (ether-hexane)
MS (m/e) 347 (M+), 330, 312, 245 and 227.

EXAMPLE 24

Cis-3-[2-Hydroxy-4-(1,1-dimethylheptyl)phenyl]trans-4-(3-dimethylaminopropyl)cyclohexanol hydrochloride A mixture of 340 mg. (0.906 mmole) of cis-3-[2-hydroxy-4-(1,1-dimethylheptyl)phenyl]-trans-4-(3-aminopropyl)cyclohexanol, 268 μl. of 37% formaldehyde and 137 μl. of formic acid was heated at 100° C. for 30 minutes. The reaction was cooled and added to ether and saturated sodium bicarbonate. The ether extract was dried over magnesium sulfate and evaporated to yield an oil which was purified via column chromatography on 8 g. of silica gel eluted with 50% methanol-dichloromethane to yield 78 mg. (21%) of the free base of the title compound as a glass.

PMR $\delta_{CDCl_3}{}^{TMS}$ 0.82 (m, terminal methyl), 1.22 (s, gem dimethyl), 2.19 (s, N-methyls), 3.7 (m, carbinol methine), 5.55 (broad, OH), 6.75 (m, ArH) and 6.98 (d, J=8 Hz, ArH).
HRMS (m/e) 403.3447 (M+, 100%, calc'd. for C$_{26}$H$_{45}$NO$_2$: 403.3439). The above free base was dissolved in ether-ethanol and excess ethereal hydrogen chloride added. The solution was then evaporated and the residue crystallized from ether-dichloromethane to yield 71.8 mg. (18%) of the title compound.

m.p.: 170°-175° C. (ether-dichloromethane)
The following compounds were prepared by the above procedure:

cis-3-[2-hydroxy-4-(1,1-dimethylheptyl)phenyl]-trans-4-N,N-dimethylaminomethylcyclohexanol hydrochloride in 25% (30 mg.) yield from 100 mg. (0.288 mmole) of cis-3-[2-hydroxy-4-(1,1-dimethylheptyl)phenyl]-trans-4-aminomethylcyclohexanol.

m.p.: 202°-203° C. (ether-dichloromethane)
MS (m/e) 375 (M+)
Free Base:
PMR (CDCl$_3$) δ 0.82 (m, terminal methyl), 1.30 (s, gem dimethyl), 2.28 (s, N,N-dimethyl), 3.75 (m, carbinol methine), 6.9 (m, ArH) and 7.12 (d, J=8 Hz, ArH).
HRMS (m/e) 375.3140 (M+, calc'd. for C$_{24}$H$_{41}$NO$_2$: 375.3127).

trans-3-[2-hydroxy-4-(1,1-dimethylheptyl)phenyl]-cis-4-N,N-dimethylaminomethylcyclohexanol hydrochloride in 25% (198 mg.) yield from 672 mg. (1.94 mmole) of trans-3-[2-hydroxy-4-(1,1-dimethylheptyl)phenyl]-cis-4-aminomethylcyclohexanol.

m.p.: 176°–178° C.

PMR (CDCl₃) $\delta_{CDCl_3}^{TMS}$ 0.82 (m, terminal methyl), 1.25 (m, gem dimethyl and methylenes), 4.26 (m, carbinol methine) and 6.6–7.2 (m, ArH).

Free Base:

IR (CHCl₃) 3333, 1607 and 1563 cm⁻¹.

MS (m/e) 375 (M+), 330 and 245.

EXAMPLE 25

Trans-1-[2-Hydroxy-4-(1,1-dimethylheptyl)phenyl]-2-(3-hydroxypropyl)cyclohexane

A mixture of 1.9 g. (5.08 mmoles) of trans-3-[2-hydroxy-4-(1,1-dimethylheptyl)phenyl]-2-(3-hydroxypropyl)cyclohexanone and 10.2 ml. of hydrazine hydrate in 20 ml. of ethylene glycol is heated at 100° C. for an hour. The reaction was cooled to 60° C. and 4.05 g. (72.3 mmoles) of solid potassium hydroxide added. The resultant mixture was heated for 2 hours at 200° C., then cooled and added to 500 ml. 1 N hydrochloric acid and 300 ml. ether. The ether extract was washed with 300 ml. saturated sodium chloride, 300 ml. saturated sodium bicarbonate, dried over magnesium sulfate and evaporated under reduced pressure (aspirator) to an oil. The crude oil was purified via column chromatography on 100 g. of silica gel eluted with 70% ether-hexane to yield 406 mg. (22%) of the title compound as an oil.

IR (CHCl₃) 3509, 3279, 1605, 1595 and 1570 cm⁻¹.

MS (m/e) 360 (M+), 345, 342, 275, 257, 233, 215, 147 and 141.

PMR $\delta_{CDCl_3}^{TMS}$ 0.82 (m, terminal methyl), 1.25 (s, gem dimethyl), 2.58 (m, benzylic methine), 3.46 (bt, J=6 Hz, hydroxy methylene), 5.0 (broad, OH), 6.67 (d, J=2 Hz, ArH), 6.79 (d, J=8 and 2 Hz) and 7.02 (d, J=8 Hz, ArH).

EXAMPLE 26

Cis-3-[2-Benzyloxy-4-(1,1-dimethylheptyl)phenyl]-trans-4-(2-propenyl)-1-benzyloxycyclohexane To a slurry of 214 mg. (8.92 mmole) of sodium hydride in 10 ml. dimethylformamide was added a solution of 2.0 g. (4.46 mmole) of cis-3-[2-benzyloxy-4-(1,1-dimethylheptyl)phenyl]-trans-4-(2-propenyl)cyclohexanol in 10 ml. of dimethylformamide. The reaction was stirred 5 hours and then 0.6 ml. (4.9 mmole) of benzyl bromide was added. The reaction mixture was stirred 18 hours longer and added to 500 ml. saturated sodium chloride and 500 ml. ether. The organic extract was dried over magnesium sulfate and evaporated to yield an oil which was purified via column chromatography on 100 g. of silica gel eluted with 5% ether-hexane to yield 2.0 g. (83%) of the title compound as an oil.

IR (CHCl₃) 1639, 1600 and 1567 cm⁻¹.

HRMS (m/e) 538.3823 (M+, calc'd. for C₃₈H₅₀O₂: 538.3798), 453, 299, 255 and 91.

PMR $\delta_{CDCl_3}^{TMS}$ 0.83 (m, terminal methyl), 1.24 (s, gem dimethyl), 2.85 and 3.40 (m, ether methines), 4.50 and 5.05 (s, benzylic methylenes), 4.6–5.0 and 5.2–6.1 (n, vinyl H), 6.9 (m, ArH), 7.28 and 7.34 (bs, PhH).

EXAMPLE 27

Cis-3-[4-(1,1-Dimethylheptyl)-2-hydroxyphenyl]-trans-4-(3-methoxypropyl)cyclohexanol To a slurry of 172 mg. (7 mmole) of sodium hydride in 15 ml. dimethylformamide was added 2.0 g. (3.60 mmole) of cis-3-[2-benzyloxy-4-(1,1-dimethylheptyl)-phenyl]-trans-4-(3-hydroxypropyl)-1-benzyloxycyclohexane in 15 ml. dimethylformamide. The reaction mixture was then heated at 40°–50° C. for 3 hours, then cooled to 25° C. and 0.663 ml. (7.0 mmole) of dimethylsulfate was added. The resultant mixture was stirred 18 hours at 0° C. and then added to 250 ml. saturated sodium chloride and 250 ml. ether. The organic extract was dried over magnesium sulfate and evaporated to an oil. The crude oil was purified via column chromatography on 75 g. of silica gel eluted with 20% ether-hexane to yield 500 mg. (24%) of cis-3-[4-(1,1-dimethylheptyl)-2-hydroxyphenyl]-trans-4-(3-methoxypropyl)cyclohexanol as an oil.

PMR $\delta_{CDCl_3}^{TMS}$ 0.83 (m, terminal methyl), 1.23 (s, gem dimethyl), 3.20 (s, OCH₃), 2.6–4.0 (m), 4.54 and 5.06 (s, benzylic methylenes), 6.85 (m, ArH) and 7.28 (m, PhH).

Debenzylation of 500 mg. (0.874 mmole) of the product according to the procedure of Example 6 gives the title compound.

m.p.: 72°–74° C. (pentane)

MS (m/e) 390.3100 (M+, calc'd. for C₂₅H₄₂O₃; 390.3123), 372, 286, 272 and 147.

PMR (CDCl₃) δ 0.85 (m), 1.22 (s, gem dimethyl), 3.20 (OCH₃), 2.4–4.2 (several m), 5.05 (bs, OH), 6.8 (m, ArH) and 7.02 (d, J=8 Hz, ArH).

EXAMPLE 28

Trans-3-[2-Benzyloxy-4-(R)-(1-methyl-4-phenylbutoxy)phenyl]-4-(2-propenyl)cycloheptanone Using the procedure of Example 1, 23 g. (54.1 mmole) of (R)-1-bromo-2-benzyloxy-4-(1-methyl-4-phenylbutoxy)benzene and 7.5 g. (50.0 mmole) of 4-(2-propenyl)-2-cyclohepten-1-one gave 8.14 g. (30%) of the title compound as an oil.

[α]$_D^{25°}$ = −10.61° (C=1.077, CHCl₃)

HRMS (m/e) 496.2964 (M+, calc'd. for C₃₄H₄₀O₃: 496.2967), 405, 259, 241 and 91.

PMR $\delta_{CDCl_3}^{TMS}$ 1.22 (d, J=6 Hz, methyl), 4.33 (m, side-chain methine), 4.6–5.0 and 5.2–6.0 (m, vinyl H), 5.00 (s, benzylic methylene), 6.45 (m, ArH), 7.00 (d, J=8 Hz, ArH), 7.24 (s, PhH) and 7.42 (s, PhH).

EXAMPLE 29

Cis-3-[2-Benzyloxy-4-(R)-(1-methyl-4-phenylbutoxy)-phenyl]-4-trans-(2-propenyl)cycloheptanol and Isomeric Alcohol Using the procedure of Example 2, 8.14 g. (16.5 mmole) of trans-3-[2-benzyloxy-4-(R)-(1-methyl-4-phenylbutoxy)phenyl]-4-(2-propenyl)cycloheptanone gives in order of elution 3.14 g. (39%) of the trans-3, cis-4 isomer and 3.23 g. (40%) of the title compound.

Trans-3, Cis-4 Isomer:

[α]$_D^{25°}$ = −10.40° (C=1.058, CHCl₃)

IR (CHCl₃) 3508, 3448, 1626 and 1600 cm⁻¹.

HRMS (m/e) 498.3120 (M+, calc'd. for C₃₄H₄₂O₃: 498.3123) and 91.

PMR $\delta_{CDCl_3}^{TMS}$ 1.22 (d, J=6 Hz, methyl), 2.6 (m, benzylic methylene), 3.2 (m, benzylic methine), 4.0 (m, carbinol methine), 4.25 (m, sidechain methine), 4.6–5.0 and 5.2–6.0 (m, vinyl H), 5.02 (s, benzylic methylene), 6.4 (m, ArH), 7.20 and 7.38 (s, PhH).

Cis-3, Trans-4 Isomer:

[α]$_D^{25°}$ = −9.97° (C=1.471, CHCl₃)

IR (CHCl₃) 3508, 3448, 1626 and 1600 cm⁻¹.

HRMS (m/e) 498.3104 (M+, calc'd. for C₃₄H₄₂O₃: 498.3123), 261, 243 and 91.

PMR $\delta_{CDCl_3}^{TMS}$ 1.22 (d, J=6 Hz, methyl), 2.55 (m, benzylic methylene and methine), 3.65 (m, carbinol

EXAMPLE 30

Cis-3-[2-Benzyloxy-4-(R)-(1-methyl-4-phenylbutoxy)-phenyl]-4-trans-(3-hydroxypropyl)cycloheptanol Using the procedure of Example 5, 1.03 g. (2.07 mmole) of cis-3-[2-benzyloxy-4-(R)-(1-methyl-4-phenylbutoxy)phenyl]-4-trans-(2-propenyl)cycloheptanol gave 1.08 g. (100%) of the title compound as an oil.

$[\alpha]_D^{25°} = -9.83°$ (C=1.051, CHCl$_3$)
IR (CHCl$_3$) 3571, 3389, 1600 and 1574 cm$^{-1}$.
HRMS (m/e) 516.3216 (M+, calc'd. for C$_{34}$H$_{44}$O$_4$: 516.3228).
PMR $\delta_{CDCl_3}^{TMS}$ 1.22 (d, J=6 Hz, methyl), 2.7 (m, benzylic methylene), 3.42 (bt, CH$_2$OH), 3.85 (m, carbinol methine), 4.35 (m, sidechain methine), 5.00 (s, benzylic methylene), 6.45 (m, ArH), 7.02 (d, J=8 Hz, ArH), 7.25 and 7.42 (s, PhH).

EXAMPLE 31

Cis-3-[2-Hydroxy-4-(R)-(1-methyl-4-phenylbutoxy)-phenyl]-4-trans-(3-hydroxypropyl)cycloheptanol Using the procedure of Example 6, 1.0 g. (1.93 mmole) of cis-3-[2-benzyloxy-4-(R)-(1-methyl-4-phenylbutoxy)phenyl]-4-trans-(3-hydroxypropyl)cycloheptanol gave 500 mg. (61%) of the title compound as an oil.

$[\alpha]_D^{25°} = -7.53°$ (C=0.68, CHCl$_3$)
IR (CHCl$_3$) 3508, 3333, 1600 and 1587 cm$^{-1}$.
HRMS (m/e) 426.2758 (M+, calc'd. for C$_{27}$H$_{38}$O$_4$: 426.2760), 280, 262, 123 and 91.
PMR $\delta_{CDCl_3}^{TMS}$ 1.22 (d, J=6 Hz, methyl), 2.58 (m, benzylic methylene), 3.40 (t, J=7 Hz, CH$_2$OH), 3.8 (m, carbinol methine), 4.15 (m, sidechain methine), 6.35 (m, ArH), 6.95 (d, J=8 Hz, ArH) and 7.19 (s, PhH).

EXAMPLE 32

Cis-3-[2-Benzyloxy-4-(1,1-dimethylheptyl)phenyl]-trans-4-(2-propenyl)-1-phthalimidocycloheptane To a 25° C. mixture of 1.00 g. (2.16 mmole) of trans-3-[2-benzyloxy-4-(1,1-dimethylheptyl)phenyl]-cis-4-(2-propenyl)cycloheptanol, 476 mg. (3.24 mmole) of phthalimide and 846 mg. (3.24 mmole) of triphenylphosphine in 1.0 ml. acetonitrile was slowly added 0.51 ml. (3.24 mmole) of diethyl azodicarboxylate. The reaction mixture was stirred 5 hours and then dissolved in 250 ml. ether. The ether phase was washed once with 250 ml. water, once with 250 ml. saturated sodium chloride, dried over magnesium sulfate and evaporated to an oil. The crude oil was purified via column chromatography on 200 g. of silica gel eluted with 10% ether-hexane to yield 820 mg. (64%) of the title compound as an oil.

IR (CHCl$_3$) 1761, 1695, 1625, 1603 and 1563.
HRMS (m/e) 591.3799 (M+, calc'd. for C$_{40}$H$_{49}$NO$_3$: 591.3700), 506, 353 and 91.
PMR $\delta_{CDCl_3}^{TMS}$ 0.8 (m, terminal methyl), 1.20 (s, gem dimethyl), 2.98 (m, benzylic methine), 4.4 (bm, methine), 4.5-5.0 (m, vinyl H), 5.03 (s, benzylic methylene), 5.2-6.0 (m, vinyl H), 6.78 (m, ArH), 7.02 (d, J=8 Hz, ArH), 7.33 and 7.65 (m, ArH and PhH).

EXAMPLE 33

Cis-3-[2-Benzyloxy-4-(1,1-dimethylheptyl)phenyl]-trans-4-(2-propenyl)-1-aminocycloheptane A solution of 1.0 g. (1.68 mmole) of cis-3-[2-benzyloxy-4-(1,1-dimethylheptyl)phenyl]-trans-4-(2-propenyl)-1-phthalimidocycloheptane and 0.834 ml. (1.68 mmole) of hydrazine hydrate in 2 ml. ethanol was heated at reflux for 20 minutes forming a precipitate. The reaction was cooled, filtered and the solid washed with 200 ml. ether. The filtrate was washed once with 100 ml. saturated sodium chloride, once with 100 ml. 50% 2 N sodium hydroxide, dried over magnesium sulfate and evaporated to yield 770 mg. (99%) of the title compound as an oil.

IR (CHCl$_3$) 3125, 1695, 1632, 1600 and 1562 cm$^{-1}$.
HRMS (m/e) 461.3607 (M+, calc'd. for C$_{32}$H$_{47}$NO: 461.3646), 420, 370, 354 and 91.
PMR $\delta_{CDCl_3}^{TMS}$ 0.8 (m, terminal methyl), 1.24 (s, gem dimethyl), 2.9 (m, 2H), 4.6-5.0 (m, vinyl H), 5.04 (s, benzylic methylene), 5.2-6.1 (m, vinyl H), 6.85 (m, ArH), 7.07 (d, J=8 Hz, ArH) and 7.4 (m, PhH).

Following the procedures of Example 32 and of this example, cis-3-[2-benzyloxy-4-(1,1-dimethylheptyl)-phenyl]-trans-4-(2-propenyl)-1-aminocyclohexane is prepared from trans-3-[2-benzyloxy-4-(1,1-dimethylheptyl)phenyl]-cis-4-(2-propenyl)cyclohexanol.

EXAMPLE 34

Cis-3-[2-Benzyloxy-4-(1,1-dimethylheptyl)phenyl]-trans-4-(2-propenyl)-1-acetamidocycloheptane A mixture of 500 mg. (1.08 mmole) of cis-3-[2-benzyloxy-4-(1,1-dimethylheptyl)phenyl]-trans-4-(2-propenyl)-1-aminocycloheptane, 131 mg. (1.08 mmole) 4-N,N-dimethylaminopyridine and 0.101 ml. (1.08 mmole) of acetic anhydride in 5 ml. dichloromethane was stirred for one hour. The reaction was added to 100 ml. ether and washed twice with 100 ml. 1 N hydrochloric acid and twice with 100 ml. saturated sodium bicarbonate. The organic phase was dried over magnesium sulfate and evaporated to give 485 mg. (89%) of the title compound as an oil.

IR (CHCl$_3$) 3389, 1652, 1602 and 1562 cm$^{-1}$.
HRMS (m/e) 503.3793 (M+, calc'd. for C$_{34}$H$_{49}$NO$_2$: 503.3751), 418, 412, 353 and 91.
PMR $\delta_{CDCl_3}^{TMS}$ 0.82 (m, terminal methyl), 1.22 (s, gem dimethyl), 1.86 (s, COCH$_3$), 2.95 (m, benzylic methine), 4.02 (bm, CHN), 4.6-5.0 (m, vinyl H), 5.08 (s, benzylic methylene), 5.3-6.0 (m, vinyl H), 6.85 (m, ArH), 7.03 (d, J=8 Hz, ArH) and 7.38 (m, ArH).

EXAMPLE 35

Cis-3-[2-Benzyloxy-4-(1,1-dimethylheptyl)phenyl]-trans-4-(3-hydroxypropyl)-1-acetamidocycloheptane Using the procedure of Example 5, 1.7 g. (3.37 mmole) of cis-3-[2-benzyloxy-4-(1,1-dimethylheptyl)-phenyl]-trans-4-(2-propenyl)-1-acetamidocycloheptane gave 962 mg. (55%) of the title compound as an oil.

IR (CHCl$_3$) 3448, 1652, 1600 and 1562 cm$^{-1}$.
HRMS (m/e) 521.3813 (M+, calc'd. for C$_{34}$H$_{51}$NO$_3$: 521.3856), 430, 371 and 91.
PMR $\delta_{CDCl_3}^{TMS}$ 0.8 (m, terminal methyl), 1.20 (s, gem dimethyl, 2.85 (m, benzylic methine), 3.35 (m, CH$_2$OH), 4.0 (m, CHN), 5.05 (s, benzylic methylene), 5.38 (bd, NH), 6.8 (m, ArH), 7.00 (d, J=8 Hz, ArH) and 7.39 (bs, PhH).

EXAMPLE 36

Cis-3-[4-(1,1-Dimethylheptyl)-2-hydroxyphenyl]-trans-4-(3-hydroxypropyl)-1-acetamidocycloheptane Using the procedure of Example 6, 960 mg. (1.84 mmole) of cis-3-[2-benzyloxy-4-(1,1-dimethylheptyl)-phenyl]-trans-4-(3-hydroxypropyl)-1-acetamidocycloheptane gave 630 mg. (79%) of the title compound as an oil.

IR (CHCl$_3$) 3649, 3389, 3279, 1652, 1600 and 1562 cm$^{-1}$.

HRMS (m/e) 431.3420 (M+, calc'd. for C$_{27}$H$_{45}$NO$_3$: 431.3388), 346, 287, 257, 161, 147 and 133.

PMR $\delta_{CDCL_3}{}^{TMS}$ 0.8 (m, terminal methyl), 1.20 (s, gem dimethyl), 1.85 (s, COCH$_3$), 2.82 (m, benzylic methine), 3.42 (m, CH$_2$OH), 4.0 (m, CHN), 5.6 (bd, NH), 6.75 (m, ArH) and 6.98 (d, J=8 Hz, ArH).

By means of the procedures of Examples 34, 35 and this example, cis-3-[4-(1,1-dimethylheptyl)-2-hydroxyphenyl]-trans-(3-hydroxypropyl)-1-acetamidocyclohexane is prepared from cis-3-[2-benzyloxy-4-(1,1-dimethylheptyl)phenyl]-trans-(2-propenyl)-1-aminocyclohexane.

EXAMPLE 37

Cis-3-[2-Benzyloxy-4-(1,1-dimethylheptyl)phenyl]-trans-4-(3-hydroxypropyl)cyclohexanol bis-d-mandelate A mixture of 31.3 g. (67.2 mmole) of cis-3-[2-benzyloxy-4-(1,1-dimethylheptyl)phenyl]-trans-4-(3-hydroxypropyl)cyclohexanol, 25.5 g. (168 mmole) of d-mandelic acid and 1.0 g. (5.26 mmole) of p-toluenesulfonic acid monohydrate in 500 ml. of benzene was heated at reflux for 11 hours. Water was removed by use of a soxhlet extractor filled with 200 g. of 3A molecular sieves. The reaction is cooled, added to one liter saturated sodium bicarbonate and extracted with four 500 ml. portions of ether. The combined organic extract was dried over magnesium sulfate and evaporated to an oil. The crude oil was purified via column chromatography on 2 kg. of silica gel eluted with 40-50% etherhexane to yield in order of elution 18 g. (37%) of diastereomer A and 21 g. (43%) of diastereomer B of the title compound.

Diastereomer A
m.p.: 111°-112.5° C. (methanol)
$[\alpha]_D{}^{25°} = +20.19$ (C, =1.107, 5% chloroform-methanol)
PMR (CDCl$_3$)$\delta$0.84 (m, terminal methyl), 1.25 (s, gem dimethyl), 2.8 (m, benzylic methine), 3.45 (m), 4.0 (m), 4.6-5.2 (m), 5.05 (s, benzylic methylene), 6.88 (m, ArH), 7.27 and 7.34 (s, PhH).

Analysis: Calc'd. for C$_{47}$H$_{58}$O$_7$: C, 76.81; H, 7.95. Found: C, 76.49; H, 7.76.

In like manner, but using the same relative stoichiometric proportion of d-mandelic acid and p-toluenesulfonic acid monohydrate, 9.0 g. (16 mmole) of cis-3-[2-Benzyloxy-4-(1,1-dimethylheptyl)phenyl]-trans-4-(3-benzyloxypropyl)cyclohexanol gave, in order of elution, 4.1 g. (37%) of diastereomer A and 4.2 g. (38%) of diastereomer B of cis-3-[2-benzyloxy-4-(1,1-dimethylheptyl)phenyl]-trans-4-(3-benzyloxypropyl)-1-d-mandeloyloxycyclohexane as solids.

Diastereomer A:
m.p.: 56°-58° C.
$[\alpha]_D{}^{25°} = 0.292°$ (C=1.25, CH$_3$OH)
PMR $\delta_{CDCl_3}{}^{TMS}$ 0.80 (m, terminal methyl), 1.20 (s, gem dimethyl), 2.9 (m), 3.0-3.6 (m), 4.30 (s, benzylic methylene), 4.5-5.1 (m), 5.00 (s, benzylic methylene), 6.78 (m, ArH), 6.98 (d, J=8 Hz, ArH), 7.17 (s, PhH) and 7.30 (s, PhH).

Diastereomer B:
m.p.: 65°-69° C.
$[\alpha]_D{}^{25°} = +40.95°$ (C=1.21, CH$_3$OH)
PMR $\delta_{CDCl_3}{}^{TMS}$ 0.80 (m, terminal methyl), 1.20 (s, gem dimethyl), 2.8 (m), 3.0-3.5 (m), 4.26 (s, benzylic methylene), 4.4-5.1 (m), 4.95 (s, benzylic methylene), 6.70 (m, ArH), 6.87 (d, J=8 Hz), 7.12 (s, PhH) and 7.20 (s, PhH).

EXAMPLE 38

Enantiomer A of Cis-3-[2-Benzyloxy-4-(1,1-dimethylheptyl)phenyl]-trans-4-(3-hydroxypropyl)cyclohexanol A mixture of 18 g. (24.5 mmole) of diastereomer A of cis-3-[2-benzyloxy-4-(1,1-dimethylheptyl)phenyl]-trans-4-(3-hydroxypropyl)cyclohexanol bis-d-mandelate and 13.5 g. (98.1 mmole) of potassium carbonate in 250 ml. methanol, 175 ml. tetrahydrofuran and 35 ml. water was stirred for 24 hours. The reaction was added to one liter saturated sodium chloride and extracted twice with 500 ml. portions of ether. The combined organic extract was dried over magnesium sulfate and evaporated to a quantitative yield of the title compound as an oil.

$[\alpha]_D{}^{25°} = -34.51°$ (C. =1.083, methanol)
PMR $\delta_{CDCl_3}{}^{TMS}$ 0.82 (m, terminal methanol), 1.25 (s, gem dimethyl), 2.90 (m, benzylic methine), 3.40 (bt, CH$_2$OH), 3.7 (m, carbinol methine), 5.06 (s, benzylic methylene), 6.82 (d, J=2 Hz, ArH), 6.82 (dd, J=8 and 2 Hz, ArH), 7.00 (d, J=8 Hz, ArH) and 7.32 (s, PhH).

Using the above procedure, 4.00 g. (5.79 mmole) of cis-3-[2-benzyloxy-4-(1,1-dimethylheptyl)phenyl]-trans-4-(3-benzyloxypropyl)-1-d-mandeloyloxycyclohexane, diastereomer A, gave a quantitative yield of cis-3-[2-benzyloxy-4-(1,1-dimethylheptyl)phenyl]-trans-4-(3-benzyloxypropyl)cyclohexanol, enantiomer A, as an oil.
$[\alpha]_D{}^{25°} = -24.92°$ (C =1.23, CH$_3$OH)
PMR $\delta_{CDCl_3}{}^{TMS}$ 0.82 (m, terminal methyl), 1.22 (s, gem dimethyl), 2.9 (m, benzylic methine), 3.23 (bt, J=6 Hz, methylene), 3.7 (m, carbinol methine), 4.35 and 5.00 (s, benzylic methylenes), 6.82 (m, ArH), 7.02 (d, J=8 Hz), ArH), 7.19 and 7.35 (s, PhH).

EXAMPLE 39

Enantiomer B of Cis-3-[2-Benzyloxy-4-(1,1-dimethylheptyl)phenyl]-trans-4-(3-hydroxypropyl)cyclohexanol a. Using the procedure of Example 38, 21 g. (28.6 mmole) of diastereomer B of cis-3[2-benzyloxy-4-(1,1-dimethylheptyl)phenyl]-trans-4-(3-hydroxypropyl)cyclohexanol bis-d-mandelate gave 13 g. (98%) of the title compound as an oil.

$[\alpha]_D{}^{25°} = +26.30°$ (C=1.051, CH$_3$OH)

b. Using the procedure of Example 37, 13 g. (27.8 mmole) of the title compound and 10.6 g. (69.7 mmole) of 1-mandelic acid gave 8 g. (39%) of diastereomer A of cis-3-[2-benzyloxy-4-(1,1-dimethylheptyl)phenyl]-trans-4-(3-hydroxypropyl)cyclohexanol bis-1-mandelate.
m.p. 106°-107.5° C. (methanol)
PMR $\delta_{CDCl_3}{}^{TMS}$ 0.83 (terminal methyl), 1.25 (s, gem dimethyl), 2.85 (m, benzylic methine), 3.40 (m), 4.0 (m), 4.7-5.1 (m), 5.07 (s, benzylic methylene).

Analysis: Calc'd. for C$_{47}$H$_{58}$O$_7$: C, 76.81; H, 7.95. Found: C, 76.69; H, 7.86.

c. Using the procedure of Example 38, 8.0 g. (10.9 mmole) of diastereomer A of cis-3-[2-benzyloxy-4-(1,1-dimethylheptyl)phenyl]-trans-4-(3-hydroxypropyl) cyclohexanol bis-1-mandelate gives 4.7 g. (93%) of the title compound.

$[\alpha]_D^{25°} = +34.17°$ (C. =1.15, CH$_3$OH)

PMR $\delta_{CDCl_3}{}^{TMS}$ 0.86 (m, terminal methyl), 1.28 (s, gem dimethyl), 2.82 (m, benzylic methine), 3.42 (bt, CH$_2$OH), 3.7 (m, carbinol methine), 5.10 (s, benzylic methylene), 6.9 (m, ArH), 7.10 (d, J=8 Hz, ArH) and 7.40 (s, PhH).

EXAMPLE 40

Cis-3-[4-(1,1-Dimethylheptyl)-2-hydroxyphenyl]-trans-4-(3-hydroxypropyl)cyclohexanol, Enantiomer A Using the procedure of Example 6, 11.4 g. (24.5 mmole) of enantiomer A of cis-3-[2-benzyloxy-4-(1,1-dimethylheptyl)phenyl]-trans-4-(3-hydroxypropyl)cyclohexanol gave 8.5 g. (93%) of the title compound.

m.p. 65°-72° C. (hexane-dichloromethane)

$[\alpha]_D^{25°} = -39.24°$ (C=1.00, CH$_3$OH)

HRMS (m/e) 376.2938 (M+, calc'd. for C$_{24}$H$_{40}$O$_3$: 376.2967), 304, 273, 255, 199, 147 and 121.

PMR $\delta_{CDCl_3}{}^{TMS}$ 0.83 (m, terminal methyl), 1.23 (s, gem dimethyl), 2.83 (m, benzylic methine), 3.58 (bt, CH$_2$OH), 3.7 (m, carbinol methine), 6.9 (m, ArH) and 7.00 (d, J=8 Hz, ArH).

EXAMPLE 41

Cis-3-[4-(1,1-Dimethylheptyl)-2-hydroxyphenyl]-trans-4-(3-hydroxypropyl)cyclohexanol, Enantiomer B Using the procedure of Example 6, 4.7 g. (10.1 mmole) of enantiomer B of cis-3-[2-benzyloxy-4-(1,1-dimethylheptyl)phenyl]-trans-4-(3-hydroxypropyl)cyclohexanol gave 3.5 g. (92%) of the title compound as an oil.

$[\alpha]_D^{25°} = +36.47°$ (C=0.947, CH$_3$OH)

HRMS (m/e) 376.2942 (M+, calc'd. for C$_{24}$H$_{40}$O$_3$: 376.2967), 358, 291, 273 and 147.

PMR (CDCl$_3$) $\delta$0.82 (s, terminal methyl), 1.2 (s, gem dimethyl), 2.7 (m, benzylic methine), 3.41 (bt, J=7 Hz, carbinol methylene), 3.78 (m, carbinol methine), 6.77 (m, ArH) and 7.00 (d, J=8 Hz, ArH).

EXAMPLE 42

Trans-3-[2-Benzyloxy-4-(1,1-dimethylheptyl)phenyl]5-cyanocyclohexanone

To a refluxing solution of 3.99 g. (9.87 mmole) of 5-[2-benzyloxy-4-(1,1-dimethylheptyl)phenyl]-2-cyclohexen-1-one in 6.65 ml. of ethyl acetate was added a hot solution of 800 mg. (11.9 mmole) of potassium cyanide in 2 ml. water and 2.3 ml. ethanol. The reaction was refluxed 2 hours and then another 2.74 mmole of potassium cyanide added. The reaction was refluxed one hour longer and then cooled and added to 400 ml. saturated sodium chloride-400 ml. ether. The ether extract was dried over magnesium sulfate and evaporated to yield an oil. The crude oil was purified via column chromatography on 160 g. of silica gel eluted with 10% acetone-hexane to yield 3.02 g. (71%) of the title compound.

m.p. 79° C. (petroleum ether)

IR (CHCl$_3$) 2202, 1706, 1600 and 1552 cm$^{-1}$.

MR (m/e) 431 (M+), 414, 403, 346, 340 and 91.

EXAMPLE 43

Trans-3-[2-Benzyloxy-4-(1,1-dimethylheptyl)phenyl-cis-5-cyanocyclohexanol

Using the procedure of Example 2, 3.02 g. (7.00 mmole) of trans-3-[2-benzyloxy-4-(1,1-dimethylheptyl)-phenyl]-5-cyanocyclohexanone was reduced to 2.66 g. (88%) of the title compound.

m.p. 94°-102° C. (pentane)

IR (CHCl$_3$) 3413, 2222, 1612 and 1575 cm$^{-1}$.

MS (m/e) 433 (M+).

EXAMPLE 44

Trans-3-[2-Benzyloxy-4-(1,1-dimethylheptyl)phenyl]-trans-5-cyanocyclohexanol

A mixture of 3.12 g. (7.20 mmole) of trans-3-[2-benzyloxy-4-(1,1-dimethylheptyl)phenyl]-cis-5-cyanocyclohexanol and 808 mg. (7.20 mmole) of potassium t-butoxide in 70 ml. of t-butanol was refluxed for 2.5 hours. The t-butanol was evaporated on a rotovapor and the residue diluted with saturated sodium chloride. The quenched residue was extracted with ether, the extract dried over magnesium sulfate and evaporated to yield an oil. The crude oil was purified via column chromatography on 124 g. of silica gel eluted with 10% acetonehexane to yield 1.53 g. (44%) of the title compound.

m.p. 62°-64° C. (petroleum ether)

IR (CHCl$_3$) 2247, 1597 and 1579 cm$^{-1}$.

MS (m/e) 433 (M+), 348, 342, 305 and 91.

PMR $\delta_{CDCl_3}{}^{TMS}$ 0.83 (m, terminal methyl), 2.8–3.9 (two methines), 4.25 (m, carbinol methine), 5.12 (s, benzylic methylene), 6.9 (m, ArH), 7.06 (d, J=8 Hz), ArH) and 7.4 (s, PhH).

EXAMPLE 45

Cis-3-[2-Benzyloxy-4-(1,1-dimethylheptyl)phenyl]-5-cyanocyclohexanone

To a 0° C. solution of 1.43 g. (3.30 mmole) of trans-3-[2-benzyloxy-4-(1,1-dimethylheptyl)phenyl]-trans-5-cyanocyclohexanol in 25 ml. of acetone was added 2.37 ml. (6.6 mmole) of Jones's Reagent. The reaction was stirred 20 minutes at 0° C. and then quenched by the addition of 1 ml. of isopropanol. The quenched reaction was added to 700 ml. saturated sodium chloride and extracted with 300 ml. of ether. The ether extract was dried over magnesium sulfate and evaporated to yield 1.31 g. (92%) of the title compound as an oil.

IR (CHCl$_3$) 2247, 1733, 1623 and 1584 cm$^{-1}$.

MS (m/e) 431 (M+), 416, 404, 362, 347, 340 and 91.

PMR $\delta_{CDCl_3}{}^{TMS}$ 0.83 (m, terminal methyl), 1.24 (s, gem dimethyl), 2.0–3.7 (m), 5.10 (s, benzylic methylene), 6.95 (m, ArH), 7.02 (d, J=8 Hz) and 7.38 (s, ArH).

EXAMPLE 46

Cis-3-[2-Benzyloxy-4-(1,1-dimethylheptyl)phenyl]-cis-5-cyanocyclohexanol

Using the procedure of Example 2, 1.11 g. (2.58 mmole) of cis-3-[2-benzyloxy-4-(1,1-dimethylheptyl)-phenyl]-5-cyanocyclohexanone gave 949 mg. (84%) of the title compound as an oil.

IR (CHCl$_3$) 3571, 3389, 2232, 1612 and 1574 cm$^{-1}$.

PMR $\delta_{CDCl_3}{}^{TMS}$ 0.83 (m, terminal methyl), 1.25 (s, gem dimethyl), 3.70 (m, carbinol methine), 5.10 (s, ben-

EXAMPLE 47

Cis-3-[4-(1,1-Dimethylheptyl)-2-hydroxyphenyl]-5-cyanocyclohexanone

Using the procedure of Example 6, 200 mg. (0.462 mmole) of cis-3-[2-benzyloxy-4-(1,1-dimethylheptyl)phenyl]-5-cyanocyclohexanone was converted to 133 mg. (84%) of the title compound.

m.p. 111°–112° C. (ether-petroleum ether)

IR (CHCl$_3$) 3571, 3300, 2237, 1724, 1626 and 1577 cm$^{-1}$.

MS (m/e) 341 (M+), 256, 239 and 229.

Analysis: Calc'd. for $C_{22}H_{31}NO_2$: C, 77.38; H, 9.15; N, 4.10. Found: C, 76.89; H, 9.05; N, 4.14.

EXAMPLE 48

Cis-3-[4-(1,1-Dimethylheptyl)-2-hydroxyphenyl]-cis-5-cyanocyclohexanol

Using the procedure of Example 6, 235 mg. (0.542 mmole) of cis-3-[2-benzyloxy-4-(1,1-dimethylheptyl)phenyl]-cis-5-cyanocyclohexanol gave 74.5 mg. (40%) of the title compound.

m.p. 165° C. (dichloromethane-petroleum ether)

IR (KBr) 3225, 2232, 1618 and 1582 cm$^{-1}$.

MS (m/e) 343 (M+), 299, 258, 241 and 213 cm$^{-1}$.

PMR (CDCl$_3$, D$_6$-DMSO) δ0.83 (m, terminal methyl), 1.22 (s, gem dimethyl), 3.65 (m, carbinol methine), 6.77 (m, ArH) and 7.00 (d, J=8 Hz, ArH).

Analysis: Calc'd for $C_{22}H_{33}NO_2$: C, 76.92; H, 9.68; N, 4.08. Found: C, 76.51; H, 9.23; H, 3.95.

EXAMPLE 49

Cis-3-[2-Benzyloxy-4-(1,1-dimethylheptyl)phenyl]-5-cis-hydroxycyclohexane carboxaldehyde To a −65° C. solution of 704 mg. (1.62 mmole) of cis-3-[2-benzyloxy-4-(1,1-dimethylheptyl)phenyl]-cis-5-cyanocyclohexanol in 30 ml. toluene was added 3.40 ml. (3.4 mmole) of diisobutylaluminum hydride (1 M in toluene). The reaction was allowed to warm to −5° C. and was then poured onto dilute sulfuric acid and ice. The quenched reaction was extracted with ether, the extract dried over magnesium sulfate and evaporated to give a quantitative yield of the title compound as an oil.

IR (CHCl$_3$) 3165, 1730, 1612 and 1574 cm$^{-1}$.

MS (m/e) 436 (M+), 408 and 350.

PMR $\delta_{CDCl_3}^{TMS}$ 0.83 (m, terminal methyl), 1.23 (s, gem dimethyl), 3.7 (m, carbinol methine), 5.11 (s, benzylic methylene), 6.85 (m, ArH), 7.35 (m, PhH) and 9.60 (bs, CHO).

EXAMPLE 50

Cis-3-[2-Benzyloxy-4-(1,1-dimethylheptyl)phenyl]-cis-5-hydroxymethylcyclohexanol Using the procedure of Example 2, 700 mg. (1.60 mmole) of cis-3-[2-benzyloxy-4-(1,1-dimethylheptyl)phenyl]-5-cis-hydroxycyclohexane carboxaldehyde was converted to 208 mg. (30%) of the title compound as an oil.

MS (m/e) 438 (M+)

PMR $\delta_{CDCl_3}^{TMS}$ 0.83 (m, terminal methyl), 1.23 (s, gem dimethyl), 2.7–4.0 (m, 4H), 5.09 (s, benzylic methylene), 6.90 (m, ArH), 7.10 (d, J=8 Hz, ArH) and 7.38 (s, PhH).

EXAMPLE 51

Cis-3-[4-(1,1-Dimethylheptyl)-2-hydroxyphenyl]-cis-5-hydroxymethylcyclohexanol

Using the procedure of Example 6, 208 mg. (0.475 mmole) of cis-3-[2-benzyloxy-4-(1,1-dimethylheptyl)phenyl]-cis-5-hydroxymethylcyclohexanol was hydrogenolyzed to 127 mg. (77%) of the title compound.

m.p. 126°–127° C. (ether-petroleum ether)

IR (CHCl$_3$) 3597, 3333, 1623 and 1587 cm$^{-1}$.

HRMS (m/e) 348.2662 (M+, calc'd. for $C_{22}H_{36}O_3$: 348. 2655), 330, 299, 287, 263 and 245.

PMR (CDCl$_3$, D$_6$-DMSO) δ0.85 (m, terminal methyl), 1.25 (s, gem dimethyl), 3.5 (m, carbinol methylene), 3.8 (m, carbinol methine), 6.8 (m, ArH) and 7.07 (d, J=8 Hz, ArH).

EXAMPLE 52

7-Oxabicyclo[4.1.0]-4-[2-benzyloxy-4-(1,1-dimethylheptyl)phenyl]-2-heptanone

To a 0° C. solution of 3.24 g. (8.01 mmole) of 5-[2-benzyloxy-4-(1,1-dimethylheptyl)phenyl]-2-cyclohexen-1-one and 2.3 ml. (24 mmole) of 30% hydrogen peroxide in 80 ml. methanol was added dropwise 0.66 ml. (3.96 mmole) of 6 N sodium hydroxide. The reaction was stirred one hour longer at 0° C. and then added to 1000 ml. saturated sodium chloride. The quenched reaction was extracted with 500 ml. of ether, the extract dried over magnesium sulfate and evaporated to yield 3.02 g. of crude product. The crude product was purified via column chromatography on 200 g. of silica gel eluted with 20% ether-petroleum ether to yield in order to elution 237 mg. (7%) of the cis isomer, 1.72 g. (51%) of a mixture and 1.01 g. (30%) of the trans isomer of title compound. Column chromatography of the mixed fraction on 300 g. of silica gel eluted with 10% ether-petroleum ether yielded 34 mg. (1%) of cis isomer and 1.56 g. (46%) of the trans isomer of title compound, both as oils.

Cis Isomer:

IR (CHCl$_3$) 1718, 1626 and 1582 cm$^{-1}$.

MS (m/e) 420 (M+), 404, 335, 312, 206 and 91.

PMR $\delta_{CDCl_3}^{TMS}$ 0.83 (m, terminal methyl), 1.27 (s, gem dimethyl), 2.0–2.5 (m), 2.9–3.7 (m), 5.15 (s, benzylic methylene), 6.9 (m, ArH), 7.10 (d, J=8 Hz, ArH) and 7.41 (s, PhH).

Trans Isomer:

IR (CHCl$_3$) 1718, 1623 and 1577 cm$^{-1}$.

MS (m/e) 420 (M+) , 404, 335, 329, 316, 257 and 91.

PMR $\delta_{CDCl_3}^{TMS}$ 0.83 (m, terminal methyl), 1.26 (s, gem dimethyl), 2.0–2.8 (m), 3.3 (m), 3.4–4.0 (m), 5.13 (s, benzylic methylene), 6.9 (m, ArH), 7.07 (d, J=8 Hz, ArH) and 7.41 (s, PhH).

In like manner, the cis- and trans-isomers of 8-oxabicyclo[5.1.0]-4-[2-benzyloxy-4-(1,1-dimethylheptyl)phenyl]-2-octanone are prepared from 6-[2-benzyloxy-4-(1,1-dimethylheptyl)phenyl]cyclohept-3-en-1-one.

EXAMPLE 53

3-[2-Benzyloxy-4-(1,1-dimethylheptyl)phenyl]-cis-5-hydroxycyclohexanone

To a solution of 267 mg. (0.635 mmole) of the cis-isomer of 7-oxabicyclo[4.1.0]-4-[2-benzyloxy-4-(1,1-dimethylheptyl)phenyl]-2-heptanone in 20 ml. of 10% aqueous tetrahydrofuran was added 220 mg. of aluminum amalgam (prepared by washing 1 cm. strips of aluminum foil 15 seconds each in 2 N sodium hydroxide, water, 0.5% mercuric chloride, water, 2 N sodium hydroxide, water, 0.5% mercuric chloride, water, ethanol and ether). The reaction was stirred 3 hours at 25° C. and then filtered through diatomaceous earth. The filtrate was evaporated on a rotovapor and the residue dissolved in ether, dried over magnesium sulfate and evaporated. The residue was purified via preparative layer chromatography on two 20 cm.×20 cm.×2 mm. silica gel plates eluted with ether to yield 156 mg. (58%) of the title compound as an oil.

IR (CHCl$_3$) 3597, 3546, 1718, 1612 and 1577 cm$^{-1}$.

MS (m/e) 422, 404, 337, 331, 319, 313 and 310.

PMR $\delta_{CDCl_3}{}^{TMS}$ 0.81 (m, terminal methyl), 1.22 (s, gem dimethyl), 3.2 (m, benzylic methine), 3.95 (m, carbinol methine), 5.02 (s, benzylic methylene), 6.9 (m, ArH), 7.03 (d, J=8 Hz, ArH) and 7.38 (s, PhH).

EXAMPLE 54

3-[2-Benzyloxy-4-(1,1-dimethylheptyl)phenyl]-trans-5-hydroxycyclohexanone

Using the procedure of Example 53, 1.47 g. (3.5 mmole) of the trans isomer of 7-oxabicyclo[4.1.0]-4-[2-benzyloxy-4-(1,1-dimethylheptyl)phenyl]-2-heptanone gave 1.25 g. (84%) of the title compound.

m.p. 95° C. (pentane)

IR (CHCl$_3$) 3636, 3448, 1724, 1626 and 1587 cm$^{-1}$.

MS (m/e) 422 (M+), 404, 337, 331, 319, 313 and 91.

PMR $\delta_{CDCl_3}{}^{TMS}$ 0.85 (m, terminal methyl), 1.25 (s, gem dimethyl), 2.15 (m), 2.3-2.8 (m), 3.9 (m, benzylic methine), 4.5 (m, carbinol methine), 5.12 (s, benzylic methylene), 6.9 (m, ArH), 7.08 (d, J=8 Hz, ArH) and 7.40 (bs, PhH).

In like manner, reduction of the cis- and trans-isomers of 8-oxabicyclo[5.1.0]-4-[2-benzyloxy-4-(1,1-dimethylheptyl)phenyl]-2-octanone affords the corresponding cis- and -trans 5-hydroxy derivatives.

EXAMPLE 55

Cis-3-[2-Benzyloxy-4-(1,1-dimethylheptyl)phenyl]-trans-5-cyclohexan-1,5-diol, and the trans-3-cis-5 Isomer Using the procedure of Example 2, 629 mg. (1.49 mmole) of 3-[2-benzyloxy-4-(1,1-dimethylheptyl)-phenyl]-trans-5-hydroxycyclohexanone (Example 54) gave 237 mg. (38%) of the trans-3 cis-5 isomer and 385 mg. (61%) of the trans-5 isomer of title compound.

Cis-5 Isomer:

HRMS (m/e) 424.3002 (M+, calc'd. for C$_{28}$H$_{40}$O$_3$: 424.2927)

PMR $\delta_{CDCl_3}{}^{TMS}$ 0.83 (m, terminal methyl), 1.26 (s, gem dimethyl), 4.25 (m, carbinol methine), 5.13 (s, benzylic methylene), 6.9 (m, ArH), 7.12 (d, J=8 Hz) and 7.41 (m, PhH).

Trans-5 Isomer:

HRMS (m/e) 424.2992 (M+, calc'd for C$_{28}$H$_{40}$O$_3$: 424.2927), 339, 231, 213 and 91.

PMR $\delta_{CDCl_3}{}^{TMS}$ 0.83 (m, terminal methyl), 1.25 (s, gem dimethyl), 3.0-4.4 (m, 3H), 5.10 (s, benzylic methylene), 6.88 (d, J=2 Hz, ArH), 6.88 (dd, J=8 and 2 Hz, ArH), 7.10 (d, J=8 Hz, ArH) and 7.40 (m, PhH).

EXAMPLE 56

Cis-3-[2-Benzyloxy-4-(1,1-dimethylheptyl)phenyl]-cis-5-cyclohexan-1,5-diol, and the cis-3-trans-5 Isomer Using the procedure of Example 2, 203 mg. (0.481 mmole) of 3-[2-benzyloxy-4-(1,1-dimethylheptyl)-phenyl]-cis-5-hydroxycyclohexanone (Example 54) was reduced to 25 mg. (12%) of the cis-3 trans-5 isomer of title compound and 132 mg. (65%) of the title compound.

Cis-3-cis-5 Isomer:

HRMS 424.2974 (M+, calc'd. for C$_{28}$H$_{40}$O$_3$: 424.2927), 339, 298, 231, 213 and 91.

The remaining compounds of Example 54 are reduced to corresponding cycloheptandiols in like manner.

EXAMPLE 57

Cis-3-[4-(1,1-dimethylheptyl)-2-hydroxyphenyl]-cis-5-cyclohexan-1,5-diol

Using the procedure of Example 6, 132 mg. (0.311 mmole) of cis-3-[2-benzyloxy-4-(1,1-dimethylheptyl)-phenyl]-cis-5-cyclohexan-1,5-diol was converted to 72 mg. (69%) of the title compound.

m.p. 128° C. (ether-pentane)

HRMS (m/e) 334.2517 (M+, calc'd. for C$_{21}$H$_{34}$O$_3$: 334.2483), 298, 249, 231 and 213.

PMR $\delta_{CDCl_3}{}^{TMS}$ 0.83 (t, terminal methyl), 1.24 (s, gem dimethyl), 2.94 (m, benzylic methine), 3.35, 3.11 (bs, OH), 3.47-3.97 (m, carbinol methines), 6.72 (m, ArH) and 7.00 (d, J=8 Hz, ArH).

EXAMPLE 58

Cis-3-[4-(1,1-Dimethylheptyl)-2-hydroxyphenyl]-trans-5-cyclohexan-1,5-diol

Using the procedure of Example 6, 385 mg. (0.908 mmole) of cis-3-[2-benzyloxy-4-(1,1-dimethylheptyl)-phenyl]-trans-5-cyclohexan-1,5-diol gave 162 mg. (53%) of the title compound.

m.p. 170° C. (dichloromethane)

HRMS (m/e) 334.2513 (M+, calc'd. for C$_{21}$H$_{34}$O$_3$: 334.2483), 298, 249, 231 and 213.

PMR (100 MHz, CDCl$_3$, D$_6$-DMSO) δ0.81 (m, terminal methyl), 1.23 (s, gem dimethyl), 3.38 (m, benzylic methine), 3.9-4.3 (m, carbinol methines), 6.74 (m, ArH) and 7.00 (d, J=8 Hz, ArH).

EXAMPLE 59

Trans-3-[4-(1,1-Dimethylheptyl)-2-hydroxyphenyl]-cis-5-cyclohexan-1,5-diol

Using the procedure of Example 6, 237 mg. (0.558 mmole) of trans-3-[2-benzyloxy-4-(1,1-dimethylheptyl)-phenyl]-cis-5-cyclohexan-1,5-diol gave 107 mg. (57%) of the title compound.

m.p. 126°-127° C. (ether-pentane)

HRMS (m/e) 334.2503 (M+, calc'd. for C$_{21}$H$_{34}$O$_3$: 334.2483), 316, 298, 249 and 231.

PMR (100 MHz, CDCl$_3$, D$_6$-DMSO) δ0.83 (m, terminal methyl), 1.24 (s, gem dimethyl), 3.82 (m, benzylic methine), 4.29 (m, carbinol methines), 6.88 (m, ArH) and 7.06 (d, J=8 Hz, ArH).

In like manner, the cycloheptandiols of Example 56 are debenzylated.

EXAMPLE 60

The following compounds are prepared according to the procedure of Example 1 from the appropriate 1-bromo-2-benzyloxy-4-(Z-W)benzenes and the appropriate 4-(and 5)-2-cycloalken-1-one.

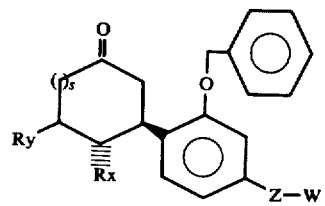

| s | Rx | Ry | Z | W |
|---|---|---|---|---|
| 1 | $CH_2-CH=CH_2$ | H | $(CH_2)_7$ | H |
| 1 | $CH_2-CH=CH_2$ | H | $(CH_2)_{11}$ | H |
| 1 | $CH_2-CH=CH_2$ | H | $[CH(CH_3)]_2(CH_2)_5$ | H |
| 1 | $(CH_2)_2CH=CH_2$ | H | $C(CH_3)_2(CH_2)_4$ | H |
| 1 | $(CH_2)_2CH=CH_2$ | H | $(CH_2)_8$ | H |
| 1 | $(CH_2)_3CH=CH_2$ | H | $C(CH_3)_2(CH_2)_6$ | H |
| 1 | $(CH_2)_4CH=CH_2$ | H | $C(CH_3)_2(CH_2)_6$ | H |
| 1 | $CH_2CH=CH_2$ | H | $(CH_2)_3$ | $C_6H_5$ |
| 1 | $(CH_2)_4CH=CH_2$ | H | $[CH(CH_3)]_2(CH_2)_5$ | H |
| 1 | $CH_2CH=CH_2$ | H | $(CH_2)_4$ | $4-FC_6H_4$ |
| 1 | $(CH_2)_2CH=CH_2$ | H | $CH(CH_3)(CH_2)_3$ | $4-ClC_6H_4$ |
| 1 | $(CH_2)_3CH=CH_2$ | H | $CH(CH_3)(CH_2)_3$ | $C_6H_5$ |
| 1 | $CH_2CH=CH_2$ | H | $CH(CH_3)(CH_2)_3$ | $C_6H_5$ |
| 1 | $(CH_2)_3CH=CH_2$ | H | $CH(C_2H_5)(CH_2)_4$ | $4-FC_6H_4$ |
| 1 | $(CH_2)_3CH=CH_2$ | H | $C(CH_3)_2(CH_2)_4$ | $C_6H_5$ |
| 1 | $CH_2CH=CH_2$ | H | $(CH_2)_4$ | 4-pyridyl |
| 1 | $CH_2CH=CH_2$ | H | $(CH_2)_8$ | $C_6H_5$ |
| 1 | $CH_2CH=CH_2$ | H | $CH(CH_3)(CH_2)_3$ | 2-pyridyl |
| 1 | $(CH_2)_3CH=CH_2$ | H | $(CH_2)_{11}$ | H |
| 2 | $CH_2CH=CH_2$ | H | $[CH(CH_3)]_2(CH_2)_5$ | H |
| 2 | $CH_2CH=CH_2$ | H | $(CH_2)_7$ | H |
| 2 | $(CH_2)_2CH=CH_2$ | H | $C(CH_3)_2(CH_2)_6$ | H |
| 2 | $(CH_2)_3CH=CH_2$ | H | $[CH(CH_3)]_2(CH_2)_5$ | H |
| 1 | $CH_2CH=CH_2$ | H | $(CH_2)_4$ | $C_6H_5$ |
| 1 | $CH_2CH=CH_2$ | H | $CH(CH_3)(CH_2)_5$ | $C_6H_5$ |
| 1 | $CH_2CH=CH_2$ | H | $CH(CH_3)(CH_2)_3$ | $C_6H_5$ |
| 1 | $CH_2CH=CH_2$ | H | $CH(CH_3)(CH_2)_3$ | $4-FC_6H_4$ |
| 1 | $CH_2CH=CH_2$ | H | $OCH(CH_3)(CH_2)_3$ | $C_6H_5$ |
| 1 | $(CH_2)_4CH=CH_2$ | H | $OCH(CH_3)(CH_2)_3$ | 4-pyridyl |
| 1 | $(CH_2)_2CH=CH_2$ | H | $O(CH_2)_7$ | $4-ClC_6H_4$ |
| 1 | $CH_2CH=CH_2$ | H | $(CH_2)_4OCH_2$ | $C_6H_5$ |
| 1 | $(CH_2)_3CH=CH_2$ | H | $(CH_2)_6O$ | $C_6H_5$ |
| 1 | $CH_2CH=CH_2$ | H | $(CH_2)_5$ | H |
| 1 | $CH_2CH=CH_2$ | H | $(CH_2)_{13}$ | H |
| 1 | $CH_2CH=CH_2$ | H | $O(CH_2)_3$ | $C_6H_5$ |
| 1 | $(CH_2)_4CH=CH_2$ | H | $[CH(CH_3)]_2CH_2$ | 4-pyridyl |
| 2 | $CH_2CH=CH_2$ | H | $CH(CH_3)(CH_2)_4$ | 4-pyridyl |
| 2 | $(CH_2)_3CH=CH_2$ | H | $(CH_2)_7$ | 4-pyridyl |
| 1 | $CH_2CH=CH_2$ | H | $O(CH_2)_7$ | H |
| 1 | $CH_2CH=CH_2$ | H | $O(CH_2)_{11}$ | H |
| 1 | $(CH_2)_3CH=CH_2$ | H | $OC(CH_3)_2(CH_2)_5$ | H |
| 1 | $CH_2CH=CH_2$ | H | $(CH_2)O(CH_2)_7$ | H |
| 1 | $(CH_2)_4CH=CH_2$ | H | $(CH_2)_{11}O$ | H |
| 1 | $(CH_2)_2CH=CH_2$ | H | $(CH_2)_3O(CH_2)_4$ | H |
| 1 | $CH_2CH=CH_2$ | H | $O(CH_2)_4$ | $C_6H_5$ |
| 2 | H | $CH_2CH=CH_2$ | $C(CH_3)_2(CH_2)_6$ | H |
| 2 | H | $CH_2CH=CH_2$ | $(CH_2)_{11}$ | H |
| 2 | H | $CH_2CH=CH_2$ | $[CH(CH_3)]_2(CH_2)_3$ | H |
| 2 | H | $CH_2CH=CH_2$ | $(CH_2)_{11}O$ | H |
| 2 | H | $CH_2CH=CH_2$ | $(CH_2)_5$ | H |
| 2 | H | $CH_2CH=CH_2$ | $O(CH_2)_{13}$ | H |
| 2 | H | $CH_2CH=CH_2$ | $(CH_2)O(CH_2)_7$ | $4-ClC_6H_4$ |
| 1 | $(CH_2)_2CH=CH_2$ | $CH_2CH=CH_2$ | $(CH_2)_3OCH(CH_3)$ | 2-pyridyl |
| 1 | $CH_2CH=CH_2$ | H | $O(CH_2)_5$ | 3-pyridyl |
| 2 | $CH_2CH=CH_2$ | H | $OCH(CH_3)(CH_2)_5$ | H |
| 2 | $CH_2CH=CH_2$ | H | $O(CH_2)_7$ | H |
| 2 | $(CH_2)_3CH=CH_2$ | H | $(CH_2)_3O(CH_2)_4$ | H |
| 2 | $(CH_2)_3CH=CH_2$ | H | $(CH_2)_{11}O$ | H |
| 2 | $CH_2CH=CH_2$ | H | $OCH(CH_3)(CH_2)_3$ | $4-FC_6H_4$ |
| 2 | $CH_2CH=CH_2$ | H | $(CH_2)_6O$ | $C_6H_5$ |
| 2 | $(CH_2)_3CH=CH_2$ | H | $OCH(CH_3)(CH_2)_3$ | 2-pyridyl |
| 2 | $(CH_2)_3CH=CH_2$ | H | $(CH_2)_3OCH(CH_3)$ | $4-ClC_6H_4$ |
| 1 | $CH(OCH_3)_2$ | H | $[CH(CH_3)](CH_2)_5$ | H |
| 1 | $CH(OCH_3)_2$ | H | $(CH_2)_{11}$ | H |
| 1 | $CH(OCH_3)_2$ | H | $CH(CH_3)(CH_2)_3$ | $C_6H_5$ |

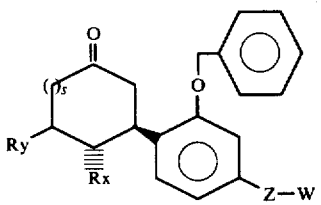

| s | Rx | Ry | Z | W |
|---|---|---|---|---|
| 1 | CH(OCH$_3$)$_2$ | H | CH(CH$_3$)(CH$_2$)$_3$ | 4-FC$_6$H$_4$ |
| 1 | CH(OCH$_3$)$_2$ | H | (CH$_2$)$_5$ | H |
| 2 | H | CH$_2$CH=CH$_2$ | (CH$_2$)$_3$O(CH$_2$)$_4$ | H |
| 2 | H | CH$_2$CH=CH$_2$ | O(CH$_2$)$_7$ | H |
| 2 | H | CH$_2$CH=CH$_2$ | OCH(CH$_3$)(CH$_2$)$_3$ | C$_6$H$_5$ |
| 2 | H | CH$_2$CH=CH$_2$ | O(CH$_2$)$_7$ | 4-ClC$_6$H$_4$ |
| 2 | H | CH$_2$CH=CH$_2$ | OCH(CH$_3$)(CH$_2$)$_3$ | 4-pyridyl |
| 2 | H | CH$_2$CH=CH$_2$ | CH(CH$_3$)(CH$_2$)$_3$ | C$_6$H$_5$ |
| 2 | H | CH$_2$CH=CH$_2$ | CH(C$_2$H$_5$)(CH$_2$)$_4$ | 4-FC$_6$H$_4$ |
| 2 | H | CH$_2$CH=CH$_2$ | OCH(CH$_3$)(CH$_2$)$_5$ | H |
| 1 | CH(OCH$_3$)$_2$ | H | CH(CH$_3$)(CH$_2$)$_3$ | 4-pyridyl |
| 1 | CH(OCH$_3$)$_2$ | H | OCH(CH$_3$)(CH$_2$)$_3$ | C$_6$H$_5$ |
| 1 | CH(OCH$_3$)$_2$ | H | OCH(CH$_3$)(CH$_2$)$_3$ | 4-pyridyl |
| 1 | CH(OCH$_3$)$_2$ | H | OCH(CH$_3$)(CH$_2$)$_5$ | H |
| 1 | CH(OCH$_3$)$_2$ | H | (CH$_2$)$_4$OCH$_2$ | C$_6$H$_5$ |
| 1 | CH(OCH$_3$)$_2$ | H | O(CH$_2$)$_{13}$ | H |
| 1 | CH(OCH$_3$)$_2$ | H | (CH$_2$)$_3$ | C$_6$H$_5$ |
| 1 | (CH$_2$)$_2$CH=CH$_2$ | CH$_3$ | C(CH$_3$)$_2$(CH$_2$)$_6$ | H |
| 1 | CH$_2$CH=CH$_2$ | CH$_3$ | OCH(CH$_3$)(CH$_2$)$_3$ | C$_6$H$_5$ |
| 1 | (CH$_2$)$_3$CH=CH$_2$ | CH$_3$ | O(CH$_2$)$_7$ | H |
| 1 | CH$_2$CH=CH$_2$ | CH$_3$ | CH(CH$_3$)(CH$_2$)$_3$ | C$_6$H$_5$ |
| 1 | CH$_2$CH=CH$_2$ | CH$_3$ | OCH(CH$_3$)(CH$_2$)$_3$ | 4-FC$_6$H$_4$ |
| 1 | CH$_2$CH=CH$_2$ | CH$_3$ | (CH$_2$)$_3$OCH(CH$_3$) | 4-ClC$_6$H$_4$ |
| 1 | CH$_2$CH=CH$_2$ | CH$_3$ | O(CH$_2$)$_{13}$ | H |
| 1 | (CH$_2$)$_2$CH=CH$_2$ | CH$_3$ | (CH$_2$)$_3$ | C$_6$H$_5$ |
| 1 | (CH$_2$)$_3$CH=CH$_2$ | CH$_3$ | (CH$_2$)$_8$ | C$_6$H$_5$ |
| 1 | (CH$_2$)$_4$CH=CH$_2$ | CH$_3$ | CH(CH$_3$)(CH$_2$)$_3$ | 2-pyridyl |
| 1 | CH$_2$CH=CH$_2$ | CH$_3$ | (CH$_2$)$_{11}$O | H |
| 1 | CH$_2$CH=CH$_2$ | CH$_3$ | (CH$_2$)$_3$O(CH$_2$)$_4$ | H |
| 2 | CH$_2$CH=CH$_2$ | CH$_3$ | OCH(CH$_3$)(CH$_2$)$_3$ | C$_6$H$_5$ |
| 2 | (CH$_2$)$_3$CH=CH$_2$ | CH$_3$ | C(CH$_3$)$_2$(CH$_2$)$_6$ | H |
| 2 | CH$_2$CH=CH$_2$ | CH$_3$ | CH(CH$_3$)(CH$_2$)$_3$ | 4-pyridyl |
| 2 | CH$_2$CH=CH$_2$ | CH$_3$ | O(CH$_2$)$_7$ | H |
| 2 | CH$_2$CH=CH$_2$ | CH$_3$ | CH(CH$_3$)(CH$_2$)$_3$ | 4-FC$_6$H$_4$ |

The products are converted to the corresponding ethylene ketals according to the procedure of Example 7.

EXAMPLE 61

The cycloalkanone compounds of Example 60 are reduced according to the procedure of Example 2 to provide the corresponding 3-[2-benzyloxy-4-(Z-W)phenyl]-4-(and 5)-substituted-cycloalkanols.

EXAMPLE 62

The cycloalkanols of Example 61 wherein Rx or Ry is alkenyl are hydrated according to the method of Example 5 to give the corresponding 3-[2-benzyloxy-4-(Z-W)phenyl]-4-(and 5)-ω-hydroxyalkylcycloalkanols.

Debenzylation of said compounds according to the catalytic hydrogenation procedure of Example 6 provides the corresponding phenols.

EXAMPLE 63

The cycloalkanone compounds of Example 60 wherein Rx or Ry is alkenyl are ketalized to their corresponding ethylene ketals by the procedure of Example 7 and then hydrated according to the procedure of Example 5 to produce the corresponding 3-[2-benzyloxy-4-(Z-W)phenyl]-4-(or 5)-(ω-hydroxyalkyl)cycloalkanone ethylene ketals. Catalytic hydrogenation according to the procedure of Example 6, followed by deketalization according to Example 8, affords the corresponding 3-[2-hydroxy-4-(Z-W)phenyl]-4-(or 5)-ω-(hydroxyalkyl)cycloalkanones.

EXAMPLE 64

Following the procedure of Example 9, the 3-[2-benzyloxy-4-(Z-W)phenyl]-4-(or 5)-alkenylcycloalkanones and cycloalkanols of Examples 60 and 61 are oxidized to give the corresponding compounds of the formula

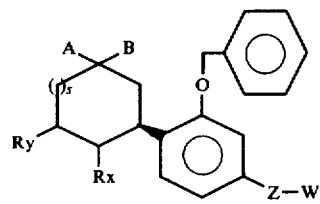

wherein A⌒B is —OCH$_2$CH$_2$O— or H, OH; s, Z and W are as defined in Examples 60 and 61; Rx or Ry represents the ω-oxoalkyl moiety having one less carbon in the alkyl group than does Rx or Ry of Examples 60 and 61.

Of course, in this example, the cycloalkanones are first ketalized according to the procedure of Example 7.

Also produced in this Example are corresponding compounds, wherein Rx or Ry is carboxyalkyl having two less carbon atoms in the alkyl group than does Rx or Ry; and the corresponding ω-hydroxyketones in which the unsaturated carbon atoms of the alkenyl moiety are converted to —CO—CH$_2$OH.

Debenzylation of the thus-produced oxygenated products by the procedure of Example 6 provides the corresponding phenols. Deketalization of the ketals according to the method of Example 8 gives the corresponding cycloalkanones.

EXAMPLE 65

The procedure of Example 12 is used to convert the 3-[2-benzyloxy-4-(Z-W)phenyl]-4-(or 5)-1-(oxoalkyl)-cycloalkanone ethylene ketals of Example 64 to the corresponding compounds wherein the 4-(or 5)-substituent is a secondary alcohol group. Deketalization of the products gives the cycloalkanones.

EXAMPLE 66

The ethylene ketal compounds of Example 60 wherein Rx or Ry is alkenyl and of Example 99 are converted to corresponding compounds wherein Rx or Ry is 4-(or 5)-ω-(1,3-dioxolan-2-yl)alk-2-enyl by the procedure of Example 10. Catalytic hydrogenation of said compounds according to the procedure of Example 11, followed by deketalization as per Example 8, affords 3-[2-benzyloxy-4-(Z-W)phenyl]-4-(or 5)-ω-(oxoalkyl)-cycloalkanones wherein the oxoalkyl group contains 3 more carbon atoms than did group Rx or Ry.

EXAMPLE 67

The 3-[2-hydroxy-4-(Z-W)phenyl]-4-(and 5)-ω-(oxoalkyl)cycloalkanone ethylene ketals and cycloalkanols of Example 64 and 66 are converted to corresponding 4-(and 5)-ω-(aminoalkyl) derivatives by the procedure of Example 16. The products are isolated as their hydrochloride salts.

EXAMPLE 68

The compounds of Examples 60 and 61 wherein R$_2$' is dimethoxymethyl [—CH(OCH$_3$)$_2$] are converted to the corresponding formyl (CHO) compounds by the procedure of Example 17.

EXAMPLE 69

The procedures of Examples 19 and 21 are used to produce the following compounds from appropriate 3-[2-benzyloxy-4-(Z-W)phenyl]-4-(and 5)-ω-(oxoalkyl)-cycloalkanols of Examples 17, 64, 68 and 104 and the appropriate dialkylphosphonoalkanoic acid esters.

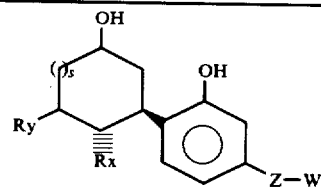

| s | Rx | Ry | Z | W |
|---|---|---|---|---|
| 1 | (CH$_2$)$_3$COOCH$_3$ | H | (CH$_2$)$_7$ | H |
| 1 | (CH$_2$)$_3$COOCH$_3$ | H | [CH(CH$_3$)]$_2$(CH$_2$)$_5$ | H |
| 2 | (CH$_2$)$_3$COOCH$_3$ | H | C(CH$_3$)$_2$(CH$_2$)$_6$ | H |
| 1 | (CH$_2$)$_3$COOC$_2$H$_5$ | H | C(CH$_3$)$_2$(CH$_2$)$_6$ | H |
| 2 | (CH$_2$)$_5$COOCH$_3$ | H | C(CH$_3$)$_2$(CH$_2$)$_6$ | H |
| 1 | (CH$_2$)$_3$COOC$_2$H$_5$ | H | [CH(CH$_3$)$_2$]$_2$(CH$_2$)$_5$ | H |
| 1 | (CH$_2$)$_2$COOCH$_3$ | H | (CH$_2$)$_5$ | H |
| 2 | (CH$_2$)$_2$COOC$_2$H$_5$ | H | (CH$_2$)$_5$ | H |
| 2 | H | (CH$_2$)$_2$COOCH$_3$ | (CH$_2$)O(CH$_2$)$_7$ | 4-ClC$_6$H$_4$ |
| 1 | (CH$_2$)$_3$COOCH$_3$ | H | (CH$_2$)$_{11}$ | H |
| 1 | (CH$_2$)$_5$COOCH$_3$ | H | C(CH$_3$)$_2$(CH$_2$)$_6$ | H |
| 2 | (CH$_2$)$_3$COOCH$_3$ | H | (CH$_2$)$_{11}$ | H |
| 1 | (CH$_2$)$_5$COOCH$_3$ | H | C(CH$_3$)$_2$(CH$_2$)$_6$ | H |
| 1 | (CH$_2$)$_5$COOCH$_3$ | H | (CH$_2$)$_{11}$ | H |
| 1 | (CH$_2$)$_2$COOCH$_3$ | H | CH(CH$_3$)(CH$_2$)$_3$ | C$_6$H$_5$ |
| 1 | (CH$_2$)$_2$COOCH$_3$ | H | (CH$_2$)$_{13}$ | H |
| 2 | (CH$_2$)$_2$COOCH$_3$ | H | (CH$_2$)$_3$ | C$_6$H$_5$ |
| 1 | (CH$_2$)$_2$COOCH$_3$ | H | O(CH$_2$)$_3$ | C$_6$H$_5$ |
| 1 | (CH$_2$)$_5$COOCH$_3$ | H | CH(CH$_3$)(CH$_2$)$_3$ | 4-FC$_6$H$_4$ |
| 1 | (CH$_2$)$_4$COOCH$_3$ | H | (CH$_2$)$_4$OCH$_2$ | C$_6$H$_5$ |
| 1 | (CH$_2$)$_4$COOCH$_3$ | H | C(CH$_3$)$_2$(CH$_2$)$_6$ | H |
| 1 | (CH$_2$)$_3$COOCH$_3$ | H | OCH(CH$_3$)(CH$_2$)$_5$ | H |
| 1 | (CH$_2$)$_4$COOC$_2$H$_5$ | H | OCH(CH$_3$)(CH$_2$)$_3$ | C$_6$H$_5$ |
| 1 | H | (CH$_2$)$_3$COOCH$_3$ | OCH(CH$_3$)(CH$_2$)$_3$ | C$_6$H$_5$ |
| 1 | H | (CH$_2$)$_3$COOCH$_3$ | OCH(CH$_3$)(CH$_2$)$_3$ | 4-ClC$_6$H$_4$ |
| 1 | H | (CH$_2$)$_2$COOCH$_3$ | OCH(CH$_3$)(CH$_2$)$_5$ | H |
| 1 | H | (CH$_2$)$_3$COOC$_2$H$_5$ | (CH$_2$)$_{11}$ | H |
| 1 | H | (CH$_2$)$_2$COOCH$_3$ | C(CH$_3$)$_2$(CH$_2$)$_6$ | H |
| 2 | H | (CH$_2$)$_3$COOCH$_3$ | C(CH$_3$)$_2$(CH$_2$)$_6$ | H |
| 2 | H | (CH$_2$)$_3$COOCH$_3$ | (CH$_2$)$_{11}$ | H |
| 2 | H | (CH$_2$)$_3$COOC$_2$H$_5$ | (CH$_2$)$_3$O(CH$_2$)$_4$ | H |
| 2 | H | (CH$_2$)$_3$COOCH$_3$ | OCH(CH$_3$)(CH$_2$)$_3$ | 4-pyridyl |
| 2 | H | (CH$_2$)$_3$COOCH$_3$ | CH(CH$_3$)(CH$_2$)$_3$ | C$_6$H$_5$ |
| 1 | (CH$_2$)$_2$COOC$_2$H$_5$ | H | OCH(CH$_3$)(CH$_2$)$_3$ | C$_6$H$_5$ |
| 1 | (CH$_2$)$_3$COOCH$_3$ | H | OCH(CH$_3$)(CH$_2$)$_3$ | 4-pyridyl |
| 1 | (CH$_2$)$_3$COOC$_2$H$_5$ | H | C(CH$_3$)$_2$(CH$_2$)$_6$ | H |
| 1 | (CH$_2$)$_5$COOCH$_3$ | H | OCH(CH$_3$)(CH$_2$)$_5$ | H |

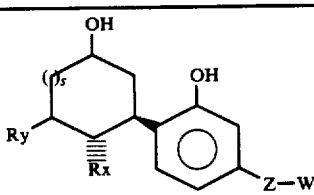

| s | Rx | Ry | Z | W |
|---|---|---|---|---|
| 1 | H | $(CH_2)_3COOCH_3$ | $OCH(CH_3)CH_3$ | $C_6H_5$ |
| 1 | H | $(CH_2)_2COOCH_3$ | $OCH(CH_3)(CH_2)_3$ | 4-pyridyl |
| 1 | H | $(CH_2)_3COOCH_3$ | $CH(CH_3)(CH_2)_3$ | $C_6H_5$ |
| 1 | H | $(CH_2)_3COOCH_3$ | $(CH_2)_3O(OCH_2)_4$ | H |
| 1 | H | $(CH_2)_3COOCH_3$ | $[CH(CH_3)]_2(CH_2)_5$ | H |
| 1 | H | $(CH_2)_3COOC_2H_5$ | $C(CH_3)_2(CH_2)_6$ | H |
| 2 | H | $(CH_2)_3COOC_2H_5$ | $[CH(CH_3)]_2(CH_2)_5$ | H |
| 2 | H | $(CH_2)_3COOCH_3$ | $O(CH_2)_{11}$ | H |
| 2 | H | $(CH_2)_3COOCH_3$ | $OCH(CH_3)(CH_2)_5$ | H |
| 2 | H | $(CH_2)_3COOC_2H_5$ | $OCH(CH_3)(CH_2)_3$ | $C_6H_5$ |
| 1 | $(CH_2)_2COOCH_3$ | H | $(CH_2)_3$ | $C_6H_5$ |
| 1 | $(CH_2)_2COOC_2H_5$ | $CH_3$ | $C(CH_3)_2(CH_2)_6$ | H |
| 1 | $(CH_2)_3COOCH_3$ | $CH_3$ | $OCH(CH_3)(CH_2)_3$ | $C_6H_5$ |
| 1 | $(CH_2)_5COOCH_3$ | $CH_3$ | $O(CH_2)_7$ | H |
| 1 | $(CH_2)_4COOCH_3$ | $CH_3$ | $CH(CH_3)(CH_2)_3$ | $C_6H_5$ |
| 1 | $(CH_2)_4COO(n-C_3H_7)$ | $CH_3$ | $OCH(CH_3)(CH_2)_3$ | $4-FC_6H_4$ |
| 1 | $(CH_2)_4COO(n-C_6H_{13})$ | $CH_3$ | $(CH_2)_3OCH(CH_3)$ | $4-ClC_6H_4$ |
| 1 | $(CH_2)_3COOCH_3$ | $CH_3$ | $O(CH_2)_{13}$ | H |
| 1 | $(CH_2)_6COOCH_3$ | $CH_3$ | $(CH_2)_3$ | $C_6H_5$ |
| 1 | $(CH_2)_6COO(n-C_6H_{13})$ | $CH_3$ | $(CH_2)_8$ | $C_6H_5$ |
| 1 | $(CH_2)_4COO(n-C_4H_9)$ | $CH_3$ | $C(CH_3)_2(CH_2)_6$ | H |
| 1 | $(CH_2)_6COOC_2H_5$ | $CH_3$ | $(CH_2)_3O(CH_2)_4$ | H |
| 2 | $(CH_2)_3COOC_2H_5$ | $CH_3$ | $OCH(CH_3)(CH_2)_3$ | $C_6H_5$ |
| 2 | $(CH_2)_5COOCH_3$ | $CH_3$ | $C(CH_3)_2(CH_2)_6$ | H |
| 2 | $(CH_2)_4COO(i-C_3H_7)$ | $CH_3$ | $CH(CH_3)(CH_2)_3$ | 4-pyridyl |
| 2 | $(CH_2)_4COOC_2H_5$ | $CH_3$ | $O(CH_2)_7$ | H |
| 2 | $(CH_2)COOCH_3$ | $CH_3$ | $CH(CH_3)(CH_2)_3$ | $4-FC_6H_4$ |

EXAMPLE 70

The 3-[2-benzyloxy-4-(Z-W)phenyl]-4-(and 5)-ω-(oxoalkyl)cycloalkanols of Examples 17, 64, 68 and 104 are converted to corresponding 3-[2-hydroxy-4-(Z-W)-phenyl]-4-(and 5)-ω-(carbamoylalkyl)cycloalkanols by the procedures of Examples 20 and 21 using, of course, the appropriate carbamoylalkylene triphenylphosphorane as the Wittig reagent.

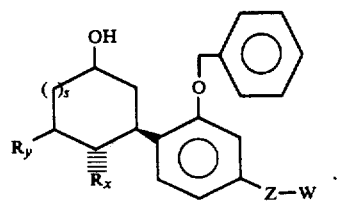

| s | Rx | Ry | Z | W |
|---|---|---|---|---|
| 1 | $(CH_2)_2CONH_2$ | H | $(CH_2)_7$ | H |
| 1 | $(CH_2)_2CONH(C_2H_5)$ | H | $C(CH_3)_2(CH_2)_6$ | H |
| 1 | $(CH_2)_3CONH_2$ | H | $[CH(CH_3)]_2(CH_2)_5$ | H |
| 1 | $(CH_2)_3CONH_2$ | H | $(CH_2)_{11}$ | H |
| 1 | $(CH_2)_5CON(CH_3)_2$ | H | $C(CH_3)_2(CH_2)_6$ | H |
| 1 | $(CH_2)_2CON(CH_3)_2$ | H | $C(CH_3)_2(CH_2)_6$ | H |
| 1 | $(CH_2)_3CONH_2$ | H | $C(CH_3)_2(CH_2)_6$ | H |
| 1 | $(CH_2)_2CONH_2$ | H | $(CH_2)_{11}$ | H |
| 1 | $(CH_2)_4CONH_2$ | H | $C(CH_3)_2(CH_2)_6$ | H |
| 1 | $(CH_2)_4CONH(C_2H_5)$ | H | $(CH_2)_8$ | H |
| 1 | $(CH_2)_6CONH_2$ | H | $[CH(CH_3)_2]_2(CH_2)_5$ | H |
| 1 | $(CH_2)_2CONH_2$ | H | $(CH_2)_4$ | $C_6H_5$ |
| 1 | $(CH_2)_2CONH(C_2H_5)$ | H | $(CH_2)_4$ | $C_6H_5$ |
| 1 | $(CH_2)_2CON(CH_3)_2$ | H | $CH(CH_3)(CH_2)_3$ | $C_6H_5$ |
| 1 | $(CH_2)_2CONH_2$ | H | $CH(CH_3)(CH_2)_3$ | $4-FC_6H_4$ |
| 1 | $(CH_2)_4CONH_2$ | H | $CH(CH_3)(CH_2)_4$ | 4-pyridyl |
| 2 | $(CH_2)_2CONH_2$ | H | $CH(CH_3)(CH_2)_3$ | $C_6H_5$ |
| 2 | $(CH_2)_3CONH_2$ | H | $CH(C_2H_5)(CH_2)_4$ | $4-FC_6H_4$ |
| 2 | $(CH_2)_6CONH_2$ | H | $C(CH_3)_2(CH_2)_6$ | H |
| 2 | $(CH_2)_4CON(CH_3)_2$ | H | $(CH_2)_7$ | H |
| 2 | $(CH_2)_3CON(CH_3)_2$ | H | $OCH(CH_3)(CH_2)_3$ | $C_6H_5$ |
| 2 | $(CH_2)_3CONH(C_2H_5)$ | H | $OCH(CH_3)(CH_2)_3$ | $4-FC_6H_4$ |

-continued

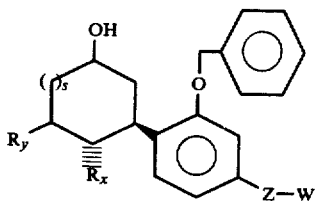

| s | Rx | Ry | Z | W |
|---|---|---|---|---|
| 2 | $(CH_2)_6CONH_2$ | H | $(CH_2)_3OCH(CH_3)$ | $4\text{-}ClC_6H_4$ |
| 2 | $(CH_2)_4CON(CH_3)_2$ | H | $O(CH_2)_7$ | H |
| 1 | $(CH_2)_3CONH_2$ | H | $O(CH_2)_4$ | $C_6H_5$ |
| 1 | $(CH_2)_6CONH_2$ | H | $OCH(CH_3)(CH_2)_3$ | 4-pyridyl |
| 1 | $(CH_2)_6CON(CH_3)_2$ | H | $[CH(CH_3)]_2(CH_2)_5$ | H |
| 1 | $(CH_2)_2CON(CH_3)_2$ | H | $(CH_2)_4$ | $C_6H_5$ |
| 1 | $(CH_2)_2CONH_2$ | H | $CH(CH_3)(CH_2)_3$ | $C_6H_5$ |
| 1 | $(CH_2)_6CONH_2$ | H | $CH(CH_3)(CH_2)_3$ | $C_6H_5$ |
| 1 | $(CH_2)_2CONH_2$ | H | $CH(CH_3)(CH_2)_3$ | 2-pyridyl |
| 1 | $(CH_2)_2CON(CH_3)_2$ | H | $[CH(CH_3)]_2CH_2$ | 4-pyridyl |
| 2 | $(CH_2)_5CON(CH_3)_2$ | H | $CH(CH_3)(CH_2)_3$ | $C_6H_5$ |
| 2 | $(CH_2)_3CONH_2$ | H | $C(CH_3)_2(CH_2)_6$ | H |
| 2 | $(CH_2)_3CONH(C_2H_5)$ | H | $C(CH_3)_2(CH_2)_6$ | H |
| 2 | $(CH_2)_3CONH_2$ | H | $OCH(CH_3)(CH_2)_3$ | $C_6H_5$ |
| 2 | $(CH_2)_4CONH_2$ | H | $OCH(CH_3)(CH_2)_3$ | $C_6H_5$ |
| 2 | $(CH_2)_4CONH_2$ | H | $(CH_2)_6O$ | $C_6H_5$ |
| 2 | $(CH_2)_3CONH_2$ | H | $OCH(CH_3)(CH_2)_5$ | H |
| 2 | $(CH_2)_6CONH_2$ | H | $(CH_2)_{11}O$ | H |
| 1 | $(CH_2)_3CONH(C_2H_5)$ | H | $OCH(CH_3)(CH_2)_3$ | $C_6H_5$ |
| 1 | $(CH_2)_4CONH_2$ | H | $(CH_2)_3OCH(CH_3)$ | 2-pyridyl |
| 1 | $(CH_2)_3CON(CH_3)_2$ | H | $O(CH_2)_5$ | 3-pyridyl |
| 1 | H | $(CH_2)_2CON(CH_3)_2$ | $C(CH_3)_2(CH_2)_6$ | H |
| 1 | H | $(CH_2)_3CONH(C_2H_5)$ | $C(CH_3)_2(CH_2)_6$ | H |
| 2 | H | $(CH_2)_3CONH_2$ | $(CH_2)_3O(CH_2)_4$ | H |
| 2 | H | $(CH_2)_3CONH_2$ | $C(CH_3)_2(CH_2)_6$ | H |
| 2 | H | $(CH_2)_3CON(CH_3)_2$ | $OCH(CH_3)(CH_2)$ | $C_6H_5$ |
| 1 | H | $(CH_2)_2CONH_2$ | $C(CH_3)_2(CH_2)_6$ | H |
| 2 | H | $(CH_2)_3CONH_2$ | $(CH_2)_5$ | H |
| 2 | H | $(CH_2)_3CONH_2$ | $(CH_2)_{11}$ | H |
| 2 | H | $(CH_2)_3CON(CH_3)_2$ | $OCH(CH_3)(CH_2)_5$ | H |
| 2 | H | $(CH_2)_3CONH_2$ | $CH(CH_3)(CH_2)_3$ | $C_6H_5$ |
| 2 | H | $(CH_2)_3CONH_2$ | $CH(C_2H_5)(CH_2)_4$ | $4\text{-}FC_6H_4$ |
| 1 | $(CH_2)_2CONH_2$ | $CH_3$ | $C(CH_3)_2(CH_2)_6$ | H |
| 1 | $(CH_2)_2CON(CH_3)_2$ | $CH_3$ | $C(CH_3)_2(CH_2)_6$ | H |
| 1 | $(CH_2)_3CONH_2$ | $CH_3$ | $OCH(CH_3)(CH_2)_3$ | $C_6H_5$ |
| 1 | $(CH_2)_2CONH(C_2H_5)$ | $CH_3$ | $OCH(CH_3)(CH_2)_3$ | $C_6H_5$ |
| 1 | $(CH_2)_2CON(CH_3)(n\text{-}C_4H_9)$ | $CH_3$ | $OCH(CH_3)(CH_2)_3$ | $C_6H_5$ |
| 1 | $(CH_2)_4CONH_2$ | $CH_3$ | $O(CH_2)_7$ | H |
| 1 | $(CH_2)_3CON(n\text{-}C_3H_7)_2$ | $CH_3$ | $O(CH_2)_{13}$ | H |
| 1 | $(CH_2)_2CONH(n\text{-}C_6H_{13})$ | $CH_3$ | $CH(CH_3)(CH_2)_3$ | $4\text{-}FC_6H_4$ |
| 1 | $(CH_2)_2CON(n\text{-}C_4H_9)_2$ | $CH_3$ | $CH(CH_3)(CH_2)_3$ | 4-pyridyl |
| 2 | $(CH_2)_2CONH_2$ | $CH_3$ | $OCH(CH_3)(CH_2)_3$ | $C_6H_5$ |
| 2 | $(CH_2)_3CON(CH_3)(n\text{-}C_4H_9)$ | $CH_3$ | $OCH(CH_3)(CH_2)_3$ | $C_6H_5$ |
| 2 | $(CH_2)_5CON(C_2H_5)_2$ | $CH_3$ | $C(CH_3)_2(CH_2)_6$ | H |
| 2 | $(CH_2)_2CON(CH_3)_2$ | $CH_3$ | $C(CH_3)(CH_2)_3$ | 4-pyridyl |
| 2 | $(CH_2)_4CONH(C_2H_5)$ | $CH_3$ | $O(CH_2)_7$ | H |
| 2 | $(CH_2)_3CONH(i\text{-}C_3H_7)$ | $CH_3$ | $CH(CH_3)(CH_2)_3$ | $4\text{-}FC_6H_4$ |
| 2 | $(CH_2)_3CONH(n\text{-}C_6H_{13})$ | $CH_3$ | $C(CH_3)_2(CH_2)_6$ | H |

Reduction of the above-listed amides according to the procedure of Example 23 affords the corresponding amines.

EXAMPLE 71

The 3-[2-hydroxy-4-(Z-W)phenyl]-4-(or 5)-substituted-cycloalkanones and the 3-[2-benzyloxy-4-(Z-W)-phenyl]-4-(or 5)-substituted-cycloalkanones wherein the substituent is other than ω-oxoalkyl of Examples 6, 8, 28, 53, 54, 60, 63 and 65 are converted to corresponding cycloalkanes by the procedure of Example 25. The compounds have the formula shown below wherein R° is hydrogen or benzyl; s, Z, W and the 4-(or 5) substituents are as defined in said examples.

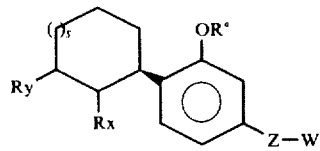

EXAMPLE 72

Following the procedures of Examples 26 and 5, the 3-[2-benzyloxy-4-(Z-W)phenyl]-4-(or 5)-alkenyl cycloalkanols of Examples 2, 13, 15, 29, 50 and 61 are converted to the corresponding benzyloxycycloalkanols according to the procedure of Example 26 and the ethers then hydrated by the procedure of Example 5 to give the corresponding 3-[2-benzyloxy-4-(Z-W)phenyl]-4-(or 5)-(ω-hydroxyalkyl)-1-benzyloxycycloalkanes.

EXAMPLE 73

The 3-[2-benzyloxy-4-(Z-W)phenyl]-4-(or 5)-(ω-hydroxyalkyl)-1-benzyloxycycloalkanes of Example 72 are converted to corresponding ω-($C_{1-6}$alkoxy)alkyl ethers by the procedures of Examples 26 or 27.

EXAMPLE 74

The 3-[2-benzyloxy-4-(Z-W)phenyl]-4-(or 5)-ω-(alkoxyalkyl)-1-benzyloxycycloalkanes of Examples 27 and 73 are debenzylated to the corresponding 3-[2-hydroxy-4-(Z-W)phenyl]-4-(or 5)-ω-(alkoxyalkyl)cycloalkanols by the procedure of Example 6.

EXAMPLE 75

Using the procedures of Examples 32 and 33, the cycloalkanol compounds of Examples 61, 67 and 70 are converted to corresponding 3-[2-benzyloxy-4-(Z-W)phenyl]-4-(or 5)-substituted-1-aminocycloalkanes.

Acetylation of the amino compounds thus produced provides the corresponding 1-acetamidocycloalkanes. Of course, when more than one amino group is present, as in the 3-[2-benzyloxy-4-(Z-W)phenyl]-4-(or 5)-ω-(amino alkyl)-1-aminocycloalkanes, 2 molar proportions of each of acetic anhydride and 4-N,N-dimethylaminopyridine are used.

The compounds are debenzylated to corresponding phenols by the procedure of Example 6.

EXAMPLE 76

Using the procedure of Example 5, the 3-[2-benzyloxy-4-(Z-W)phenyl]-4-(or 5)-alkenyl-1-acetamidocycloalkanes of Example 75 are hydrated to corresponding ω-hydroxyalkyl-1-acetamidocycloalkanes.

Debenzylation via the procedure of Example 6 affords the corresponding phenol derivatives.

EXAMPLE 77

Trans-3-(2,4-Dibenzyloxyphenyl)-4-(2-propenyl)cyclohexanone

Using the procedure of Example 1, 23 g. (62.3 mmole) of 2,4-dibenzyloxybromobenzene and 7.2 g. (53 mmole) of 4-(2-propenyl)-2-cyclohexanone gave 8.56 g. (38%) of the title compound.

m.p. 104°-106° C. (diisopropyl ether)

HRMS (m/e) 426.2203 (M+, calc'd. for $C_{29}H_{30}O_3$: 426.2187), 335, 181 and 91.

Analysis: Calc'd. for $C_{29}H_{30}O_3$: C, 81.66; H, 7.09. Found: C, 81.53; H, 6.85.

EXAMPLE 78

Trans-3-(2,4-Dibenzyloxyphenyl)-4-(2-propenyl)cyclohexane ethylene Ketal

A mixture of 5.0 g. (11.73 mmole) of trans-3-(2,4-dibenzyloxyphenyl)-4-(2-propenyl)cyclohexanone, 6.5 ml. (117 mmole) of ethylene glycol and 223 mg. (1.17 mmole) of p-toluenesulfonic acid in 50 ml. of benzene was heated at reflux for 1.5 hours. Water was removed via a soxhlet extractor filled with molecular sieves. The reaction was cooled and added to 500 ml. saturated sodium bicarbonate and 300 ml. ether. The ether phase was separated, dried over magnesium sulfate and evaporated. Trituration with diisopropyl ether-hexane gave 5.31 g. (96%) of the title compound.

m.p. 112°-113° C.

HRMS (m/e) 470.2520 (M+, calc'd. for $C_{31}H_{34}O_4$: 470.2448), 387, 379, 303, 181 and 91.

Analysis: Calc'd. for $C_{31}H_{34}O_4$: C, 79.12; H, 7.28. Found: C, 79.13; H, 7.02.

EXAMPLE 79

Trans-3-(2,4-Dibenzyloxyphenyl)-4-(3-hydroxypropyl)cyclohexanone ethylene Ketal

Using the procedure of Example 5, 5.00 g. (10.6 mmole) of trans-3-(2,4-dibenzyloxyphenyl)-4-(2-propenyl)cyclohexanone ethylene ketal afforded a quantitative yield of the title compound as an oil. The product was used in the procedure of Example 80 without purification.

EXAMPLE 80

Trans-3-(2,4-Dibenzyloxyphenyl)-4-(3-hydroxypropyl)cyclohexanone

A mixture of 5.17 g. (10.6 mmole) of trans-3-(2,4-dibenzyloxyphenyl)-4-(3-hydroxypropyl)cyclohexanone ethylene ketal, 50 ml. 1 N hydrochloric acid and 100 ml. tetrahydrofuran was heated at reflux for one hour. The reaction was cooled, partially evaporated on a rotovapor and the residue diluted with 300 ml. saturated sodium chloride-300 ml. ether. The ether extract was washed with 300 ml. saturated sodium bicarbonate, dried over magnesium sulfate and evaporated. The residue was crystallized from diisopropyl ether to yield 4.32 g. (92%) of the title compound.

m.p. 110°-117° C.

Analysis: Calc'd. for $C_{29}H_{32}O_4$: C, 78.35; H, 7.26. Found: C, 78.17; H, 7.15.

EXAMPLE 81

Trans-3-(2,4-Dihydroxyphenyl)-4-(3-hydroxypropyl)cyclohexanone

Following the procedure of Example 6, 3.9 g. (8.78 mmole) of trans-3-(2,4-dibenzyloxyphenyl)-4-(3-hydroxyphenyl)cyclohexanone provided 2.12 g. (91%) of the title compound as an oil.

HRMS (m/e) 264.1345 (M+, calc'd. for $C_{15}H_{20}O_4$: 264.1356), 178, 163, 161, 155, 136 and 123.

EXAMPLE 82

3,4-Dihydro-2-methoxy-7-hydroxy-2,4-propano-2H-1-benzopyran-9-propanol

A solution of 1.5 g. (5.68 mmole) of trans-3-(2,4-dihydroxyphenyl)-4-(3-hydroxypropyl)cyclohexanone in 40 ml. methanol, 6 ml. trimethylorthoformate and 7 drops of concentrated sulfuric acid was stirred at 0° C. for 45 minutes. The reaction was quenched by the addition of excess solid sodium bicarbonate and then evaporated on a rotovapor. The residue was diluted with 300 ml. saturated sodium bicarbonate-300 ml. ether. The ether extract was dried over magnesium sulfate and evaporated. The crude product was purified via column chromatography on 150 g. of silica gel eluted in 15 ml. fractions with ether to yield 1.29 g. (82%) of the title compound as an oil.

PMR (CDCl$_3$+D$_6$-DMSO) δ 1.88 (m), 2.85 (m), 3.35 (s, methoxy), 3.45 (m, methylene), 6.22 (d, J=2 Hz, ArH), 6.22 (dd, J=8 & 2 Hz, ArH) and 6.75 (d, J=8 Hz, ArH).

HRMS (m/e) 278.1514 (M+, calc'd. for C$_{16}$H$_{22}$O$_4$: 278.1512), 246, 192, 177 and 161.

EXAMPLE 83 d-3,4-dihydro-2-methoxy-7-[(2-octyl)oxy]-2,4-propano-2H-1-benzopyran-9-propanol

A mixture of 700 mg. (2.52 mmole) of 3,4-dihydro-2-methoxy-7-hydroxy-2,4-propano-2H-1-benzopyran-9-propanol 786 mg. (3.78 mmole) of l-2-octylmethanesulfonate and 1.38 g. (10 mmole) of anhydrous potassium carbonate in 5 ml. of dimethylformamide was heated at 80° C. for 8 hours and then stirred at room temperature for 10 hours. The reaction mixture was added to 300 ml. saturated sodium chloride-300 ml. ether. The ether extract was dried over magnesium sulfate and evaporated. The crude product was purified via column chromatography on 100 g. of silica gel eluted in 10 ml. fractions with ether to yield 711 mg. (72%) of the title compound as an oil.

PMR (CDCl$_3$) δ 0.88 (m, terminal methyl), 1.28 (d, J=6 Hz, methyl), 2.95 (m), 3.40 (s, methoxy), 3.70 (m, methylene), 4.22 (m, methine), 6.35 (m, ArH) and 6.82 (d, J=8 Hz, ArH).

HRMS (m/e) 390.2769 (M+, calc'd. for C$_{24}$H$_{38}$O$_4$: 390.2760), 304, 289, 273, 192, 191, 177 and 161.

$[\alpha]_D^{20°}$ = +3.17° (c=1.29 methanol)

EXAMPLE 84 d-Trans-3-[2-hydroxy-4-(2-octyloxy)phenyl]-4-(3-hydroxypropyl)cyclohexanone

A mixture of 711 mg. (1.82 mmole) of d-3,4-dihydro-2-methoxy-7-[(2-octyl)oxy]-2,4-propano-2H-1-benzopyran-9-propanol, 25 ml. tetrahydrofuran and 15 ml. 1 N hydrochloric acid was heated 1.5 hours at reflux. The reaction was cooled and diluted with 200 ml. saturated sodium chloride-200 ml. ether. The ether extract was washed with 200 ml. saturated sodium bicarbonate, dried over magnesium sulfate and evaporated to give a quantitative yeild of the title compound as an oil.

HRMS (m/e) 376.2592 (M+, calc'd. for C$_{23}$H$_{36}$O$_4$: 376.2604), 290, 275, 264, 179, 178, 177, 164, 163 and 161.

EXAMPLE 85 d-Cis-3-[2-hydroxy-4-(2-octyloxy)phenyl]-trans-4-(3-hydroxypropyl)cyclohexanol and the trans-3, cis-4 isomer Using the procedure of Example 2, 684 mg. (1.82 mmole) of d-trans-3-[2-hydroxy-4-(2-octyloxy)phenyl]-4-(3-hydroxypropyl)cyclohexanone yielded in order of elution with 50% ether-dichloromethane, 420 mg. (61%) of the title compound and 75 mg. (11%) of the trans-3, cis-4 isomer as oils.

Cis-3, trans-4

$[\alpha]_D^{20°}$ = +4.26° (c=1.01, methanol)

HRMS (m/e) 378.2762 (M+, calc'd. for C$_{23}$H$_{38}$O$_4$: 378.2760), 266, 248, 147 and 123.

Trans-3, cis-4

HRMS (m/e) 378.2789 (M+, calc'd. for C$_{23}$H$_{38}$O$_4$: 378.2760), 266, 248 and 123.

The compounds tabulated below are prepared according to the procedures of Examples 83 and 84 from the appropriate reactant CH$_3$—SO$_2$—O—Z—W.

| (alk$_2$) | W |
|---|---|
| (CH$_2$)$_4$ | C$_6$H$_5$ |
| CH(CH$_3$)(CH$_2$)$_3$ | C$_6$H$_5$ |
| CH(CH$_3$)(CH$_2$)$_5$ | C$_6$H$_5$ |
| CH(CH$_3$)(CH$_2$)$_3$ | 4-ClC$_6$H$_4$ |
| CH(CH$_3$)(CH$_2$)$_3$ | 4-FC$_6$H$_4$ |
| CH(CH$_3$)(CH$_2$)$_5$ | H |
| (CH$_2$)$_{11}$ | H |
| CH(CH$_3$)(CH$_2$)$_3$ | 4-pyridyl |
| (CH$_2$)$_4$ | 2-pyridyl |
| (CH$_2$)$_7$ | 2-pyridyl |
| (CH$_2$)$_{13}$ | H |
| (CH$_2$)$_3$ | C$_6$H$_5$ |

EXAMPLE 86

1-3,4-Dihydro-2-methoxy-7-[(2-octyl)oxy]-2,4-propano-2H-1-benzopyran-9-propanol

Using the procedure of Example 83, 700 mg. (2.52 mmole) of 3,4-dihydro-2-methoxy-7-hydroxy-2,4-propano-2H-1-benzopyran-9-propanol and 786 mg. (3.78 mmole) of d-2-octylmethanesulfonate gave 742 mg. (75%) of the title compound as an oil.

PMR (CDCl$_3$) δ 0.88 (m, methyl), 1.29 (d, J=6 Hz, methyl), 2.92 (m, methine), 3,38 (s, methoxy), 3.7 (m, methylene), 4.25 (m, methine), 6.3 (m, ArH) and 6.80 (d, J=8 Hz, ArH).

$[\alpha]_D^{20°}$ = −1.76 (c=1.33, methanol)

HRMS (m/e) 390.2763 (M+, calc'd. for C$_{24}$H$_{38}$O$_4$: 390.2769), 304, 289, 278, 273, 246, 192, 191, 177 and 175.

EXAMPLE 87

1-Trans-3-[2-hydroxy-4-(2-octyloxy)phenyl]-4-(3-hydroxypropyl)cyclohexanone

Using the procedure of Example 84, 742 mg. (1.90 mmole) of 1-3,4-dihydro-2-methoxy-7-[(2-octyl)oxy]-2,4-propano-2H-1-benzopyran-9-propanol gave a quantitative yield of title compound as an oil.

HRMS (m/e) 376.2624 (M+, calc'd. for C$_{23}$H$_{36}$O$_4$: 376.2592), 264, 179, 178 and 177.

EXAMPLE 88

1-Cis-3-[2-hydroxy-4-(2-octyloxy)phenyl]-trans-4-(3-hydroxypropyl)cyclohexanol and the trans-3,cis-4 isomer Using the procedure of Example 5, 714 mg. (1.90 mmole) of 1-trans-3-[2-hydroxy-4-(2-octyloxy)phenyl]-4-(3-hydroxypropyl)cyclohexanone afforded 483 mg. (67%) of the title compound and 101 mg. (14%) of the trans-3,cis-4 isomer as oils.

Cis-3, trans-4
$[\alpha]_D^{20°\,C.} = -5.21°$ (c=1.13, methanol)
HRMS (m/e) 378.2775 (M+, calc'd. for $C_{23}H_{38}O_4$: 378.2760), 266, 249, 248, 147 and 123.

Trans-3, cis-4
HRMS (m/e) 378.2767 (M+, calc'd. for $C_{23}H_{38}O_4$: 378.2760), 266, 248, 189, 149, 147 and 123.

EXAMPLE 89

Following the procedures of Examples 77–81, 4-(2-propenyl)-2-cycloheptenone is converted to trans-3-(2,4-dihydroxyphenyl)-4-(3-hydroxypropyl)cycloheptanone.

EXAMPLE 90

Repetition of the procedures of Examples 82–88, but using trans-3-(2,4-dihydroxyphenyl)-4-(3-hydroxypropyl)cycloheptanone as reactant in Example 82 procedure, and the appropriate $CH_3SO_2$—O—Z—W alkylating agent affords the following compounds:

| (alk$_2$) | W |
|---|---|
| CH(CH$_3$)(CH$_2$)$_6$ | H |
| CH(CH$_3$)(CH$_2$)$_5$ | H |
| (CH$_2$)$_{11}$ | H |
| CH(CH$_3$)(CH$_2$)$_3$ | C$_6$H$_5$ |
| (CH$_2$)$_4$ | C$_6$H$_5$ |
| CH(CH$_3$)(CH$_2$)$_3$ | 4-FC$_6$H$_4$ |
| (CH$_2$)$_4$ | 4-pyridyl |

EXAMPLE 91

Trans-4-(2-Propenyl)-3-[2-(tetrahydropyranyl-2-oxy)-4-(1,1-dimethyl-cis-2-heptenyl)phenyl]cyclohexanone To a 0° C. solution of 2.0 g. (6.62 mmole) of 1,1-dimethyl-1-[3-(tetrahydropyranyl-2-oxy)phenyl]-cis-2-heptane and 844 mg. (7.28 mmole) of tetramethylethylene heptane and 844 mg. (7.28 mmole) of tetramethylethylene diamine in 10 ml. of ether was slowly added 3.17 ml. (7.28 mmole) of m-butyllithium (in hexane). The resultant solution was stirred 5 minutes at 0° C. and then refluxed for 70 minutes. The resultant was then cooled to −78° C.

To a 0° C. solution of 597 mg. (7.28 mmole) of 1-hexyne in 10 ml. of tetrahydrofuran is slowly added 3.17 ml. (7.28 mmole) of m-butyllithium (in hexane). The resultant solution was stirred 10 minutes at 0° C. and then slowly added to a 0° C. slurry of 1.38 g. (7.28 mmole) of cuprous iodide in 10 ml. of tetrahydrofuran. The resultant yellow slurry was stirred 30 minutes at 0° C. and then slowly added to the above prepared −78° C. solution of aryl lithium reagent. The resultant yellow mixture was stirred 10 minutes at −78° C. and then 900 mg. (6.62 mmole) of 4-(2-propenyl)cyclohex-2-en-1-one is added dropwise. Stirring was continued for 10 minutes and then the reaction was placed in a −40° C. cooling bath and allowed to warm to −20° C. over 20 minutes. The reaction was quenched by addition to 200 ml. of cold saturated ammonium chloride brought to pH 10 with saturated ammonium hydroxide. The quenched reaction mixture was extracted with 300 ml. of ether. The ether extract was dried over magnesium sulfate and evaporated to an oil which was purified via column chromatography on 200 g. of silica gel eluted in 15 ml. fractions with 20% etherhexane to yield from fractions 40–63, 2.36 g. (82%) of the title compound as an oil.

IR (CHCl$_3$) 1709, 1641, 1610 and 1571 cm$^{-1}$.
HRMS (m/e) 354.2569 (P+.—C$_5$H$_8$O: Calcd. for $C_{24}H_{32}O_2$: 354.2550), 272, 271, 161, 137 and 85 (100%).
PMR (CDCl$_3$) δ 0.69 (m, terminal CH$_3$), 1.41 (s, gem dimethyl), 0.8–4.2 (series of m), 4.7–5.6 (m, olefinic H and THP methine), 5.62 (d, J=12 Hz, vinyl H) and 6.7–7.3 (m, ArH).

EXAMPLE 92

Trans-4-(2-Propenyl)-cis-3-[2-(tetrahydropyranyl-2-oxy)-4-(1,1-dimethyl-cis-2-heptenyl)phenyl]cyclohexanol and the cis-4,trans-3 isomer To a −78° C. solution of 20.0 g. (45.7 mmole) of trans-4-(2-propenyl)-3-[2-(tetrahydropyranyl-2-oxy)-4-(1,1-dimethyl-cis-2-heptenyl)phenyl]cyclohexanone in 200 ml. of methanol was added in one portion 5.20 g. (137 mmole) of sodium borohydride. The reaction was stirred overnight at −78° C. and then allowed to warm to 0° C. The reaction was quenched with 10 ml. saturated sodium chloride and then concentrated on a rotovapor. The residue was diluted with 500 ml. saturated sodium chloride and 500 ml. ether. The ether extract was washed once with 250 ml. saturated sodium bicarbonate, dried over magnesium sulfate and evaporated to an oil. The crude oil was purified via column chromatography on 1 kg. of silica gel eluted with 30% ether-hexane to yield in order of elution 2.20 g. (11%) of the cis-4,trans-3 isomer, 0.74 g. (4%) of mixture and 17.0 g. (85%) of the title compound as oils.

Title Compound:
IR (CHCl$_3$) 3593, 3464, 1640, 1610 and 1571 cm$^{-1}$.
HRMS (m/e) 356.2709 (P+.—C$_5$H$_8$O, Calcd. for $C_{24}H_{36}O_2$: 356.2706), 297, 273, 255, 124 and 85 (100%).
PMR (CDCl$_3$) δ 0.70 (m, terminal CH$_3$), 1.42 (s, gem dimethyl), 2.8 (bm, benzylic methine), 3.4–4.1 (m, carbinol methine and OCH$_2$), 4.6–5.5 (m, vinyl H and THP methine), 5.60 (d, J=11 Hz, vinyl H) and 6.8–7.2 (m, ArH).

EXAMPLE 93

Trans-4-(3-Hydroxypropyl)-cis-3-[2-(tetrahydropyranyl-2-oxy)-4-(1,1-dimethyl-cis-2-heptenyl)phenyl]cyclohexanol To a −5° C. solution of 13.3 g. (0.0302 mole) of trans-4-(2-propenyl)-cis-(3-[2-(tetrahydropyranyl-2-oxy)-4-(1,1-dimethyl-cis-2-heptenyl)phenyl]cyclohexanol in 100 ml. of tetrahydrofuran was slowly added 35.1 ml. (0.0351 mole) of boran-tetrahydrofuran (1 M in tetrahydrofuran), with stirring. After 30 minutes another 50 ml. of tetrahydrofuran was added and the reaction stirred 30 minutes longer, then quenched by addition of 40 ml. (0.12 mole) of 3 N sodium hydroxide and oxidized by addition of 10 ml. (0.112 mole) of 30% hydrogen peroxide. After stirring 20 minutes the reaction was added to 500 ml. saturated sodium chloride—500 ml. ether. The aqueous phase was extracted with another 250 ml. portion of ether and the combined ether extract dried over magnesium sulfate and evaporated to an oil. The crude oil was purified via column chromatography on 1 kg. of silica gel eluted with 80% etherhexane to 3% methanol-ether to yield in order of elution 600 mg. (5%) of unreacted starting material, 7.45 g. (54%) of the title compound as an oil, 1.32 g. (12%) of trans-4-(3-hydroxypropyl)-cis-3-[2-hydroxy-4-(1,1-dimethyl-cis-2-heptenyl)phenyl]cyclohexanol (phenolic product) and 1.78 g. (13%) of trans-4-(3-hydroxypropyl)-cis-3-[2-(tetrahydropyranyl-2-oxy)-4-(1,1-dimethyl-3-hydroxyheptyl)phenyl]cyclohexanol (Triol-THP).

Title Compound:

HRMS (m/e) 374.2831 (P+.—$C_5H_8O$, Calcd. for $C_{24}H_{38}O_3$: 374.2811), 356, 242, 151 and 85.

PMR (CDCl$_3$) δ 0.72 (m, terminal CH$_3$), 1.40 (s, gem dimethyl), 2.8 (m, benzylic methine), 3.47 (m, C$\underline{H}_2$OH), 3.2–4.2 (m, carbinol methine and —CH$_2$O—), 4.9–5.5 (vinyl H and THP methine), 5.62 (d, J=11 Hz, vinyl H) and 6.9–7.2 (m, ArH).

Phenotic Product:

HRMS (m/e) 374.2839 (M+., Calcd. for $C_{24}H_{38}O_3$: 374.2811), 356, 341, 299, 273 and 270.

Triol-THP:

HRMS (m/e) 392.2949 (P+.—$C_5H_8O$, Calcd. for $C_{24}H_{40}O_4$: 392.2916), 374, 292, 274, 165 and 85 (100%).

EXAMPLE 94

Trans-4-(3-d-Mandeloyloxy)-cis-3-[2-hydroxy-4-(1,1-dimethyl-cis-2-heptenyl)phenyl]-1-d-mandeloyloxycyclohexane A mixture of 6.00 g. (13.1 mmole) of trans-4-(3-hydroxypropyl)-cis-3-[2-(tetrahydropyranyl-2-oxy)-4-(1,1-dimethyl-cis-2-heptenyl)phenyl]cyclohexanol, 9.96 g. (65.6 mmole) d-mandelic acid and 498 mg. 2.62 mmole) p-toluenesulfonic acid monohydrate in 250 ml. of benzene was heated at reflux. Water was removed via a 3 A molecular sieve filled soxhlet extractor. The reaction was heated at reflux for 160 minutes with additional portions of p-toluenesulfonic acid monohydrate added at 40, 80 and 120 minutes. The reaction was cooled and added to 500 ml. saturated sodium bicarbonate—500 ml. ether. The aqueous phase was extracted with a second 250 ml. portion of ether and the combined ether extract dried over magnesium sulfate and evaporated to an oil. The crude product was purified via column chromatography on 800 g. of silica gel eluted with 55% ether-hexane to yield order of elution 2.25 g. (27%) of diastereomer A of the title compound, 2.0 g. (24%) of a mixture and 4.0 g. (48%) of slightly impure diastereomer B of the title compound as oils.

Diastereomer A:

20°[α]$_D^{CH3OH}$ = +31.62° (C=1.85)

PMR (CDCl$_3$) δ 0.68 (m, terminal CH$_3$), 1.37 (s, gem dimethyl), 3.4 (bd, J=6 Hz, OH), 3.93 (bt, J=6 Hz, —CH$_2$O—), 4.75 (m, OH), 5.02 (m, C$\underline{H}$OH), 5.0–5.7 (m, vinyl H), 6.6–6.9 (m, ArH), 7.23 and 7.26 (s, PhH).

EXAMPLE 95

(—)-Trans-4-(3-hydroxypropyl)-cis-3-[2-hydroxy-4-(1,1-dimethyl-cis-2-heptenyl)phenyl]cyclohexanol A mixture of 3.10 g. (4.92 mmole) of diastereomer A of trans-4-(3-d-mandeloyloxy)-cis-3-[2-hydroxy-4-(1,1-dimethyl-cis-2-heptenyl)phenyl]-1-d-mandeloyloxycyclohexane, 5.32 g. (38.6 mmole) potassium carbonate, 40 ml. methanol, 40 ml. tetrahydrofuran and 10 ml. water was stirred at 25° C. for 24 hours. The reaction was evaporated on a rotovapor and the residue dissolved in 250 ml. ether - 250 ml. saturated sodium chloride. The aqueous phase was extracted with two additional 150 ml. portions of ether, the combined ether extract dried over magnesium sulfate and evaporated to an oil. The crude product was purified via column chromatography on 150 g. of silica gel eluted with ether to yield 1.3 g. (72%) of the title compound.

MP: 95°–97° C. (Diisopropyl ether-hexane)

20°[60]$_D^{CH3OH}$ = —56.32°.

HRMS (m/e) 374.2819 (M+., Calcd. for $C_{24}H_{38}O_3$: 374.2811), 356, 213, 187, 161, 147, 124, 121, and 93.

PMR (250 mHz, CDCl$_3$) δ 0.73 (m, terminal methyl), 1.39 (s, gem dimethyl), 2.03 (m, CH$_2$-vinylic), 2.72 (m, benzylic methine), 3.47 (m, C$\underline{H}_2$OH), 3.74 (m, C$\underline{H}$OH), 5.07 (bs, OH), 5.22 and 5.27 (dt, J=11.51 and 7.31 Hz, vinyl H), 5.61 (dt, J=11.51 and 1.6 Hz, vinyl H), 6.73 (d, J=1.64 Hz, ArH), 6.91 (dd, J=8.22 and 1.82 Hz, ArH) and 7.02 (d, J=8.04 Hz, ArH).

EXAMPLE 96

(—)-Trans-4-(3-hydroxypropyl)-cis-3-[2-hydroxy-4-(1,1-dimethylheptyl)phenyl]cyclohexanol A mixture of 50.0 mg. (0.134 mmole) of (—)-trans-4-(3-hydroxypropyl)-cis-3-[2-hydroxy-4-(1,1-dimethyl-cis-2-heptenyl)phenyl]cyclohexanol and 50 mg. of 10% palladium on carbon in 5 ml. of dry tetrahydrofuran was stirred under one atmosphere of hydrogen for 30 minutes. The reaction was filtered through diatomaceous earth with tetrahydrofuran and the filtrate evaporated to yield 47.9 mg. (95%) of the title compound as an oil. 20°[α]$_D^{CH3OH}$ = —36.12°.

EXAMPLE 97

Trans-3,4-trans-4,5-3-[2-benzyloxy-4-(1,1-dimethylheptyl)phenyl]-5-methyl-4-(2-propenyl)cyclohexanone Using the procedure of Example 1, 7.5 g. (50 mmole) of trans-5-methyl-4-(2-propenyl)cyclohex-2-en-1-one and 24.3 g. (62.5 mmole) of 1-benzyloxy-2-bromo-5-(1,1-dimethylheptyl)benzene gave 13.0 g. (57%) of the title compound as an oil.

IR (CHCl$_3$) 1709, 1639, 1609 and 1568 cm$^{-1}$.

HRMS (m/e) 460.3353 (M+., Calcd. for $C_{32}H_{44}O_2$: 460.3330), 375, 370, 369 and 91 (100%).

PMR (CDCl$_3$) δ 0.82 (m, terminal CH$_3$), 1.26 (s, gem, dimethyl), 4.5–5.1 (m, vinyl H), 5.00 (s, benzylmethylene), 5.3–5.8 (vinyl H), 6.6–7.1 (m, ArH) and 7.25 (bs, PhH).

In like manner, trans-3,4-trans-4,5-3-[2-benzyloxy-4-(1,1-dimethylheptyl)phenyl]-5-methyl-4-(2-propenyl)-cycloheptanone is prepared from trans-5-methyl-4-(2-propenyl)cyclohept-2-en-1-one.

EXAMPLE 98

Cis-3-[2-benzyloxy-4-(1,1-dimethylheptyl)phenyl]-cis-5-methyl-trans-4-(2-propenyl)cyclohexanol Using the procedure of Example 2, 6.0 g. (13.0 mmole) of trans-3,4-trans, 4,5-3-[2-benzyloxy-4-(1,1-dimethylheptyl)phenyl]-5-methyl-4-(2-propenyl)cyclohexanone gave 1.1 g. (18%) of the cis-4,trans-3,trans-5 isomer of the title compound, 1.077 g. (17%) of a mixture and 2.79 (46%) of the title compound as an oil.

Cis-4,Trans-3,Trans-5 Isomer:

HRMS (m/e) 462.3501 (M+., Calcd. for $C_{32}H_{46}O_2$: 362.3486), 377, 269, 227 and 91 (100%).

PMR (CDCl$_3$) δ 0.82 (m, terminal methyl), 0.95 (d, J=6 Hz, methyl), 1.23 (s, gem dimethyl), 3.5 (m, benzylic methine), 4.13 (m, carbinol methine), 4.6–5.0 (m, vinyl H), 5.05 (s, benzylic methylene), 5.2–6.1 (m, vinyl H), 6.85 (m, ArH), 7.05 (d, J=8 Hz, ArH) and 7.38 (bs, PhH).

Title Compound:

IR (CHCl$_3$) 3596, 3463, 1639, 1609 and 1570 cm$^{-1}$.

HRMS (m/e) 462.3499 (M+., Calcd. for $C_{32}H_{46}O_2$: 462.3501), 377, 353, 269, 227 and 91 (100%).

PMR (CDCl$_3$) δ 0.83, (m, terminal CH$_3$), 1.25 (s, gem dimethyl), 3.2 (m, benzylic methine), 3.62 (bm, carbinol methine), 4.5–5.0 (m, vinyl H), 5.02 (s, benzylic methylene), 5.3–6.1 (m, vinyl H), 6.82 (m, ArH), 7.00 (d, J=8 Hz), ArH) and 7.35 (bs, PhH).

Following the above procedure trans-3,4-trans-4,5-3-[2-benzyloxy-4-(1,1-dimethylheptyl)phenyl]-5-methyl-trans-4-(2-propenyl)cycloheptanone is prepared from the correspondingly substituted cyclohept-2-en-1-one.

EXAMPLE 99

Trans-3,4-Trans-4,5-3-[2-benzyloxy-4-(1,1-dimethylheptyl)phenyl]-5-methyl-4-(2-propenyl)cyclohexanone ethylene ketal A mixture of 7.0 g. (15.2 mmole) of trans-3,4-trans,4,5-3-[2-benzyloxy-4-(1,1-dimethylheptyl)phenyl]-5-methyl-4-(2-propenyl)cyclohexanone, 8.47 ml. (152 mmole) of ethylene glycol and 89 mg. (1.52 mmole) of p-toluenesulfonic acid monohydrate was heated at reflux for 2.5 hours. Water was removed via a soxhlet extractor filled with 3 A sieves. The reaction was cooled and added to 250 ml. saturated sodium bicarbonate - 250 ml. ether. The ether extract was dried over magnesium sulfate and evaporated to an oil. The crude product was purified via column chromatography on 300 g. of silica gel eluted with 20% ether-hexane to yield 5.2 g. (68%) of the title compound as an oil.

IR (CHCl$_3$) 1638, 1608 and 1569 cm$^{-1}$.

HRMS (m/e) 504.3579 (M+., Calcd. for $C_{34}H_{48}O_3$: 504.3591), 419, 413, 407 and 91 (100%).

PMR (CDCl$_3$) δ 0.82 (m, terminal methyl), 0.99 (d, J=6 Hz, CH$_3$), 1.25 (s, gem dimethyl), 3.4 (m, benzylic methine), 3.90 (s, ethylene ketal), 4.4–5.0 (m, vinyl H), 5.03 (s, benzylic methylene), 5.3–6.2 (m, vinyl H), 6.80 (m, ArH), 7.00 (d, J=8 Hz, ArH) and 7.35 (bs, PhH).

The ethylene ketal of trans-3,4-trans-4,5-3-[2-benzyloxy-4-(1,1-dimethylheptyl)phenyl]-5-methyl-4-(2-propenyl)cycloheptanone is prepared in like manner from the corresponding cycloheptanone.

EXAMPLE 100

Cis-3-[4-(1,1-dimethylheptyl)-2-hydroxyphenyl]-cis-5-methylcyclohexanol

To a 0° C. solution of 900 mg. (1.95 mmole) of cis-3-[2-benzyloxy-4-(1,1-dimethylheptyl)phenyl]-cis-5-methyl-trans-4-(2-propenyl)cyclohexanol in 2 ml. of ether was added 5.1 ml. (11.7 mmole) of n-butyllithium (in hexane). The reaction was stirred 10 hours at 25° C. and then added to 200 ml. ether - 200 ml. saturated ammonium chloride. The ether extract was dried over magnesium sulfate and evaporated to an oil. This oil was crystallized in hexane to yield 495 mg. (68%) of the title compound.

MP 149°–150° C. (hexane)

IR (CHCl$_3$) 3455, 3253, 1643, 1617 and 1583 cm$^{-1}$.

HRMS (m/e) 372.3050 (M+., Calcd. for $C_{25}H_{40}O_2$: 372.3018), 312, 288, 287 (100%), 272, 269, 227, 187, 161, 147 and 135.

Analysis:

Analysis Calcd. For $C_{25}H_{40}O_2$: C, 80.59; H, 10.82. Found: C, 80.35; H, 10.81.

Debenzylation of cis-3-[2-benzyloxy-4-(1,1-dimethylheptyl)phenyl]-cis-5-methyl-trans-4-(2-propenyl)cycloheptanol is carried out in like manner.

EXAMPLE 101

Cis-3-[2-Benzyloxy-4-(1,1-dimethylheptyl)phenyl]-trans-4-(3-hydroxypropyl)-cis-5-methylcyclohexanol Using the procedure of Example 5, 900 mg. (1.95 mmole) of cis-3-[2-benzyloxy-4-(1,1-dimethylheptyl)-phenyl]-cis-5-methyl-trans-4-(2-propenyl)cyclohexanol was converted in quantitative yield to the title compound, an oil.

HRMS (m/e) 480.3574 (M.+, Calcd. for $C_{32}H_{48}O_3$: 480.3591), 462, 395, 377, 287 and 91 (100%).

By means of this procedure, cis-3-[2-benzyloxy-4-(1,1-dimethylheptyl)phenyl]-cis-5-methyl-trans-4-(2-propenyl)cycloheptanol is converted to the corresponding 3-hydroxypropyl derivative.

EXAMPLE 102

Cis-3-[4-(1,1-dimethylheptyl)-2-hydroxyphenyl]-trans-4-(3-hydroxypropyl)-cis-5-methylcyclohexanol Using the procedure of Example 6, 936 mg. (1.95 mmole) of cis-3-[2-benzyloxy-4-(1,1-dimethylheptyl)-phenyl]-trans-4-(3-hydroxypropyl)-cis-5-methylcyclohexanol afforded 602 mg. (79%) of the title compound.

MP 159°–160° C. (diisopropyl ether-ethyl acetate)

IR (KBr) 3533, 3367, 3211, 1617 and 1585 cm$^{-1}$.

HRMS (m/e) 390.3100 (M.+, Calcd. for $C_{25}H_{42}O_3$, 390.3123), 372, 304, 288, 287, 272, 257, 227, 219 and 187.

Analysis: Anal. Calcd. For $C_{25}H_{42}O_3$: C, 76.87; H, 10.84. Found: C, 76.60; H, 10.66.

Similarly, cis-3-[2-benzyloxy-4-(1,1-dimethylheptyl)-phenyl]-trans-4-(3-hydroxypropyl)-cis-5-methylcycloheptanol is debenzylated to the corresponding phenol.

EXAMPLE 103

Trans-3,4,Trans-4,5-3-[2-benzyloxy-4-(1,1-dimethylheptyl)phenyl]-4-(2-hydroxypropyl)-5-methylcyclohexanone ethylene ketal To a 25° C. mixture of 3.28 g. (10.3 mmole) of mercuric acetate in 50 ml. of 50% aqueous tetrahydrofuran was added 5.2 g. (10.3 mmole) of trans-3,4,trans-4,5-3-[-2-benzyloxy-4-(1,1-dimethylheptyl)phenyl]-5-methyl-4-(2-propenyl)cyclohexanone ethylene ketal in 25 ml. tetrahydrofuran. Another 25 ml. of water was added to aid solution and stirring. Additional 1.5 g. (4.7 mmole) portions of mercuric acetate were added after 2 hours and 24 hours. The reaction was stirred a total of 64 hours at 25° C. and then reduced by addition of 20 ml. 3 N sodium hydroxide and 20 ml. of 0.5 M sodium borohydride in 3 N sodium hydroxide. The reaction was stirred 30 minutes longer and then added to 250 ml. ether-300 ml. saturated sodium chloride. The ether extract was dried over magnesium sulfate and evaporated to an oil. The crude product was purified via column chromatography on 300 g. of silica gel eluted with 50% ether-hexane to give 1.5 g. (30%) of the title compound as an oil.

HRMS (m/e) 522.3712 (M.+, Calcd. for $C_{34}H_{50}O_4$: 522.3696), 431, 407, 372, 113 and 91 (100%).

PMR (CDCl$_3$) δ 0.75 (m, terminal methyl), 0.92 (d, J=6 Hz, C-5 methyl), 1.24 (s, gem dimethyl), 3.35 (bm, carbinol and benzylic methines), 3.90 (bs, ethylene ketal), 5.03 (s, benzylic methylene) and 6.6-7.5 (m, ArH).

Trans-3,4-trans-4,5-3-[2-benzyloxy-4-(1,1-dimethylheptyl)phenyl]-4-(2-hydroxypropyl)-5-methylcycloheptanone ethylene ketal is also prepared via this procedure from the corresponding 4-(2-propenyl)cycloheptanone ethylene ketal.

EXAMPLE 104

Trans-3,4,Trans-4,5-3-[2-Benzyloxy-4-(1,1-dimethylheptyl)phenyl]-5-methyl-4-(2-oxopropyl)cyclohexanone ethylene ketal To a 25° C. mixture of 1.5 g. (2.87 mmole) of trans-3,4,trans-4,5-3-[2-benzyloxy-4-(1,1-dimethylheptyl)phenyl]-4-(2-hydroxypropyl)-5-methylcyclohexanone ethylene ketal and 2.35 g. (28.7 mmole) of sodium acetate in 20 ml. of dichloromethane was added 1.93 g. (9 mmole) of pyridinium chlorochromate. The reaction mixture was stirred 3 hours at 25° C. and then added to 250 ml. 1 N NaOH-250 ml. ether. The organic extract was dried over magnesium sulfate and evaporated to give a quantitative yield of the title compound as an oil.

PMR (CDCl$_3$) δ 0.85 (m, methyls), 1.23 (s, gem dimethyl), 1.80 (bs, CH$_3$CO—), 2.23 (bs, —CH$_2$CO—), 3.3 (m, benzylic methine), 3.93 (s, ethylene ketal), 5.05 (s, benzylic methylene) and 6.7-7.6 (m, ArH).

In like manner, oxidation of trans-3,4-trans-4,5-3-[2-benzyloxy-4-(1,1-dimethylheptyl)phenyl]-4-(2-hydroxypropyl)cycloheptanone ethylene ketal affords the corresponding 4-(2-oxopropyl)cycloheptanone ethylene ketal.

EXAMPLE 105

Trans-3,4-Trans-4,5-3-[2-Benzyloxy-4-(1,1-dimethylheptyl)phenyl]-5-methyl-4-(2-methyl-2-propenyl)cyclohexanone ethylene ketal To a 15° C. mixture of 5.74 mmole of triphenyl phosphoniummethylide in 6 ml. of dimethyl sulfoxide was added a solution of 1.5 g. (2.87 mmole) of trans-3,4-trans-4,5-3-[2-benzyloxy-4-(1,1-dimethylheptyl)phenyl]-5-methyl-4-(2-oxopropyl)cyclohexanone ethylene ketal in 6 ml. of tetrahydrofuran and the reaction stirred 1.5 hours at 15°-25° C. It was then added to 200 ml. saturated sodium chloride-200 ml. ether. The ether extract was washed once with 200 ml. saturated sodium chloride, dried over magnesium sulfate and evaporated to give an oil. Purification via column chromatography on 50 g. of silica gel eluted with 20% ether-hexane gave 1.17 g. (79%) of the title compound as an oil.

HRMS (m/e) 518.3706 (M.+, Calcd. for $C_{35}H_{50}O_3$: 518.3747), 462, 427, 407, 372, 371, 285 and 91 (100%).

PMR (CDCl$_3$) δ 1.25 (s, gem dimethyl), 1.48 (bs, vinyl methyl), 3.3 (m, benzylic methine), 3.89 (s, ethylene ketal), 4.40 (m, vinyl H), 5.02 (s, benzylic methylene), 6.85 (m, ArH), 7.10 (d, J=8 Hz, ArH) and 7.4 (m, PhH).

Trans-3,4-trans-4,5-3-[2-benzyloxy-4-(1,1-dimethylheptyl)phenyl]-5-methyl-4-(2-oxopropyl)cycloheptanone ethylene ketal is converted in like manner to the corresponding 4-(2-methyl-2-propenyl)cycloheptanone ethylene ketal.

EXAMPLE 106

Trans-3,4-trans-4,5-3-[2-Benzyloxy-4-(1,1-dimethylheptyl)phenyl]-5-methyl-4-(2-methyl-2-propenyl)cyclohexanone A mixture of 1.1 g. (2.12 mmole) of the ethylene ketal of the title compound, 20 ml. tetrahydrofuran and 20 ml. 1 N hydrochloric acid was heated at reflux for 5 hours and stirred at 25° C. for 16 hours. The reaction was added to 250 ml. saturated sodium chloride-250 ml. ether. The ether extract was washed with 250 ml. saturated sodium bicarbonate, dried over magnesium sulfate and evaporated to give a quantitative yield of the title compound as an oil.

HRMS (m/e) 474.3524 (M.+, Calcd. for $C_{33}H_{46}O_2$): 474.3486), 418, 383, 327, 273 and 91 (100%).

Deketalization of trans-3,4-trans-4,5-3-[2-benzyloxy-4-(1,1-dimethylheptyl)phenyl]-5-methyl-4-(2-methyl-2-propenyl)cycloheptanone ethylene ketal is accomplished in like manner.

EXAMPLE 107

Cis-3-[2-Benzyloxy-4-(1,1-dimethylheptyl)phenyl]-cis-5-methyl-trans-4-(2-methyl-2-propenyl)cyclohexanol and its axial Isomer Using the procedure of Example 13, 1.00 g. (2.12 mmole) of trans-3,4-trans-4,5-3-[2-benzyloxy-4-(1,1-dimethylheptyl)phenyl]-cis-5-methyl-trans-4-(2-methyl-2-propenyl)cyclohexanone gave 248 mg. (25%) of the trans-3,cis-4,trans-5 isomer of the title compound and 720 g. (71%) of the title compound as oils.

Trans-3,cis-4,trans-5 Isomer:

HRMS (m/e) 476.3664 (M.+, Calcd. for $C_{33}H_{48}O_2$: 476.3642), 420, 335, 330, 329 (100%), 312, 311, and 283.

Title Compound:

HRMS (m/e) 476.3646 (M.+, Calcd. for $C_{33}H_{48}O_2$: 476.3642), 420, 330, 329 and 91 (100%).

Similarly trans-3,4-trans-4,5-3-[2-benzyloxy-4-(1,1-dimethylheptyl)phenyl]-cis-5-methyl-trans-4-(2-methyl-2-propenyl)cycloheptanone is transformed to cis-3-[2-benzyloxy-4-(1,1-dimethylheptyl)phenyl]-cis-5-methyl-trans-4-(2-methyl-2-propenyl)cycloheptanol and the corresponding axial derivative.

EXAMPLE 108

Cis-3-[2-Benzyloxy-4-(1,1-dimethylheptyl)phenyl]-trans-4-(3-hydroxy-2-methylpropyl)-cis-5-methylcyclohexanol Using the procedure of Example 5, 710 mg. (1.49 mmole) of cis-3-[2-benzyloxy-4-(1,1-dimethylheptyl)phenyl]-cis-5-methyl-trans-4-(2-methyl-2-propenyl)cyclohexanol (compound of Example 107) gave 322 mg. (44%) of diastereomer A and 356 mg. (48%) of diastereomer B of title compound as oils.

Diastereomer A:

HRMS (m/e) 494.3769 (M.+, Calcd. for $C_{33}H_{50}O_3$: 494.3747), 386, 301 and 91 (100%).

Diastereomer B:

HRMS (m/e) 494.3790 (M.+, Calcd. for $C_{33}H_{50}O_3$: 494.3747) and 91 (100%).

In like manner, the remaining alkenyl derivatives of Example 107 are hydrated to the corresponding alcohols.

EXAMPLE 109

Cis-3-[4-(1,1-dimethylheptyl)-2-hydroxyphenyl]-trans-4-(3-hydroxy-2-methylpropyl)-cis-5-methylcyclohexanol Diastereomer A Using the procedure of Example 6, 320 mg. (0.648 mmole) of diastereomer A of cis-3-[2-benzyloxy-4-(1,1-dimethylheptyl)phenyl]-trans-4-(3-hydroxy-2-methylpropyl)-cis-5-methylcyclohexanol (product of Example 108) provided 221 mg. (84%) of the title compound.

MP 139°–141° C. (diisopropyl ether-hexane)

IR (CHCl₃) 3588, 3407, 1616 and 1579 cm$^{-1}$.

HRMS (m/e) 404.3247 (M.+, Calcd. for $C_{26}H_{44}O_3$: 404.3279), 386, 301, 233, 187, 161 and 147 (100%).

Analysis: Anal. Calcd. for $C_{26}H_{44}O_3$: C, 77.17; H, 10.96. Found: C, 77.41; H, 10.77.

Diastereomer B

Using the procedure of Example 6, 350 mg. (0.709 mmole) of diastereomer B of cis-3-[2-benzyloxy-4-(1,1-dimethylheptyl)phenyl]-trans-4-(3-hydroxy-2-methylpropyl)-cis-5-methylcyclohexanol (product of Example 108) gave 255 mg. (89%) of the title compound.

MP 118°–120° C. (diisopropyl ether-hexane).

HRMS (m/e) 404.3237 (M.+, Calcd. for $C_{26}H_{44}O_3$: 404.3279), 386, 318, 301 (100%), 233, 187, 167 and 147.

Analysis: Anal. Calcd. for $C_{26}H_{44}O_3$: C, 77.17; H, 10.96. Found: C, 77.40; H, 10.76.

By means of this procedure, the remaining benzyl ethers of Example 108 are converted to the corresponding phenols.

EXAMPLE 110

7-Oxabicyclo[4.1.0]-1-[2-benzyloxy-4-(1,1-dimethylheptyl)phenyl]-3-heptanone ethylene ketal To a 0° C. solution of 5.0 g. (11.2 mmole) of 3-[2-benzyloxy-4-(1,1-dimethylheptyl)phenyl]cyclohex-3-en-1-one ethylene ketal in 15 ml. of dichloromethane is added 1.26 g. (15 mmole) of sodium bicarbonate and 2.58 g. (15 mmole) of m-chloroperbenzoic acid. The reaction is stirred overnight at 0° C. and then filtered. The filtrate is diluted with 200 ml. of ether and washed with two 100 ml. portions of saturated sodium bicarbonate. The organic extract is dried over magnesium sulfate and evaporated to yield the title compound.

EXAMPLE 111

3-[2-Hydroxy-4-(1,1-dimethylheptyl)phenyl]-4-hydroxycyclohexanone ethylene ketal Following the procedure of Example 6, 7-oxabicyclo[4.1.0]-1-[2-benzyloxy-4-(1,1-dimethylheptyl)-phenyl]-3-heptanone ethylene ketal is hydrogenated to give the title compound.

Deketalization according to the procedure of Example 8 affords the corresponding ketone.

Following the procedures of Example 110, 3-[2-benzyloxy-4-(1,1-dimethylheptyl)phenyl]cyclohept-3-en-1-one is converted to 3-[2-hydroxy-4-(1,1-dimethylheptyl)-phenyl]-4-hydroxycycloheptanone.

EXAMPLE 112

Cis-3-[2-Hydroxy-4-(1,1-dimethylheptyl)phenyl]-trans-4-hydroxycyclohexanol

Sodium borohydride reduction of 3-[2-hydroxy-4-(1,1-dimethylheptyl)phenyl]-4-hydroxycyclohexanone according to the procedure of Example 2 affords the title compound.

Similarly, reduction of 3-[2-hydroxy-4-(1,1-dimethylheptyl)phenyl]-4-hydroxycycloheptanone affords the corresponding alcohol.

PREPARATION A 6-(3-Butenyl)-3-ethoxy-2-cyclohexen-1-one

A solution of 25 g. (0.178 mole) of 3-ethoxy-2-cyclohexen-1-one in 25 ml. of tetrahydrofuran was added dropwise over a 30 minute period to a −78° C. solution of 0.196 mole of lithium diisopropylamide (from 27.4 ml., 0.196 mole, of diisopropylamine and 85 ml., 0.187 moles of 2.2 M n-butyllithium in hexane) in 125 ml. of tetrahydrofuran. The reaction was then stirred for 30 minutes and 65 ml. (0.374 mole) of hexamethylphosphoramide added followed by 38.9 ml. (0.383 mole) of 4-bromo-1-butene. The reaction was then allowed to warm to room temperature, stirred for 1.5 hours and then quenched by addition of 5 ml. (0.277 mole) of water. Most of the solvent was removed on a rotovapor and the residue diluted with 1000 ml. ice water and 500 ml. ether. The ether phase was separated, washed with two 300 ml. portions of water, dried over magnesium sulfate and evaporated on a rotovapor. Distillation of the resulting crude oil gave 10.1 g. (29%) of the title product.

b.p.: 83° C. (0.02 torr)

PMR $\delta_{CDCl_3}^{TMS}$ 1.34 (t, J=7 Hz, methyl), 1.3–2.6 (m), 3.86 q, J=7 Hz, methylene), 4.75–5.2 and 5.45–6.2 (m, terminal olefin) and 5.26 (s, vinyl H).

In like manner, 6-(3-benzyloxypropyl)-3-ethoxy-2-cyclohexen-1-one was prepared from 12.9 g. (91.9 mmole) of 3-ethoxy-2-cyclohexen-1-one and 28.0 g. (101 mmole) of 1-benzyloxy-3-iodopropane. Yield: 17.0 g. (67%). Purification was achieved via column chromatography on 500 g. of 5% sodium bicarbonate silica gel eluted with 75% ether-hexane.

IR (CHCl₃) 1632 and 1600 cm$^{-1}$.

MS (m/e) 288 (M+)

PMR $\delta_{CDCl_3}^{TMS}$ 1.34 (t, J=7 Hz, methyl), 1.4–2.6 (m), 3.50 (bt, J=6 Hz, methylene), 3.85 (q, J=7 Hz, methylene), 4.49 (s, benzylic methylene), 5.27 (s, vinyl H) and 7.27 (s, PhH).

PREPARATION B 4-(3-Butenyl)-2-cyclohexen-1-one

To a 0° C. slurry of 1.06 g. (26 mmoles) of lithium aluminum hydride in 75 ml. of ether was added a solution of 10 g. (51 mmoles) of 6-(3-butenyl)-3-ethoxy-2cyclohexen-1-one in 25 ml. of ether. After stirring for one hour, the reaction was quenched by addition of 100 ml. of 2 N hydrochloric acid. The quenched mixture was stirred for 30 minutes and then extracted with 300 ml. of ether. The ether extract was washed with 250 ml. saturated sodium bicarbonate, dried over magnesium sulfate and evaporated on a rotovapor. Distillation of the crude oil gave 5.98 g. (78%) of the title product.

b.p.: 133°–136° C. (22 torr)

PMR $\delta_{CDCl_3}^{TMS}$ 1.3–2.7 (m), 4.9–5.4 (m, terminal olefin), 5.5–6.2 (m, terminal olefin), 6.02 (bd, J=10 Hz, C-2 vinyl H) and 6.91 (bd, J=10 Hz, C-3 vinyl H).

Similarly, 4-(3-benzyloxypropyl)-2-cyclohexen-1-one was prepared in 74% (11.1 g.) yield from 17.0 g. (61.6 mmole) of 6-(3-benzyloxypropyl)-3-ethoxy-2-cyclohexen-1-one. The product was an oil.

IR (CHCl₃) 1680 and 1459 cm⁻¹.

PMR $\delta_{CDCl_3}^{TMS}$ 1.2–2.8 (m), 3.55 (bt, J=6 Hz, methylene), 4.50 (s, benzylic methylene), 5.92 (dd, J=10 and 2 Hz, vinyl H), 6.82 (bd, J=10 Hz, vinyl H) and 7.33 (s, PhH).

PREPARATION C 2-(1,3-Dioxolan-2-yl)ethyltriphenylphosphonium bromide

A solution of 25 g. (0.138 mmole) of 2-(2-bromoethyl)-1,3-dioxolane and 36.2 g. (0.138 mmole) of triphenylphosphine in 30 ml. of toluene was heated at 100° C. for 18 hours. The reaction was cooled to yield two phases. The toluene phase was decanted and the oil remaining crystallized at −78° C. in ethyl acetate. Decantation of the ethyl acetate and warming of the crystals to room temperature gave an oil. The oil was dried under vacuum (0.05 torr) at 100° C. for 16 hours to yield 15 g. (27%) of the title compound as a solid glass which was ground to a powder.

PREPARATION D

8-Oxabicyclo[5.1.0]octan-2-one

To a 0° C. solution of 50.0 g. (0.454 mmole) of cyclohept-2-en-1-one in 800 ml. of methanol was added 85 ml. of 30% hydrogen peroxide (0.75 mole) followed by the dropwise addition of 15 ml. of 6 N sodium hydroxide (0.09 mole). The reaction was stirred for one hour and then added to 400 ml. ether-500 ml. petroleum ether. The ether extract was removed and the aqueous methanol phase extracted with four 500 ml. portions of petroleum ether and three 300 ml. portions of dichloromethane. The combined organic extracts were washed with three 800 ml. portions of saturated sodium chloride, dried over magnesium sulfate and evaporated under reduced pressure to an oil (53 g.). The crude oil was purified via vacuum distillation to yield 45.9 g. (80%) of the title compound as an oil. Caution: several forceful detonations have occurred during distillation of the crude product. (In general, however, the crude product is pure enough for further synthetic manipulations and distillation can be avoided).

b.p.: 89°–90° C. (14 torr)

IR (CHCl₃) 1695 and 1600 cm⁻¹.

MS (m/e) 126 (M+), 99, 98, 97 and 84.

PMR $\delta_{CDCl_3}^{TMS}$ 0.7–1.5 (m), 1.5–3.0 (m) and 3.48 (d, J=3 Hz, C-1H).

PREPARATION E

3-Hydroxycycloheptanone

To a 25° C. solution of 45.9 g. (0.364 mole) of 8-oxabicyclo[5.1.0]octan-2-one in 950 ml. of 10% aqueous tetrahydrofuran was added 39.7 g. (1.47 mmoles) of aluminum amalgam. (The aluminum amalgam was prepared by 15–30 second successive washing of small pieces of aluminum foil with 2 N sodium hydroxide, distilled water, 0.5% mercuric chloride, distilled water, 2 N sodium hydroxide, distilled water, 0.5% mercuric chloride, distilled water, ethanol and ether). The mixture was stirred for 2 hours, then filtered through diatomaceous earth. The filtrate was evaporated on a rotovapor, the residue saturated with solid sodium chloride and extracted with three 500 ml. portions of ether. The ether extract was dried over magnesium sulfate and evaporated to yield 45 g. (97%) of the title compound as an oil.

IR (CHCl₃) 3390, 1695 and 1610 cm⁻¹.

MS (m/e) 128 (M+), 110, 100 and 85.

PMR $\delta_{CDCl_3}^{TMS}$ 1.80 (m), 2.42 (m, C-7 methylene), 2.89 (d, J=6 Hz, C-2 methylene), 3.40 (bs, OH) and 4.02 (m, C-3 methine).

PREPARATION F

Cycloheptan-1,3-dione

To a 10°–20° C. solution of 20 g. (0.156 mole) of 3-hydroxycycloheptanone in 700 ml. of acetone was slowly added 54.9 ml. of 2.67 M Jone's reagent (0.146 mole). The mixture was stirred 15 minutes and then quenched by addition of 12 ml. of isopropanol. The reaction was filtered through diatomaceous earth and the filtrate concentrated on a rotovapor to about 100 ml. The residue was diluted with 300 ml. of saturated sodium chloride and then extracted with six 250 ml. portions of ether. The combined organic extract was washed with two 100 ml. portions of saturated sodium bicarbonate, dried over magnesium sulfate and evaporated under reduced pressure (aspirator) to yield an oil. Distillation of the crude oil gave 11.5 g. (58%) of the title compound as an oil.

b.p.: 117°–121° C. (14 torr)

IR (CHCl₃) 3509 (weak), 1733, 1704 and 1621 cm⁻¹.

MS (m/e) 126 (M+), 98, 83 and 70.

PMR $\delta_{CDCl_3}^{TMS}$ 2.0 (m, C-5,6 methylenes), 2.58 (m, C-4,7 methylene) and 3.60 (s, C-2 methylene).

PREPARATION G

3-Ethoxycyclohept-2-en-1-one

A solution of 22.3 g. (0.177 mole) of cycloheptan-1,3-dione and 600 mg. (3.16 mmoles) of p-toluenesulfonic acid monohydrate in 86 ml. of ethanol and 250 ml. of toluene was heated at reflux for 18 hours. A soxhlet extractor filled with molecular sieves (3 Å) was used to remove water from the reaction. The reaction was cooled, added to 800 ml. saturated sodium chloride and extracted with four 800 ml. portions of ether. The combined organic extract was dried over magnesium sulfate and evaporated to an oil. Distillation of the crude oil gave 25.3 g. (93%) of the title compound as an oil.

b.p.: 74°–78° C. (0.10–0.15 torr)

IR (Neat) 1645 and 1613 cm⁻¹.

MS (m/e) 154 (M+), 135, 109, 98 and 97.

PMR $\delta_{CDCl_3}^{TMS}$ 1.34 (t, J=7 Hz, methyl), 1.8 (m, C-5,6 methylenes), 2.6 (m, C-4,7 methylene), 3.80 (q, J=7 Hz, ether methylene) and 5.37 (s, olefinic H).

PREPARATION H

3-Ethoxy-7-(2-propenyl)cyclohept-2-en-1-one

Following Preparation A, 15 g. (97.4 mmole) of 3-ethoxycyclohept-2-en-1-one and 23.5 g. (0.195 mole) of allyl bromide gave 11.4 g. (60%) of the title compound as an oil.

b.p.: 80°-87° C. (0.05-0.1 torr)
IR (Neat) 1650 and 1608 cm$^{-1}$.
MS (m/e) 194 (M+)
PMR $\delta_{CDCl_3}{}^{TMS}$ 1.38 (t, J=7 Hz, methyl), 1.4-3.1 (m), 3.87 (q, J=7 Hz, ether methylene), 4.9-5.3 and 5.4-6.3 (m, olefinic) and 5.42 (s, C-2 vinyl H).

PREPARATION I

4-(2-Propenyl)cyclohept-2-en-1-one

Following Preparation B, 12.0 g. (61.8 mmole) of 3-ethoxy-7-(2-propenyl)cyclohept-2-en-1-one gave 3.0 g. (33%) of the title compound as an oil.
b.p.: 71°-72° C. (0.1 torr)
IR (Neat) 1678 (broad) cm$^{-1}$).
MS (m/e) 150 (M+)
PMR $\delta_{CDCl_3}{}^{TMS}$ 1.2-3.0 (m), 4.8-6.1 (m, terminal olefin), 5.96 (dd, J=12 and 2 Hz, C-2H) and 6.42 (dd, J=12 and 3 Hz, C-3H).

PREPARATION J

(R)-1-Bromo-2-benzyloxy-4-(1-methyl-4-phenylbutoxy)benzene

A mixture of 21.8 g. (78 mmole) of 3-benzyloxy-4-bromophenol, 20.0 g. (82.6 mmole) of (S)-1-methyl-4-phenylbutyl methane sulfonate and 25.2 g. (200 mmole) of potassijm carbonate in 100 ml. dimethylformamide was heated at 85° C. for 13.5 hours. The reaction was cooled and added to 500 ml. water-500 ml. ether. The organic extract was washed with two 250 ml. portions of water, dried over magnesium sulfate and evaporated to an oil. The crude oil was purified via column chromatography on 750 g. of silica gel eluted with 10% ether-hexane to yield 23.9 g. (72%) of the title compound as an oil.
$[\alpha]_D{}^{25°} = -11.39°$ (C=1.137, CH$_3$Cl)
IR (CHCl$_3$) 1574 cm$^{-1}$.
HRMS (m/e) 426.1011 (M+, calc'd. for C$_{24}$H$_{25}$O$_2$Br: 426.1012), 424, 280, 278, 104 and 91.
PMR (CDCl$_3$) $\delta$ 1.22 (d, J=6 Hz, methyl), 1.4-2.0 (m), 2.60 (m, benzylic methylene), 4.24 (m, methine), 5.07 (s, benzylic methylene), 6.30 (d, J=2 Hz and 8 Hz, ArH), 6.46 (d, J=2 Hz, ArH), 7.17 (s, PhH) and 7.35 (m, PhH).

PREPARATION K

1-Benzyloxy-3-iodopropane

To a solution of 83.3 g. (0.318 mole) triphenylphosphine in 200 ml. benzene was added, in four portions, 80 g. (0.318 mole) of iodine. The resultant mixture was stirred 3 hours and then 50 ml. (0.618 mole) of pyridine was added followed by the slow addition of 32 g. (0.192 mole) of 3-benzyloxypropanol in 250 ml. of benzene. The reaction was stirred 15 hours longer and then diluted with 40 ml. of methanol. The mixture was filtered through diatomaceous earth and the filtrate evaporated to an oil. Distillation of the crude oil yielded 28 g. (53%) of the title compound as an oil.
b.p.: 94°-97° C. (0.45 torr)
PMR (CDCl$_3$) $\delta$ 2.00 (quintet, J=6 Hz, methylene), 3.20 (t, J=6 Hz, methylene), 3.43 (t, J=6 Hz, methylene), 4.42 (s, benzylic methylene) and 7.20 (s, PhH).

PREPARATION L

(R)-1-Bromo-2-benzyloxy-4-(1-methyl-4-phenylbutoxy)benzene

A mixture of 21.8 g. (78 mmole) of 3-benzyloxy-4-bromophenol, 20.0 g. (82.6 mmole) of (S)-1-methyl-4-phenylbutylmethane sulfonate and 25.2 g. (200 mmole) of potassium carbonate in 100 ml. dimethylformamide was heated at 85° C. for 13.5 hours. The reaction was cooled and added to 500 ml. water-500 ml. ether. The organic extract was washed with two 250 ml. portions of water, dried over magnesium sulfate and evaporated to an oil. The crude oil was purified via column chromatography on 750 g. of silica gel eluted with 10% ether-hexane to yield 23.9 g. (72%) of the title compound as an oil.
$[\alpha]_D{}^{25°} = -11.39°$ (C=1.137, CH$_3$Cl)
IR (CHCl$_3$) 1574 cm$^{-1}$.
HRMS (m/e) 426.1011 (M+, Calc'd for C$_{24}$H$_{25}$O$_2$Br, 426.1012), 424, 280, 278, 104 and 91.
PMR $\delta_{CDCl_3}{}^{TMS}$ 1.22 (d, J=6 Hz, methyl), 1.4-2.0 (m), 2.60 (m, benzylic methylene), 4.24 (m, methine), 5.07 (s, benzylic methylene), 6.30 (d, J=2 Hz and 8 Hz, ArH), 6.46 (d, J=2 Hz, ArH), 7.17 (S, PhH) and 7.35 (m, PhH).

PREPARATION M

2-(3-Hydroxyphenyl)-2-methylpropanal

A mixture of 38.9 g. (0.153 mole) of 2-(3-benzyloxyphenyl)-2-methylpropanal, 20 g. 5% Pd/C/50% water, 1.0 sodium bicarbonate and 150 ml. ethanol was shaken overnight under 55 psi of hydrogen. The reaction was filtered through diatomaceous earth, the filter cake washed with ethanol and the combined filtrate evaporated. The residue was reduced as above for another 8 hours. Another 10 g. portion of catalyst was added and the reaction continued overnight. The reaction was worked-up as above and the residue purified via column chromatography on 500 g. of silica gel eluted with 25% ether-hexane to yield 14 g. (56%) of the title compound as an oil.
PMR (CDCl$_3$) $\delta$ 1.42 (s, gem dimethyl), 6.36 (bs, OH), 6.7-6.9 (m, ArH), 7.05-7.2 (m, ArH) and 9.62 (s, CHO).

PREPARATION N

2-[3-(Tetrahydropyranyl-2-oxy)phenyl]-2-methylpropanal

To a 0° C. solution of 11.3 g. (0.0688 mole) of 2-(3-hydroxyphenyl)-2-methylpropanal and 11.1 ml. (0.122 mole) of dihydropyran in 113 ml. dichloromethane was added several crystals of p-toluenesulfonic acid monohydrate. The reaction was stirred one hour at 0° C. and then added to 60 ml. saturated sodium bicarbonate-460 ml. ether. The ether extract was washed once with 100 ml. saturated sodium chloride, dried over magnesium sulfate and evaporated to yield 15.3 g. (89%) of the title compound as an oil.
IR (CHCl$_3$) 1727, 1603 and 1582 cm$^{-1}$.
PMR (CDCl$_3$) $\delta$ 1.48 (s, gem dimethyl), 1.5-2.1 (m), 3.4-4.2 (m), 5.37 (m, methine), 6.7-7.4 (m, ArH) and 9.53 (s, CHO).

PREPARATION O

1,1-Dimethyl-1-[3-(tetrahydropyranyl-2-oxy)phenyl]-cis-2-heptane

To a 15° C. solution of 75.5 mmole of dimsyl sodium (from sodium hydride and dimethyl sulfoxide) in 94 ml. dimethyl sulfoxide was added portionwise, 31.2 g. (75.5 mmole) of n-pentyltriphenylphosphonium bromide. The resultant slurry was stirred 30 minutes and the 15.3 g. (61.6 mmole) of 2-[3-(tetrahydropyranyl-2-oxy)- phenyl]-2-methylpropanal was added over 15 minutes. The reaction mixture was stirred 50 minutes at 15° C. and then added to 800 ml. ice-800 ml. ether. The aqueous phase was extracted twice with 400 ml. of ether. The combined ether extract was washed once with 250 ml. water and once with 250 ml. saturated sodium chloride, dried over magnesium sulfate and evaporated to yield an oil. Triphenylphosphine oxide was removed by crystallization from pentane. The remaining oily residue was purified via column chromatography on 1 kg. of silica gel eluted with 0.75% ether-hexane to yield 17.7 g. (95%) of the title compound as an oil.

IR (CHCl$_3$) 1603 and 1581 cm$^{-1}$.

PMR (CDCl$_3$) δ 0.76 (m, terminal CH$_3$), 1.20 (s, gem dimethyl), 3.3–4.1 (m), 4.9–5.4 (m, 2H), 5.56 (d, J=12 Hz) and 6.6–7.3 (m, ArH).

PREPARATION P

Trans-3-methyl-4-(2-propenyl)cyclohexanone

To a 0° C. solution of 0.282 mole of dimethyl copper lithium in 200 ml. of tetrahydrofuran was slowly added a solution of 25.6 g. (0.188 mole) of 4-(2-propenyl)cyclohex-2-en-1-one in 50 ml. of tetrahydrofuran. The reaction was stirred 15 minutes and then quenched by addition to a 0° C. saturated solution (500 ml.) of ammonium chloride. The quenched reaction was extracted with 500 ml. ether. The ether extract was washed with 500 ml. saturated ammonium chloride, dried over magnesium sulfate and evaporated to an oil which was purified via distillation to yield 15.5 g. (55%) of the title compound.

BP 110°–113° C. (15 torr)

IR (CHCl$_3$) 1710 and 1640 cm$^{-1}$.

MS (m/e) 152 (M+), 136, 110.

Analysis: Calcd. for C$_{10}$H$_{16}$O: C, 78.89; H, 10.59. Found: C, 78.76; H, 10.24.

PMR (CDCl$_3$) δ 1.05 (d, J=6 Hz, methyl), 1.0–3.0 (m), 4.8–5.3 (m, vinyl H) and 5.4–6.1 (m, vinyl H).

Similiarly, trans-3-methyl-4-(2-propenyl)cycloheptanone is produced from 4-(2-propenyl)cyclohept-2-en-1-one.

PREPARATION Q

5-Methyl-4-(2-propenyl)-2-phenylsulfenylcyclohexanone

To a 0° C. mixture of 16.9 g. (0.109 mole) of methyl benzenesulfinate and 8.68 g. (0.217 mole) of potassium hydride in 100 ml. of dimethoxyethane was slowly added a solution of 15.0 g. (0.0987 mole) of trans-3-methyl-4-(2-propenyl)cyclohexanone in 50 ml. of dimethoxyethane. The reaction was stirred 30 minutes longer at 0° C. and then cautiously added to 500 ml. of ice-saturated sodium chloride and 45 ml. 6 N hydrochloric acid. The quenched reaction mixture was extracted once with 300 ml. ether and once with 200 ml. dichloromethane. The organic extract was dried over magnesium sulfate and evaporated to give a quantitative yield of the title compound as a semisolid mixture of axial and equatorial sulfenates. Crystallization from ether yields 7.8 g. of pure axial sulfenate.

Axial Sulfenate:

PMR (CDCl$_3$) δ 1.05 (d, J=5 Hz, methyl), 1.0–2.7 (m),  3.39 (dd, J = 11 and 6Hz, CHS), 4.7–5.2 (m, vinyl H), 5.3–6.1 (m, vinyl H) and 7.4 (m, PhH).

In like manner, 3-methyl-4-(2-propenyl)cyclohept-2-en-1-one is converted to 5-methyl-4-(2-propenyl)-2-phenylsulfenylcycloheptanone.

PREPARATION R

Trans-5-methyl-4-(2-propenyl)cyclohex-2-en-1-one

A mixture of 96.7 mmole of 5-methyl-4-(2-propenyl)-2-phenylsulfenylcyclohexanone and 10 g. (100 mmole) of calcium carbonate in 300 ml. of toluene was heated at 110° C. for 40 minutes. The reaction was cooled, magnesium sulfate added and filtered. The filtrate was evaporated and the residue purified via column chromatography on 300 g. of silica gel eluted with 20% ether-hexane and then distillation to yield 7.61 g. (52%) of the title compound.

BP 50° C. (0.03 torr).

PMR (CDCl$_3$) δ 1.11 (d, J=6 Hz, CH$_3$), 1.3–2.9 (m), 4.8–5.3 (m, vinyl H), 5.3–6.2 (m, vinyl H), 5.95 (bd, J=10 Hz, C-2 H) and 6.80 (bd, J=10 Hz, C-3 H).

By means of this procedure, 5-methyl-4-(2-propenyl)-2-phenylsulfenylcycloheptanone is converted to trans-5-methyl-4-(2-propenyl)cyclohept-2-en-1-one.

PREPARATION S

3-[2-Benzyloxy-4-(1,1-dimethylheptyl)phenyl]cyclohex-3-en-1-one ethylene ketal

A solution of 500 mg. of 3-[2-benzyloxy-4-(1,1-dimethylheptyl)phenyl]cyclohex-2-en-1-one, 7.8 g. of ethylene glycol, 375 mg. of hydroquinone and 50 mg. of p-toluenesulfonic acid monohydrate in 50 ml. of benzene is heated at reflux for 12 hours using a Dean-Stark condenser filled with 3A molcular sieves. The reaction is cooled, added to 500 ml. saturated sodium bicarbonate and the quenched mixture extracted with three 150 ml. portions of ether, dried over magnesium sulfate and evaporated to a solid. This solid is purified via column chromatography on 50 g. of silica gel eluted with 50% ether-petroleum ether to yield the title product.

Similarly, 3-[2-benzyloxy-4-(1,1-dimethylheptyl)-phenyl]cyclohept-3-en-1-one ethylene ketal is prepared from 3-[2-benzyloxy-4-(1,1-dimethylhepty)phenyl]cyclohept-2-en-1-one.

PREPARATION T

3-[2-Benzyloxy-4-(1,1-dimethylheptyl)phenyl]cyclohex-2-enone

A solution of 3.89 g. (10 mmoles) of 2-(3-benzyloxy-4-bromophenyl)-2-methyloctane in 10 ml. of tetrahydrofuran was slowly added to 360 mg. (14.4 mmoles) of 70–80 mesh magnesium metal. The resulting mixture was refluxed for 30 minutes and then cooled to 0° C. To this solution was slowly added a solution of 1.40 g. (10 mmoles) of 3-ethoxy-2-cyclohexen-1-one in 3 ml. of tetrahydrofuran. The reaction mixture was stirred for 30 minutes at 0° C. and then quenched by the addition of 20 ml. of 1 N sulfuric acid and heating on the steam bath for 30 minutes. It was then cooled and added to 200 ml. of ether-200 ml. of water. The organic extract was washed successively with 200 ml. of saturated sodium bicarbonate and 200 ml. of saturated sodium chloride, dried over magnesium sulfate and evaporated to an oil. The crude product was purified via column chromatography on 170 g. of silica gel eluted with 1:1 ether:pentane to yield 2.5 g. (54%) of the title compound as an oil.

IR (CHCl$_3$) 1667, 1610 and 1558 cm$^{-1}$.

MS (m/e) 404 (M+), 319, 313 and 91.

In like manner, 3-[2-benzyloxy-4-(1,1-dimethylheptyl)phenyl]cyclohepten-2-enone is prepared from 3-ethoxy-2-cyclohepten-1-one.

PREPARATION U

6-[2-Benzyloxy-4-(1,1-dimethylheptyl)phenyl]cyclohept-3-en-1-one

To a 0° C. slurry of 2.19 g. (0.055 mole) of potassium hydride in 20 ml. of dimethoxyethane is added 4.32 g. (0.028 mole) of methyl phenylsulfinate. To the resultant mixture is added, dropwise over a 30 minute period, a solution of 9.82 g. (0.024 mole) of 3-[2-benzyloxy-4-(1,1-dimethylheptyl)phenyl]cycloheptanone in 20 ml. of dimethoxyethane. The reaction is stirred one hour at 0° C. and then quenched by dropwise addition of 1 ml. of water. The quenched reaction mixture is added to 15 ml. ether-15 ml. dichloromethane-12.5 ml. 6 N HCl-40 ml. saturated sodium chloride. The aqueous phase is extracted with another 15 ml. portion of dichloromethane. The combined organic extract is dried over magnesium sulfate and evaporated to a semisolid. It is used as is in the next step.

The crude product thus obtained is mixed with 2.68 g. (0.0268 mole) of calcium carbonate in 100 ml. of toluene and heated at 110° C. for 30 minutes. The reaction mixture is cooled, filtered through magnesium sulfate and the filtrate evaporated on a rotovapor to yield an oil which was purified via column chromatography on 500 g. of silica gel eluted with 39% ether-hexane to yield the title compound.

We claim:

1. A compound having the formula

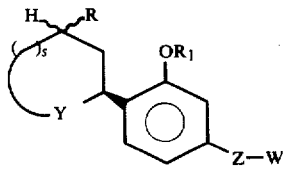

wherein
R is hydroxy, mandeloyloxy or alkanoyloxy having from one to five carbon atoms; carbon atoms;
s is an integer of 1 or 2;
Y is —CH(R$_2$″)CH(R$_2$)— or —CH(R$_3$)CH$_2$—;
R$_2$″ is hydrogen or methyl;
R$_2$ is X-substituted alkyl having from one to six carbon atoms;
R$_3$ is X-substituted alkyl having from one to three carbon atoms;
X is —OR$_6$;
R$_6$ is hydrogen, alkyl having from one to six carbon atoms or acetyl;
W is hydrogen; and Z is
(a) alkylene having from five to thirteen carbon atoms; or
(b) -(alk$_1$)$_m$-O-(alk$_2$)$_n$- wherein each of (alk$_1$) and (alk$_2$) is alkylene having from one to thirteen carbon atoms; each of m and n is 0 or 1; with the provisos that the summation of carbon atoms in (alk$_1$) plus (alk$_2$) is not less than five or greater than thirteen.

2. A compound according to claim 1 wherein Z is alkylene having from seven to eleven carbon atoms.

3. A compound according to claim 2 wherein R$_1$ is hydrogen.

4. A compound according to claim 3 wherein R is hydroxy, Z-W is 1,1-dimethylheptyl and R$_2$″ is hydrogen.

5. A compound according to claim 4 wherein Y is —CH(R$_2$″)CH(R$_2$)— and s is 1.

6. The compound according to claim 5 wherein R$_2$ is 3-hydroxypropyl.

7. The compound according to claim 6 having the formula

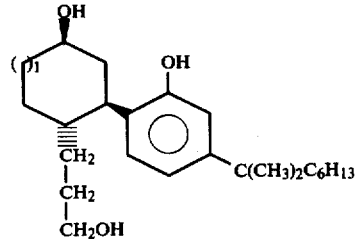

8. A compound according to claim 4 wherein Y is —CH(R$_2$″)CH(R$_2$)— and s is 2.

9. The compound according to claim 8 wherein R$_2$ is 3-hydroxypropyl.

10. The compound according to claim 9 having the formula

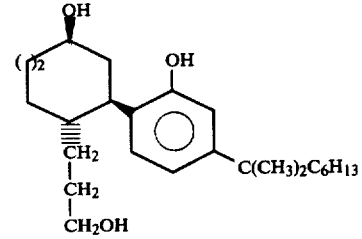

* * * * *